United States Patent
Islam et al.

(10) Patent No.: US 11,161,823 B2
(45) Date of Patent: Nov. 2, 2021

(54) ANTICANCER 1,3-DIOXANE-4,6-DIONE DERIVATIVES AND METHOD OF COMBINATORIAL SYNTHESIS THEREOF

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Imadul Islam, Riyadh (SA); Rabih O. Al-Kaysi, Riyadh (SA); Mohamed Boudjelal, Riyadh (SA); Rizwan Ali, Riyadh (SA); Atef Nehdi, Riyadh (SA); Bandar Alghanem, Riyadh (SA)

(73) Assignees: National Guard Health Affairs, Riyadh (SA); King Saud bin Abdulaziz University for Health Sciences, Riyadh (SA); King Abdullah Inetrnational Medical Research Center, Riyadh (SA)

( * ) Notice: Subject to any disclaimer, the term of this patent is extended or adjusted under 35 U.S.C. 154(b) by 0 days.

(21) Appl. No.: 16/810,051

(22) Filed: Mar. 5, 2020

(65) Prior Publication Data
US 2020/0290975 A1    Sep. 17, 2020

Related U.S. Application Data

(60) Provisional application No. 62/816,584, filed on Mar. 11, 2019.

(51) Int. Cl.
| | | |
|---|---|---|
| C07D 239/62 | (2006.01) | |
| C07D 319/06 | (2006.01) | |
| A61P 35/00 | (2006.01) | |
| C07D 277/34 | (2006.01) | |
| C07D 409/06 | (2006.01) | |
| C07D 417/06 | (2006.01) | |
| C07D 405/06 | (2006.01) | |
| C07D 407/10 | (2006.01) | |
| C07D 401/06 | (2006.01) | |

(52) U.S. Cl.
CPC ............ *C07D 239/62* (2013.01); *A61P 35/00* (2018.01); *C07D 277/34* (2013.01); *C07D 319/06* (2013.01); *C07D 401/06* (2013.01); *C07D 405/06* (2013.01); *C07D 407/10* (2013.01); *C07D 409/06* (2013.01); *C07D 417/06* (2013.01)

(58) Field of Classification Search
CPC .............................. C07D 239/62; A61P 35/00
See application file for complete search history.

(56) References Cited

FOREIGN PATENT DOCUMENTS

| | | |
|---|---|---|
| CN | 104140381 A | 11/2014 |
| WO | 03/035615 A2 | 5/2003 |
| WO | 03/035616 A2 | 5/2003 |
| WO | 2007/054292 A2 | 5/2007 |
| WO | 2009/029844 A1 | 3/2009 |

OTHER PUBLICATIONS

Ogawa et al (1989): STN International CAPLUS database, (Columbus, Ohio), Accession No. 1989: 95120.*
Campbell et al (1997): STN International CAPLUS database, (Columbus, Ohio), Accession No. 1997: 575907.*
Krapivin et al (1995): STN International CAPLUS database, (Columbus, Ohio), Accession No. 1995: 376566.*
Balzarini, et al.; Structural Analogs of Umifenovir. 1. Synthesis and Biological Activity of Ethyl 5-Hydroxy-1-Methyl-2-(Trans-2-Phenylcyclopropyl)-1H-Indole-3-Carboxylate; Chemistry of Heterocyclic Compounds 50; pp. 489-495; Jun. 8, 2014; 15 Pages.

* cited by examiner

*Primary Examiner* — Golam M Shameem
(74) *Attorney, Agent, or Firm* — Oblon, McClelland, Maier & Neustadt, L.L.P.

(57) ABSTRACT

Compounds, methods of synthesis, and methods of cancer treatment by arylidene-1,3-dioxane-4,6-diones. A Meldrum's acid-based chemistry and hybrid solid-liquid method. The method includes protection of ketone and aldehyde components and simultaneous immobilization on the solid phase, introduction of substituents, grafts and derivatives compatible with the protection, detachment and restoration of active carbonyl reactivity, reaction of ketone library with malonate, reacting of the products with the aldehyde library in liquid phase and separation of the products by preparative HPLC.

11 Claims, 3 Drawing Sheets

ANTICANCER 1,3-DIOXANE-4,6-DIONE DERIVATIVES AND METHOD OF COMBINATORIAL SYNTHESIS THEREOF

CROSS-REFERENCE TO RELATED APPLICATIONS

The present application claims benefit of priority from U.S. Provisional Application No. 62/816,584, having a filing date of Mar. 11, 2019, which is incorporated herein by reference in its entirety.

BACKGROUND OF THE INVENTION

Technical Field

The present disclosure relates to 1,3-dioxane-4,6-dione compounds and associated derivatives, pharmaceutical compositions containing the 1,3-dioxane-4,6-dione compounds, and methods of treating cancer by administering the compounds.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Malignancies are among the leading causes of death and disability. An estimated 18.1 million new cancer cases (17.0 million excluding nonmelanoma skin cancer) and 9.6 million cancer deaths (9.5 million excluding nonmelanoma skin cancer) are expected in coming years. The most frequently diagnosed cancers and the leading causes of cancer death vary across countries and within each country depending on the degree of economic development and associated social and lifestyle factors (See F. Bray, J. Ferlay, I. Soerjomataram, R. L. Siegel, L. A. Torre, A. Jemal, *CA: a cancer journal for clinicians*, 2018, v. 68(6), 394-424).

The problem of cancer resistance to therapy and the possibility of synergy between different drug classes or radiotherapy necessitates the search for novel agents to use as monotherapies or as components of combination therapies (S. M. Vareki, K. Y. Salim, W. R. Danter, J. Koropatnick. *PloS one*, 2018, v. 13(1): e01. 91766.). In this context, 1,3-dioxane-4,6-diones are known as biologically active and may serve as an interesting candidate group for the development of novel antineoplastic agents. Applications include inhibition of aldose reductase (W. G. Rajeswaran, R. B. Labroo, L. A. Cohen, M. M. King, *The Journal of Organic Chemistry*. 1999; v. 64(4), 1369-71); psychotropic activity (E. Lukevics, L. Ignatovich, I. Shestakova, *Applied organometallic chemistry*, 2003, v. 12, 898-905), platelet aggregation inhibitors (E. 1. Maatougui, A. Coelho, E. Cano, M. Yanez, C. López C, V. Yaziji, C. Carbajales, E. Sotelo, *Combinatorial chemistry & high throughput screening*, 2012, v. 15(7), 551-4), Patent reference CN104140381A discloses RN 1625629-47-1 or 1,3-dioxane-4,6-dione, 2-[(2E)-3-[4-(dimethylamino)phenyl]-2-propen-1-ylidene]-5,5-dimethyl with the following formula (termed "MAAD-2" see page 23 of CN '381).

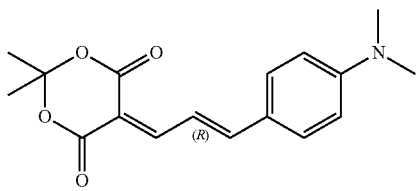

The aryl substituent in MAAD-2 is 4-(dimethylamino) phenyl. The compounds of CN '381 are not directed to cancer treatment, and RN 1625629-47-1 was identified as an intermediate, not a final therapeutic lead.

Non-patent reference to Balzarini et al. published in *Chemistry of Heterocyclic Compounds*, 2014, V. 50(4), pp 489-495 discloses RN 1616406-68-8 or 1,3-dioxane-4,6-dione, 2-[hydroxy[(1R,2R)-2-phenylcyclopropyl]methylene]-5,5-dimethyl-, rel

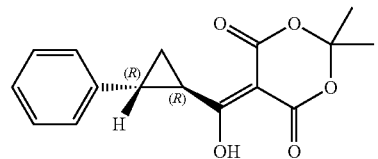

The compound features a cyclopropyl substituent in the linker between the dione and aryl groups, i.e., 2-[hydroxy [(1R,2R)-2-phenylcyclopropyl]methylene]. Balzarini discloses the use of the compound as an intermediate in the synthesis of an antiviral, not as an anti-cancer agent.

Patent reference WO2009029844 discloses RN 138871-92-8 or 1,3-dioxane-4,6-dione, 2-(1-hydroxy-3-phenylpropylidene)-5,5-dimethyl.

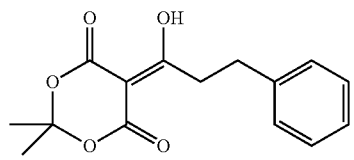 [SMILES: CC1(C)OC(=O)C(=C(O)CCc2ccccc2)C(=O)O1]

The presence of a hydroxyl group at a position adjacent to an alkene bond produces a keto tautomer. The role of the WO '844 compounds is to serve as a synthesis intermediate. Patent references WO2007054292, WO2003035616, WO2003035615 are similar to WO '844 and disclose RN 138871-92-8 or 1,3-dioxane-4,6-dione, 2-(1-hydroxy-3-phenylpropylidene)-5,5-dimethyl. However, these compounds are not the final therapeutic leads and are disclosed as intermediates.

Y. Hu, P. Wei, H. Huang, Z. G., Z. C. Chen in *Synthetic Communications*, 2005, v. 35, pp. 2955-2960 discloses the reaction below:

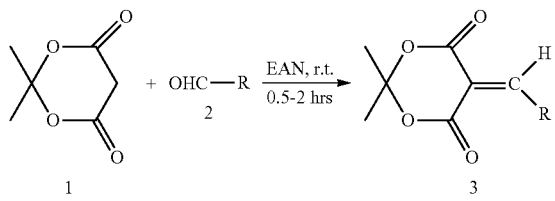

The group R comprises $C_6H_5$, p-Me$_2$NC$_6$H$_4$, p-MeOC$_6$H$_4$, p-OHC$_6$H$_4$, 3,4-(OCH$_2$)C$_6$H$_3$, p-ClC$_6$H$_4$, p-NO$_2$C$_6$H$_4$, o-NO$_2$C$_6$H$_4$, 2-Furyl-C$_6$H$_5$, p-Me$_2$NC$_6$H$_4$, p-Me$_2$NC$_6$H$_4$. In Hu the spacing is 2 covalent bonds (or one double bond) between the dioxane ring and the aromatic group R. Hu et al. do not disclose the anti-cancer activity of the compounds.

T. S. Jin, R, Q, Zhao R Q, Li M, Zhao Y, Li T S. in *Arkivoc.* 2006, v. 14, pp. 53-8, discloses a procedure for synthesis of 5-arylmethylene-2,2-dimethyl-1,3-dioxane-4,6-diones in aqueous media, including: 5-benzylidene-2,2-dimethyl-1,3-dioxane-4,6-diones; 2,2-dimethyl-5-(4-methyl-benzylidene)-1,3-dioxane-4,6-diones; 5-(4-methoxybenzylidene)-2,2-dimethyl-1,3-dioxane-4,6-diones; 2,2-dimethyl-5-(3,4-dioxymethylenebenzylidene)-1,3-dioxane-4,6-diones; 5-(4-hydroxybenzylidene)-2,2-dimethyl-1,3-dioxane-4,6-diones; 2,2-dimethyl-5-(4-dimethylaminobenzylidene)-1,3-dioxane-4,6-diones; 5-(4-chlorobenzylidene)-2,2-dimethyl-1,3-dioxane-4,6-diones; 2,2-dimethyl-5-(4-nitrobenzylidene)-1,3-dioxane-4,6-diones; 5 and -(2-furylmethylene)-2,2-dimethyl-1,3-dioxane-4,6-diones. The compounds have 2 covalent bond spacing between the dioxane ring and the aromatic group R. Jin et al. does not disclose anti-cancer activity of the compounds.

The PubChem record CID 880824 discloses 2-tert-butyl-2-methyl-5-[(E)-3-phenylprop-2-enylidene]-1,3-dioxane-4,6-dione. The record discloses biological activities of the structure, and lists the bioassays, however does not disclose its anti-cancer activity. The same applies to 5-cinnamylidene-2,2-dimethyl-1,3-dioxane-4,6-dione (CID 1478-264). Other analogs are 3-cinnamylidene-1,5-dioxaspiro[5.5]undecane-2,4-dione (CID 9159284) 2,2-dimethyl-5-[3-(4-methylphenyl)-2-propenylidene]-1,3-dioxane-4,6-dione (CID 101168718), and testing of these compounds for anti-neoplastic activity is not reported.

The synthesis of 4-R-phenylallylidene Meldrum's acid derivatives is described in D. Insuasty, H. Torres, R. Abonia, J. Quiroga, J. Low, A, Sanchez, J. Cobo and M. Nogueras. *In Heterocyclic Communications.* 2005, v. 11(1), pp 55-60. The synthetic method leads to 5-[3-phenylallylidene]-2,2-dimethyl-[1,3]dioxane-4,6-dione, 5-[3-(4-methylphenyl)allylidene]-2,2-dimethyl-[1,3]dioxane-4,6-dione, 5-[3-(4-methoxyphenyl)allylidene]-2,2-dimethyl-[1,3]dioxane-4,6-dione, 5-[3-(4-chlorophenyl)allylidene]-2,2-dimethyl-[1,3]dioxane-4,6-dione, 5-[3-(4-bromophenyl)allylidene]-2,2-dimethyl-[1,3]dioxane-4,6-dione, 5-[3-(4-nitrophenyl)allylidene]-2,2-dimethyl-[1,3]dioxane-4,6-dione, none are reported to display anti-cancer activity.

The publication by de H. N. Armas, N. M. Blaton, O. M. Peeters, C. J. De Ranter, M. Suárez, E. Ochoa, Y. Verdecia, E, Salfrán in *Journal of chemical crystallography,* 2000, 30(3), 189-94 discloses the synthesis, crystal structure and molecular modeling (AM1) of two 5-arylidene derivatives of Meldrum's acid. The specific embodiments 5-(4-nitrobenziliden)-2,2-dimethyl-1,3-dioxane-4,6-dione, and 5-(4-methoxybenziliden)-2,2-dimethyl-1,3-dioxane-4,6-dione do not disclose antineoplastic activity.

The publication by J. N. Low, J. Cobo, M. Nogueras, A, Sanchez, B. Insuasty, H. Torres *Acta Cryst,* 2002, V. C58, p 39-p 41 discloses 2,2-dimethyl-5-[3-(4-methyl-phenyl)-2-propenylidene]-1,3-dioxane-4,6-dione, 5-[3-(4-chlorophenyl)-2-propenylidene]-2,2-dimethyl-1,3-dioxane-4,6-dione but it was not tested for antitumor effects.

None of the aforementioned references describe the use of the dioxone compounds in anti-neoplastic activity assays, the presence of such activity or for treatment of cancer. Furthermore, all published structures incorporated a single phenyl ring in the respective domain. It is the object of the present disclosure to provide 1,3-dioxane-4,6-dione compounds and associated derivatives as agents for treating cancer.

BRIEF SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

According to a first aspect, the present disclosure include compounds having the 1,3-dioxane-4,6-dione structure (I):

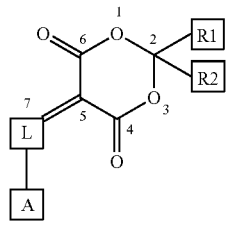

wherein L is a linker,
wherein the linker L comprises the structures:

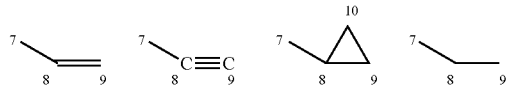

wherein each carbon 7, 8 or 9 can be substituted (except when carbons 8 and 9 are acetylenically bonded to one another) by, independently, one or more hydrogens or by side chains attached to the carbons 7, 8 or 9 individually, with the number of said side-chains from 0 to 6 (available individual attachment sites in L), or by rings connecting any of the position 7-9, wherein the side chains can be linear or branched, substituted or unsubstituted, be only carbon or include heteroatoms, wherein the rings can be aliphatic or aromatic, monocyclic or polycyclic, homocyclic or heterocyclic if aromatic, carbon only or including heteroatoms if aliphatic, unsubstituted or substituted, wherein the number of the possible rings is 0-2 in the L region between 7-9 (number of the attachment point combinations in different L in consideration of steric interference and synthetic feasibility), wherein 0-6 rings can form between the linker domain L and domains R1, R2 and A, including all substituents of all domains R1, R2 and A thereof, wherein all substituents in the positions 7-9 of the linker can be charged or uncharged, radical or with paired (non-radical) electronic structure, isotopically substituted or unsubstituted, wherein the substituents in the positions 7-9 of the linker and in the above-described substituents are independently: hydrogen, alkyls, cycloalkyls, alkenes, cycloalkenes, alkynes, linear or cyclic dienes, dienophiles, acyls, anhydrides, haloanhydrides, halides, carbenes, amides, ethers, esters, hydroxyls, aldehydes, ketones, acetals, ketals, hemiacetals, carboxylic groups, amines, nitriles, isonitriles, cyanides, nitrates, nitrites, azides, hydrazides, enamines, oximes, thiols, sulfates, sulfoxides, sulfonamides, sulfones, siloxanes, silanes, silyls, aminoacids, nucleotides, oligonucleotides, polynucleotides, chelators, sugars, lipids, metalloorganic compounds, antibodies, proteins, polymers, nanotubes, fullerenes, nanoparticles, viruses and other active or stable groups capable of covalently binding carbon, wherein the carbon 9 of the linker is connected by a single bond to the aromatic system A, wherein the connecting bond can be C—C, C—N, C—O, C—S, wherein A is a mononuclear or polynuclear aromatic system comprising the structure:

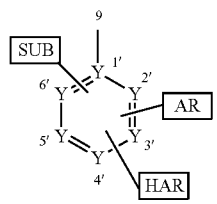

wherein the position 9 is the above-described carbon on the linker L, wherein Y are any of C, N, O and S forming together a 6 or 5-member aromatic system, wherein the number of atoms of any elements among C, N, O, S can be 0 to 6 in the positions 1'-6' of the ring, wherein SUB are non-bridging substituents or non-aromatic bridging substituents, wherein the non-bridging substituents have only one connection to the ring 1'-6' and are termed "non-bridging" only in this sense, while within the chain the rings and bridged structures are allowed, wherein the non-aromatic bridging substituents connect any of the positions 1'-6' with any of the positions 1'-6' in any order, with the proviso that the aromatic rings that form as parts of the bridges are not directly fused with the ring 1'-6', the term "non-aromatic" means only the absence of direct contact of the substituting ring with the ring 1'-6' in 2 adjacent position that would have allowed to expand the aromatic system and form a fused ring, wherein AR are all-carbon aromatic substituents, defined as fused rings formed by overlapping any of the bonds 1'-2', 2'-3', 3'-4', 4'-5', 5'-6' with one bond comprising the substituting all-carbon aromatic ring. Under this definition, all systems are fused. The number of the adjacent AR rings is in the range 0-2.

wherein HAR are heteroaromatic substituents, defined as fused rings formed by overlapping any of the bonds 1'-2', 2'-3', 3'-4', 4'-5', 5'-6' with one bond comprising the substituting heteroaromatic ring. Under this definition, all systems are fused. The number of the adjacent HAR rings is in the range 0-2, wherein the ring 1'-6' and its AR, HAR or combined or mixed AR/HAR substituents are termed together "aromatic domain" of the compound of formula (I), wherein the mutual relative positions of all heteroatoms and all substituents in the aromatic domain are unrestricted, wherein the positions of all heteroatoms and/or of substituents vs. the bond connecting the aromatic domain to the atom 9 of the linker are unrestricted, wherein 0-10 aliphatic or aromatic, carbocyclic or heterocyclic rings can form between the substituents SUB, between SUB and L and between SUB and R1 or R2, between SUB and AR or HAR, between AR and HAR, between AR and AR, between HAR and HAR, or between the substituents thereof in any combination, wherein R1 and R2 are linear or branched alkyls, cycloalkyls, substituted alkyls, independently substituted by hydrogen or by other groups, wherein 1 carbon or more connected to the carbon 2 of the 1,3-dioxane-4,6-dione ring of the compound of formula (I) are defined as an alkyl, with the first bond counted from the carbon 2 being a carbon-carbon bond, wherein 0-10 aromatic or aliphatic, carbocyclic or heterocyclic rings can form between R1 and R2, between any of R1 or R2 and L, between any of R1 or R2 and SUB, between any of R1 or R2 and AR or HAR or between the substituents thereof in any combinations, wherein the groups R1, R2, SUB, AR and HAR can be further substituted independently by hydrogens, alkyls, cycloalkyls, alkenes, cycloalkenes, alkynes, dienes, dienophiles, aryls, acyls, anhydrides, haloanhydrides, halides, carbenes, amides, ethers, esters, hydroxyls, aldehydes, ketones, acetals, ketals, hemiacetals, carboxylic groups, amines, nitriles, isonitriles, cyanides, nitrates, nitrites, azides, hydrazides, enamines, oximes, thiols, sulfates, sulfoxides, sulfonamides, siloxanes, silanes, silyls, aminoacids, nucleotides, chelators, sugars, lipids, metalloorganic compounds, rings formed between the substituents, grafting groups connecting to polymers, graphene or nanotubes or nanoparticles or dendrimers or aptamers or antibodies or proteins or sugars or lipids or nucleotides or polynucleotides or other pharmaceuticals or metallo-organic compounds or toxins or viruses or any active or stable groups capable of covalently binding carbon, wherein the alkyls that substitute any of L, R1, R2 and A are a saturated straight, branched, or cyclic, primary, secondary, or tertiary hydrocarbon of typically C1 to C8, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl such that the term optionally includes substituted alkyl groups and moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, wherein the aryls that substitute any of L, R1, R2 and A include both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary.

According to a second aspect, the invention discloses the general method of synthesis of the generic Markush group, According to a third aspect, the invention discloses the specific embodiments.

According to a fourth aspect, the invention discloses testing of the compounds as anti-neoplastic agents.

According to a fifth aspect, the invention presents a strategy of combinatorial synthesis and improvement of the compound of formula (I).

According to a sixth aspect, the invention presents combinatorial derivatives of the compound of formula (I).

According to a seventh aspect, the invention presents a hybrid liquid-solid combinatorial scheme, wherein the aldehyde library (see below) is immobilized on a solid support, variant-expanded, detached and reacted in liquid phase with the Meldrum's products of the ketone library (see below).

According to an eighth aspect, the synthesis of the ligand libraries is directed by feedback from the testing panel that includes the primary normal human cells and organoid arrays, with the assays conducted in the presence of serum, therefore providing a high fidelity estimate of a ligand's potential to pass higher-order tests.

According to a ninth aspect, the methods of cancer treatment by the inventive compounds, derivatives and combinations with the other therapeutics are disclosed.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
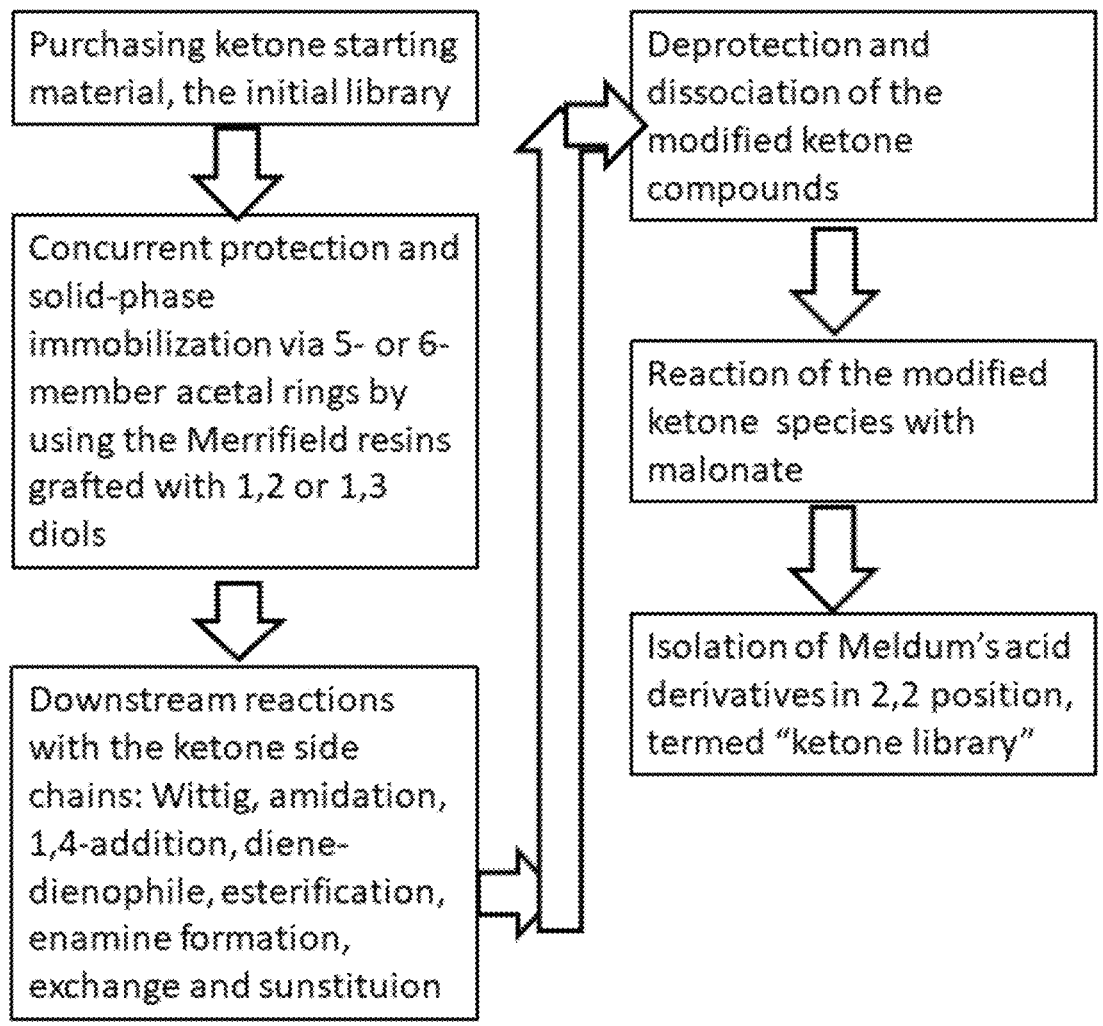
FIG. 1 shows a flow chart for a process of developing a ketone library semi-product.

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Additionally, within the description of this disclosure, where a numerical limit or range is stated, the endpoints are included unless stated otherwise. Also, all values and subranges within a numerical limit or range are specifically included as if explicitly written out.

As used herein, the terms "optional" or "optionally" means that the subsequently described event(s) can or cannot occur or the subsequently described component(s) may or may not be present (e.g. 0 wt %).

As used herein, "compound" and "complex" are intended to refer to a chemical entity, whether in the solid, liquid or gaseous phase, and whether in a crude mixture or purified and isolated.

The term "alkyl", as used herein, unless otherwise specified, refers to a saturated straight, branched, or cyclic, primary, secondary, or tertiary hydrocarbon of typically C1 to C8, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary.

The term "aryl", as used herein, and unless otherwise specified, refers to phenyl, biphenyl, naphthyl, anthracenyl, phenanthrenyl, acenaphtyl without limitation. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary.

As used herein, the term "therapeutic window" refers to the difference in the dosage that causes a therapeutic effect and the dosage that causes toxicity.

As used herein, the term "binding profile" refers to the plurality of binding constants between the ligand and the putative binding sites in the target organism.

As used herein, the term "TLC" refers to "thin layer chromatography".

As used herein, the term "drug-likeness" refers to the potential of a compound to become an effective pharmaceutical based on the analysis of already successful pharmaceuticals.

As used herein, the term "Lipinski rule" defines drug-likeness quantitatively. Lipinski's rule states that an orally active drug has no more than one violation of the following criteria:
 No more than 5 hydrogen bond donors (the total number of nitrogen-hydrogen and oxygen-hydrogen bonds,
 No more than 10 hydrogen bond acceptors (all nitrogen or oxygen atoms),
 A molecular mass less than 500 daltons,
 An octanol-water partition coefficient (log P) that does not exceed 5.

As used herein, "octanol-water partition coefficient P" is defined as a particular ratio of the concentrations of a solute between the two immiscible or partially miscible solvents (a biphase of liquid phases), specifically for un-ionized solutes, and the logarithm of the ratio is log P.

As used herein, the "ADME-TOX profile" is defined as Absorption, Distribution, Metabolism, and Excretion (ADME) profile, combined with toxicity profile.

As used herein, "synergy" is defined as a disproportionally increased combined effect of the components A and B, exceeding the extrapolation of the individual effects of A and B produced by the assumption of additive effect. For example, when the effect of 1 mmol of A=1, of the effect of 2 mmol of B=2, the cumulative additive effect of A+B=3, a synergistic effect is observed when the observed A+B effect is greater than 3, e.g., 4, 5, 10, etc.

As used herein, "lead" is defined as a molecule demonstrating an elevated level of antineoplastic activity with IC50<100 micromoles.

As used herein, "Merrifield Resin" is a cross-linked polystyrene resin that carries a chloromethyl functional group. Merrifield resins are used in solid-phase synthesis. The material is typically available as white beads. These beads swell in suitable solvents (ethyl acetate, DMF, DMSO), which then allows the reagents to substitute the chloride substituents.

As used herein, "Inbred strains of mice" are defined as strains that have been maintained by successive brother to sister mating over more than 20 generations. Repetitive inbreeding removes genetic heterogeneity so that mice of an inbred strain are considered to be genetically identical to each other.

As used herein, "Outbred strains of mice" are defined as a strain that formed a closed population (for at least four generations) of genetically variable animals that are bred to maintain maximum heterozygosity.

As used herein, "Congenic strains" are generated by mating two inbred strains and back-crossing the descendants 5-10 generations with one of the original strains, known as the recipient strain.

As used herein, "Isogenic strains" are genetically identical, thus different individual mice of an inbred strain are isogenic. Coisogenic mice have a variant (mutation, transgene, targeted allele) that arose directly on that strain. Congenic mice have a variant larger than a gene but are otherwise isogenic.

As used herein, "cancer treatment" refers to the treatment of cell lines, murine models, non-human mammals, birds and reptiles, domestic and pet animals, and human patients. The criterion of treatment is not the improvement of the organism's well-being but the presence of anti-cancer effects induced by the inventive agents.

The present disclosure provides the 1,3-Dioxane-4,6-dione compounds of formula (I) having antitumor or anticancer properties. The following compounds are excluded: 2-[(2E)-3-[4-(dimethylamino)phenyl]-2-propen-1-ylidene]-5,5-dimethyl-; 1,3-Dioxane-4,6-dione, 2-[hydroxy[(1R,2R)-2-phenylcyclopropyl]methylene]-5,5-dimethyl-, rel-; 1,3-Dioxane-4,6-dione, 2-(1-hydroxy-3-phenylpropylidene)-5,5-dimethyl-; 2-Tert-butyl-2-methyl-5-[(E)-3-phenylprop-2-enylidene]-1,3-dioxane-4,6-dione; 5-Cinnamylidene-2,2-dimethyl-1,3-dioxane-4,6-dione; 2,2-Dimethyl-5-[3-(4-methylphenyl)-2-propenylidene]-1,3-dioxane-4,6-dione, 5-[3-Phenylallylidene]-2,2-dimethyl-[1,3]dioxane-4,6-dione, 5-[3-(4-Methylphenyl)allylidene]-2,2-dimethyl-[1,3]dioxane-4,6-dione, 5-[3-(4-Methoxyphenyl)allylidene]-2,2-dimethyl-[1,3]dioxane-4,6-dione, 5-[3-(4-Chlorophenyl)allylidene]-2,2-dimethyl[1,3]dioxane-4,6-dione, 5-[3-(4-Bromophenyl)allylidene]-2,2-dimethyl-[1,3]dioxane-4,6-dione, 5-[3-(4-Nitrophenyl)allylidene]-2,2-dimethyl-[1,3]dioxane-4,6-dione, 2,2-dimethyl-5-[3-(4-methyl-phenyl)-2-propenylidene]-1,3-dioxane-4,6-dione, and 5-[3-(4-Chlorophenyl)-2-propenylidene]-2,2-dimethyl-1,3-dioxane-4,6-dione.

One object of the present disclosure is to provide a method of producing the compounds of the formula (I), to ensure the improved binding profile to targets in a patient. The binding profile comprises the plurality of binding events with the target(s) that selectively or preferentially inhibit cancer cells while not affecting physiologically normal cells. The binding profile excludes the toxicity that arises when the undesired affinities develop to cardiac muscle ion channels and enzymes, nerve system ion channels and enzymes, mitochondria pore and enzymes, crucial metabolic enzymes. One method to establish a pool of promising leads is to generate a combinatorial library and screen it for anticancer activity. Preferred non-limiting embodiments that serve as drug development leads and that exemplify the formula (I) are shown in Table 1. The illustrative structures are numbered E1-E16, to differentiate from the numbering of the tested compounds (see Tables 5, 6).

TABLE 1

Exemplary embodiments illustrating the compound of formula (I)

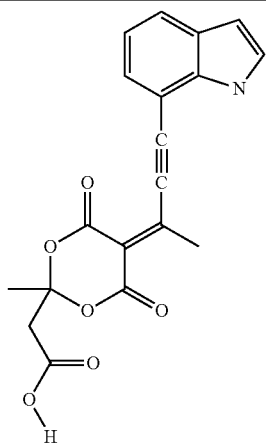

E1

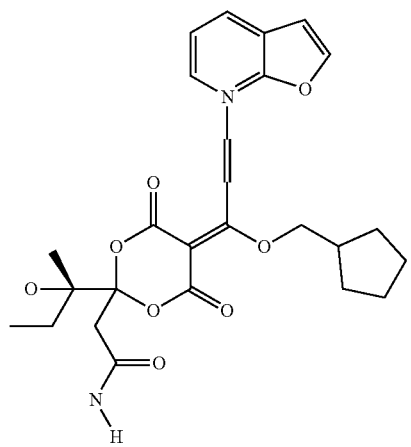

E2

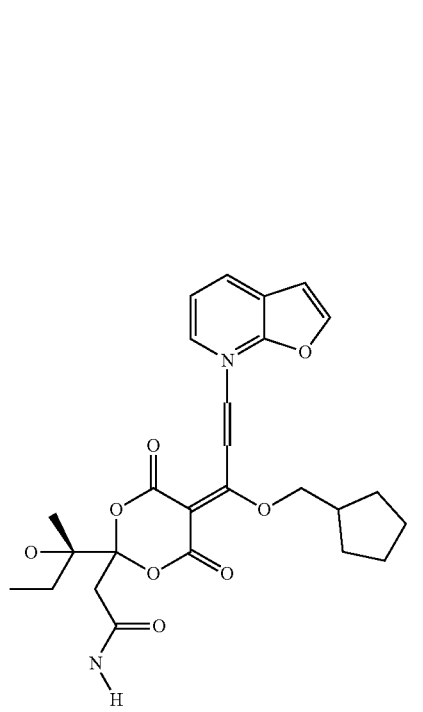

E3

TABLE 1-continued
Exemplary embodiments illustrating the compound of formula (I)
E4
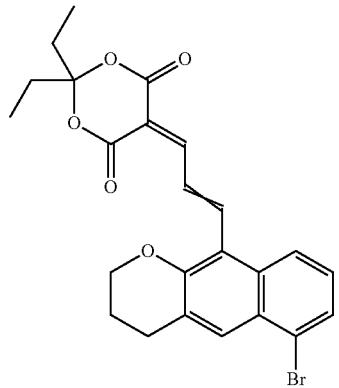 [SMILES: CCC1(CC)OC(=O)C(=CC=Cc2c3c(cc4c(Br)cccc24)CCCO3)C(=O)O1]
E5
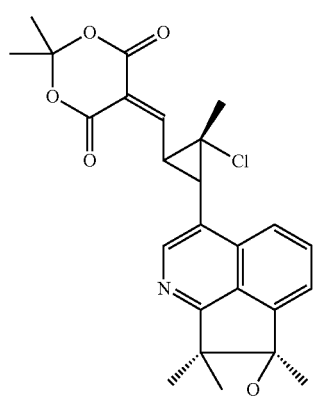
E6
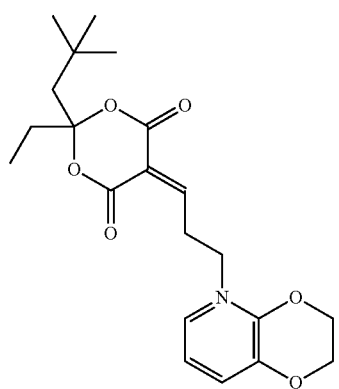
E7
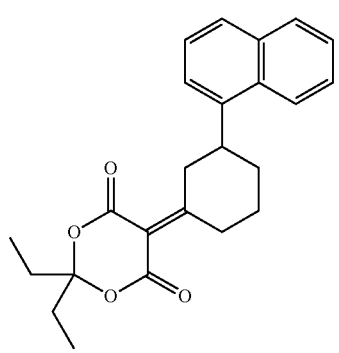 [SMILES: CCC1(CC)OC(=O)C(=C2CCCC(c3cccc4ccccc34)C2)C(=O)O1]
TABLE 1-continued
Exemplary embodiments illustrating the compound of formula (I)
E8
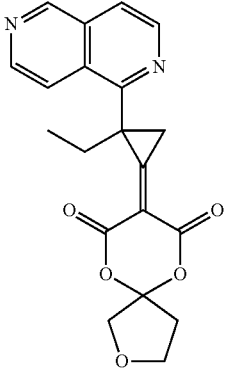
E9
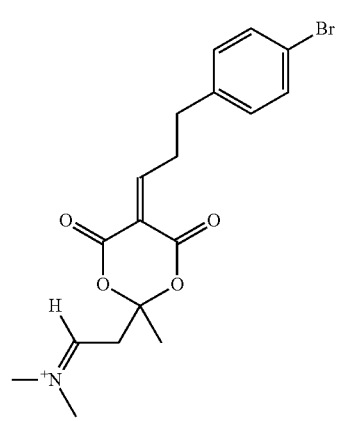 [SMILES: C[N+](C)=CCC1(C)OC(=O)C(=CCCc2ccc(Br)cc2)C(=O)O1]
E10
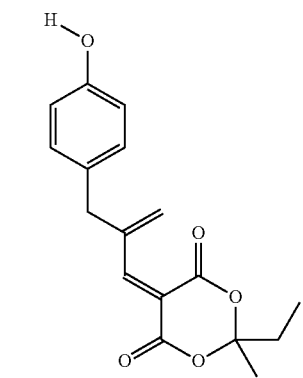 [SMILES: C=C(C=C1C(=O)OC(C)(CC)OC1=O)Cc1ccc(O)cc1]
E11
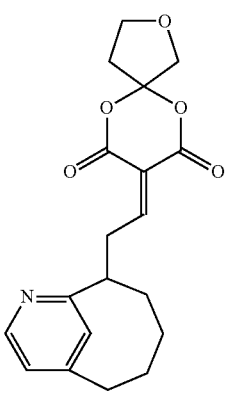 [SMILES: O=C1OC2(CCOC2)OC(=O)C1=CCC1CCCCc2ccnc1c2]

TABLE 1-continued

Exemplary embodiments illustrating the compound of formula (I)

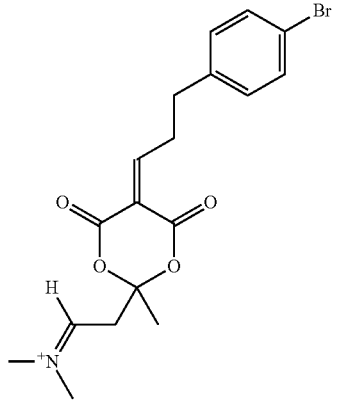 [SMILES: C[N+](C)=CCC1(C)OC(=O)C(=CCCc2ccc(Br)cc2)C(=O)O1]
E12

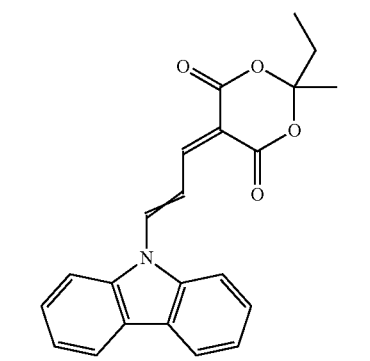 [SMILES: CCC1(C)OC(=O)C(=CC=Cn2c3ccccc3c3ccccc32)C(=O)O1]
E13

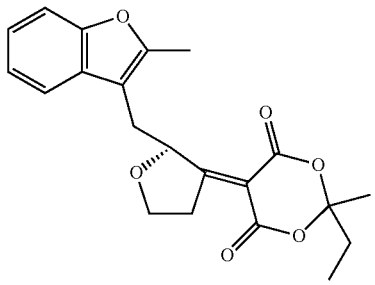 [SMILES: CCC1(C)OC(=O)C(=C2CCO[C@H]2Cc2c(C)oc3ccccc23)C(=O)O1]
E14

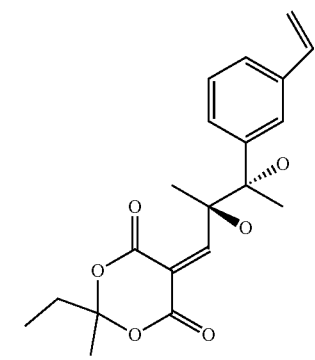 [SMILES: C=Cc1cccc([C@](C)(O)[C@](C)(O)C=C2C(=O)OC(C)(CC)OC2=O)c1]
E15

TABLE 1-continued

Exemplary embodiments illustrating the compound of formula (I)

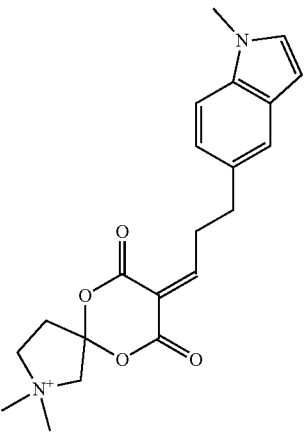 [SMILES: Cn1ccc2cc(CCC=C3C(=O)OC4(CC[N+](C)(C)C4)OC3=O)ccc21]
E16

The present disclosure further considers the methods of achieving a combinatorial diversity. The in-silico prediction of drug toxicity and the computer systems for the prediction of toxicity are incorporated herein by reference (See J. C. Dearden, *Journal of computer-aided molecular design*, 2003, v. 17(2-4), 119-27; N. Greene, *Advanced Drug Delivery Reviews,* 2002, v. 54(3), 417-31). The path to the introduction of variations is controlled by the criteria of drug-likeness such as Lipinski rule. The structures that violate multiple components of Lipinski rule are preferably not synthesized, since even in the case of high biological activity in cell culture assays, they tend to display poor ADME-TOX profile and fail clinical trials or animal tests. Compounds that violate 2-3 clauses of Lipinski rule are borderline and need an additional ADME-TOX analysis for assessment (See A. Daina, O. Michielin, V. Zoete, *Scientific reports,* 2017 v. 7, pp 42717; B. Bhhatarai, W. P. Walters, C. E. Hop, G. Lanza, S. Ekins. *Nature materials;* 2019; v. 18(5), 418, incorporated herein by reference in entirety). The compounds of formula (I) may include extensive structural variations.

The inventive compounds have a 1,3-dioxane-4,6-diones scaffold, with the numbering reflecting the oxygen and ketone positions in the 6-member ring of formula (I). The position (5) of the dioxane scaffold is substituted by an alkene group, which between the positions 7-9 of the side chain can be further substituted by an alkane, diene, alkyne, arene or other substituents. The exemplary and non-limiting substituents in the position (5) of dioxane can be termed: 5-[3-phenylpropylidene], 5-[(2E)-3-[2-(dimethylamino)phenyl]-2-propen-1-ylidene], 5-[(2E)-3-[3-(dimethylamino)phenyl]-2-propen-1-ylidene]-, 5-[(2E)-3-[5-(dimethylamino)phenyl]-2-propen-1-ylidene]-, 5-[(2E)-3-[phenyl-2-propen-1-ylidene]-, 5-[(2Z)-3-[phenyl-2-propen-1-ylidene]-, 5-[(2?)-3-[(2-naphyl)-2-propen-1-ylidene]-, 5-(3-(2-napthyl)-propylidene)-, 5-(3-(4-pyridyl)-propylidene)-, 5-(3-hydroxyindol-2-ylmethylene), 5-(phenylbutyne), 5-(1-amino-3-phenylpropylidene)-5,5-dimethyl-, 5-(1-chloro-3-phenylpropylidene)-5,5-dimethyl-, 5-(1-ethyl-3-phenylpropylidene)-5,5-dimethyl-. Of note, the compound of formula (I) allows for the geometrical isomers, E/Z isomers, enantiomers, conformers, salts, ethers, esters, amides, oligomeric and polymeric derivatives, conjugates, variable ring sizes formed by R1 and R2, immobilized forms, altered isotopic compositions of the compounds of interest. Despite the exclusion of multiple individual embodiments described in the context of synthesis, the excluded embodiments mostly pertain to the aromatic aldehydes and esters with a single phenyl ring, and not condensed or heteroaromatic systems.

Products of a method for making the compounds of formula (I) may be termed Meldrum's arylidene-condensation products. Synthetic schemes I-XVIII illustrate facile protection and deprotection with concurrent immobilization and detachment (see FIGS. 1 and 2). The synthetic path may include Knoevenagel condensation of Meldrum's acid with aromatic aldehydes (also see U. Desai et al. in *An International Journal for Rapid Communication of Synthetic Organic Chemistry*, 2004, Volume 34, Issue 1; H. S. Sandhu, S. Sapra, M. Gupta, et al., in *Bioorg Med Chem*, 2010, 18(15):5626-33, incorporated herein by reference in entirety).

Meldrum's acid and derivatives are used in the preparation of arylidene-condensation products. Meldrum's acid is another name for the family of 1,3-dioxane-4,6-diones, which form a stabilized conjugated anion after deprotonation. The nucleophilic carbo-anion site attacks the electrophilic position on the carbonyl carbon of aromatic aldehydes, and under the conditions of Lewis acidity, and high temperature, the resulting hydroxyl (former aldehyde oxygen) is eliminated, producing the alkene bond adjacent to the dioxane ring, see Scheme I.

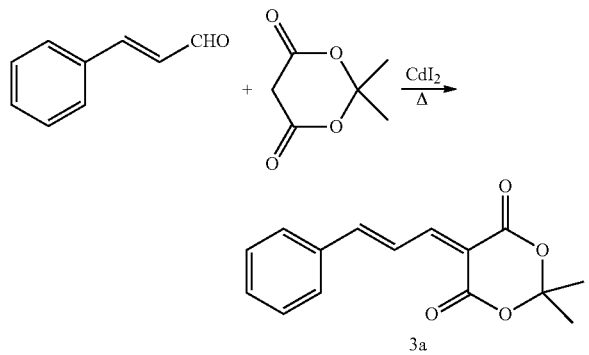

Scheme 1: Optional CdI$_2$ in place of a base and a solvent

A synthetic procedure may include using a mixture of equimolar amounts of aryl aldehyde and Meldrum's acid and heating at reflux in 2-ethoxyethanol with catalytic amounts of triethylamine. The product preferably includes a 3-phenylpropylidene Meldrum's acid derivative (Scheme 1). The reaction yield may be increased by using a molar ratio 1:2 of aldehyde and Meldrum's acid. One exemplary set of specific conditions, without limitation is: a solution of cinnamaldehyde (2.0 mmoles) and Meldrum's acid (4.0 mmoles) in 5 ml of 2-ethoxyethanol and catalytic amounts of triethylamine refluxed during 5-30 minutes (TLC control), after cooling the resulting precipitate is filtered, washed with ethanol, dried and purified by column chromatography on silica-gel and chloroform as eluent.

In another embodiment, the synthetic method comprises water solvent and HTMAB (hexadecyltrimethylammonium bromide) as a catalyst and leads to the synthesis of 5-aryl-methylene-2,2-dimethyl-1,3-dioxane-4,6-diones. For example, 4-dimethylaminobenzaldehyde reacted with isopropylidene malonate in the presence of 0 mol. % HTMAB to give the product in quantitative yield (66%) after 30 minutes reaction at 60° C. Increasing the catalyst to 5, 10, and 15 mol. % results in improved reaction yields to 76%, 92%, and 92% respectively, with 10 mol. % HTMAB chosen as a quantitative catalyst for these reactions. The duration of 30 minutes is the best condition for the reactions.

In still another embodiment a mixture of Meldrum's acid (20 mmol) and the corresponding aromatic aldehyde (20 mmol) is dissolved in acetonitrile (20 mL), while piperidine (0.1 mL) is added. The resulting solution is stirred at room temperature for 10 h. Afterward, it is poured into ice-water, and the precipitate is collected by filtration. Further purification is accomplished by recrystallization from ethanol.

Another embodiment utilizes an ionic liquid ethylammonium nitrate (EAN)-promoted Knoevenagel condensation of Meldrum's acid with an aromatic aldehyde. Meldrum's acid 1 (2 mmol) and aromatic aldehyde 2 (2 mmol) are dissolved in ionic liquid EAN (2 ml). The reaction mixture is stirred at room temperature for 0.5 to 2 h, and the reaction is monitored by TLC. Upon completion of the reaction, all the insoluble material in the reaction mixture is filtered and washed with water to give the desired products in high yields with essential purity. After isolation of the product, the remainder of the ionic liquids ENA is dried for 4 h under vacuum at 50° C. In a variant of the synthesis, the reactions involving Meldrum's acid and an aldehyde proceeds as a Knoevenagel reaction in the presence of EDDA (Ethylene Diammonium Acetate). As another strategy basic alumina can be used to promote Knoevengel condensation of Meldrum's acid with an aromatic aldehyde.

Meldrum's acid can be produced by a condensation reaction of acetone with malonic acid in acetic anhydride and sulfuric acid. The amount of sulfuric acid is catalytic, and the reaction proceeds at room temperature over 24 hours (See A. Meldrum in *Journal of the Chemical Society, Transactions*, 1908, v. 93, pp 598-601, incorporated herein by reference in entirety)

Scheme II

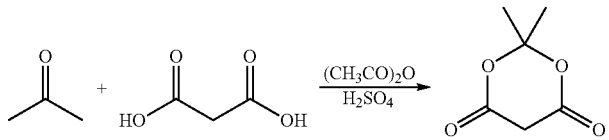

-continued

Scheme III

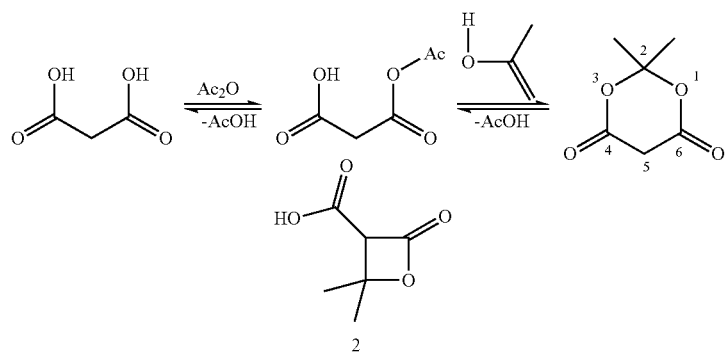

In Scheme III, the attack of the malonic acid OH group on the electrophilic center in Ac$_2$O carbonyl produces an acetylated malonate oxygen which may act as a leaving group.

The second malonate hydroxy oxygen attacks the electrophilic carbon of acetone (in the enolic form), inducing nucleophilic character on the acetone's oxygen. The nucleophilic acetone oxygen attacks the first malonic carbonyl, eliminating the previously formed acetate and closing the ring forming the product (1) of the Scheme III. Abstraction of a proton produces a stabilized malonic —CH— carboanion (position 5 in the 4.6-dione ring of the Scheme III), that is inhibited in the sulfuric acid environment but is still partially present. The nucleophilic central carbon (2) of the malonate moiety attacks the electrophilic acetone carbonyl carbon, induces a negative charge on the acetone oxygen, and displaces the acetate (—O—Ac) group from malonate, forming an alternative side reaction product (2). Maintaining acidity is essential to favor the major product route (Scheme III).

Meldrum's acid is commercially available see: Acadechem, ABBLIS Chemicals, Life Chemicals, Key Organics/BIONET, Glentham Life Sciences Ltd., Acros Organics, Yuhao Chemical, Ambeed, CAPOT, King Scientific, Biosynth, Pi Chemicals, eNovation Chemicals, Tractus, ChemSpace.com Database, Finetech Industry Limited, Achemtek, VladaChem, Acorn PharmaTech Product List, Aurora Fine Chemicals LLC, Wolves R&D chemical, Activate Scientific, Mcule, VWR, Part of Avantor, Accela ChemBio Inc., TripleBond, Combi-Blocks, Apexmol, ChemShuttle, Aromalake Chemical, MuseChem, Alfa Aesar, AKos Consulting & Solutions, Norris Pharm, AHH Chemical co., ltd, labseeker, Aurum Pharmatech LLC, Alichem, 3B Scientific (Wuhan) Corp, abcr GmbH.

In a preferred embodiment, the Meldrum's acid compounds are synthesized using a diethyl, di-propyl, di-isopropyl, di-butyl, di-sec-butyl, cycloalkyl ketones. The alpha, beta, gamma, and the more distal positions vs. the ketone carbonyl can be substituted by alkyls, ethers, cycloalkyls, and aryls, or any other groups.

Another component for use in Scheme I is an aromatic aldehyde such as toluene, ylene, styrene, pyridine, Pyrazine, 2-Methoxy-5-methylpyrazine, Pyrimidine, Imidazole, Furan, Pyrrole, Oxazole, Isoxazole, Anethole, Naphthalene, Anthracene, Quinoline, Isoquinoline, Quinoxaline, Quinazoline, Cinnoline, Phthalazine, Acridine, Benzothiazole, Benzisoxazole, Benzoxazole, Indazole, Benzimidazole, Purine, Benzo[c]thiophene, Benzothiophene, Indole, Isoindole, Benzofuran, Isobenzofuran, Phenanthrene, Phenalene, Bi-phenyl, ortho-Phenanthroline, the isomers and substituted forms of the above. The structural variations include the positions of heteroatoms within the rings and the substitutions by alkyls, alkenes, cycloalkyls, aryls, terpenes, adamantanes, heteroaryls, ethers, esters, amides, keto groups, nitrates, sulfoxides, sulfonamides, mentioned only as a non-limiting example.

An aldehyde group can be introduced in the position 9 of the linker L of formula (I). Preferably the side chain of a precursor aldehyde is 3 bonds between the aromatic system and carbonyl carbon (e.g., the aldehyde side chain C3). While shown as an alkene on the aldehyde component in Scheme I, the C3 aldehyde side chain can be an alkene, alkyne, or a cycloalkyl. The conversion of the alkene bond on the C3 into an alkane, alkyne, or a cycloalkyl is within the scope of the present disclosure, but the preferred embodiments incorporate the semi-product with the already formed linker in this position, to avoid modifying the final labile product typically present in a small amount, just sufficient for testing and identification.

TABLE 2 the exemplary aromatic and hetero-aromatic aldehyde structures available through Enamine and suitable for the reactive Scheme I. The aldehyde-bearing side chain of the aromatic ring is C3 long and can be an alkane, alkene, alkyne or cycloalkyl.

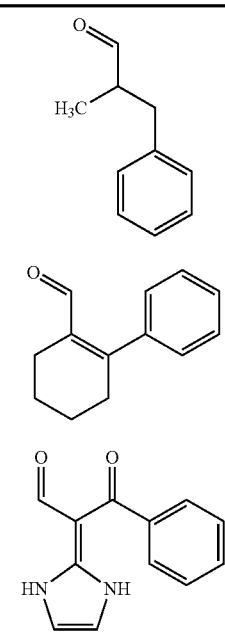

TABLE 2-continued
the exemplary aromatic and hetero-aromatic aldehyde structures available through Enamine and suitable for the reactive Scheme I. The aldehyde-bearing side chain of the aromatic ring is C3 long and can be an alkane, alkene, alkyne or cycloalkyl.
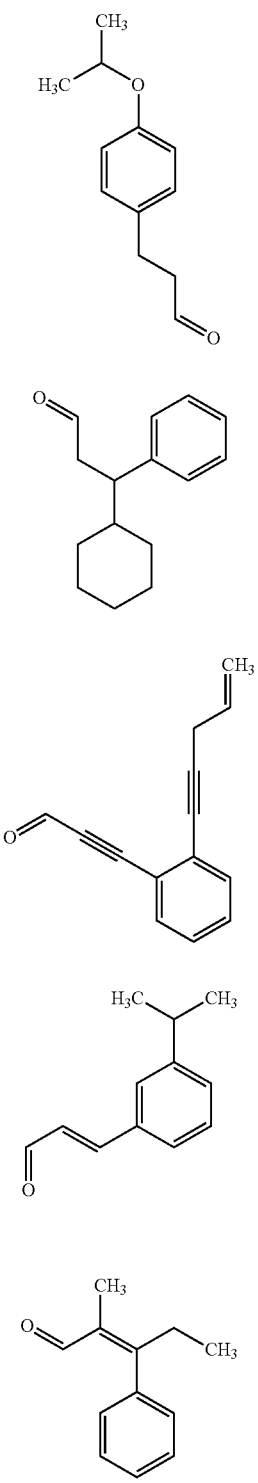
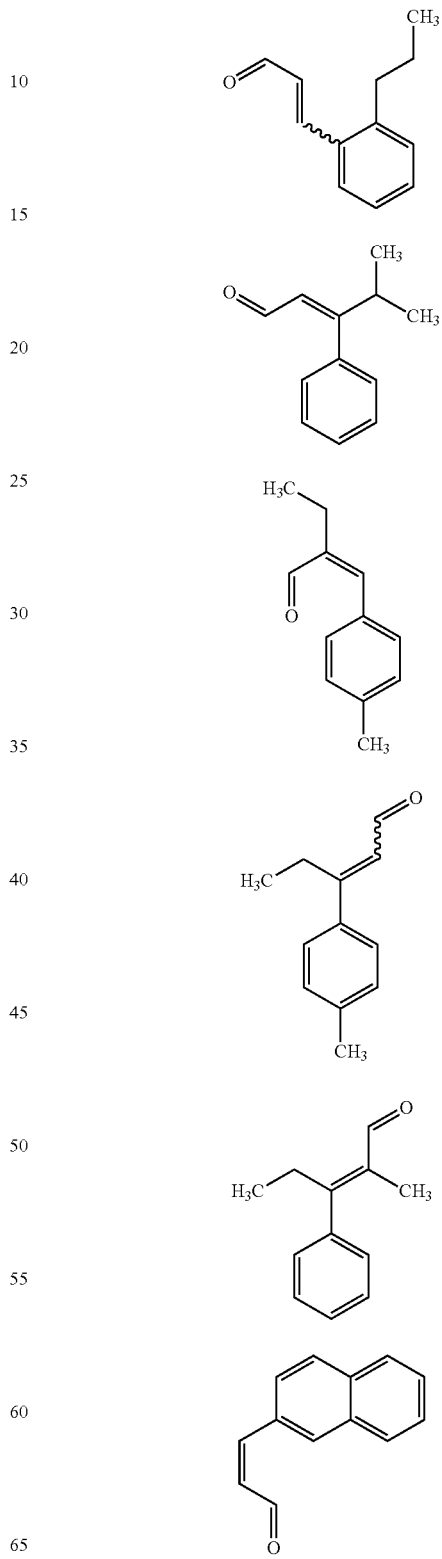

TABLE 2-continued
the exemplary aromatic and hetero-aromatic aldehyde structures available through Enamine and suitable for the reactive Scheme I. The aldehyde-bearing side chain of the aromatic ring is C3 long and can be an alkane, alkene, alkyne or cycloalkyl.
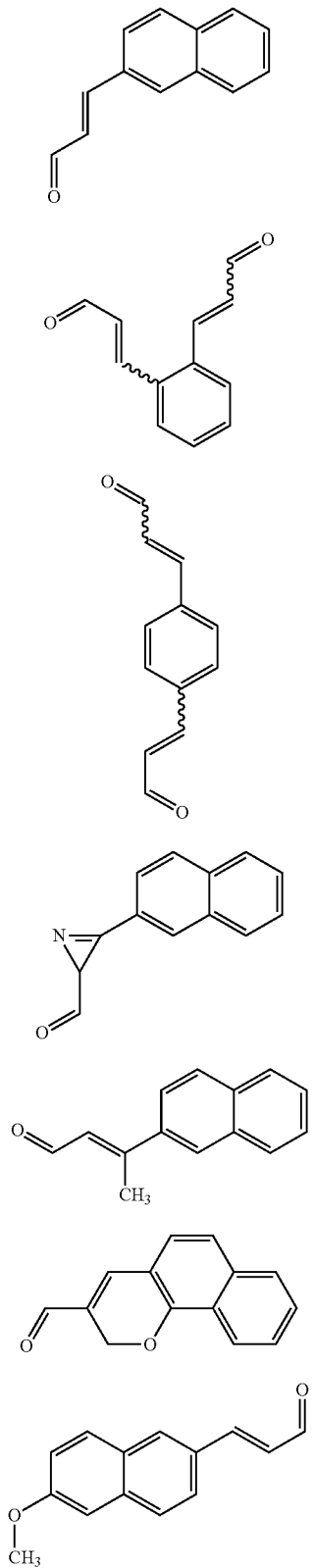
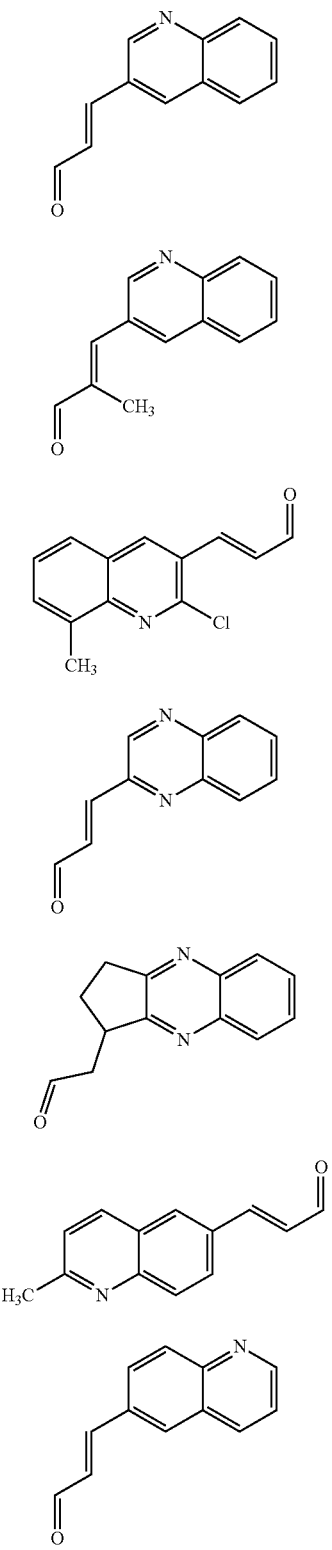

TABLE 2-continued the exemplary aromatic and hetero-aromatic aldehyde structures available through Enamine and suitable for the reactive Scheme I. The aldehyde-bearing side chain of the aromatic ring is C3 long and can be an alkane, alkene, alkyne or cycloalkyl.

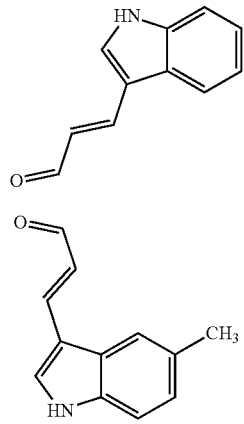

In an alternative embodiment, the aldehydes are C1 or C2 in terms of the spacing between the aromatic system and the aldehyde carbonyl, counted in the same manner, as shown in Table 2. These structures are extended to produce the C3 spacing by gentle synthetic methods compatible with greater lability of heteroaromatic rings as compared to benzene, naphthalene, or polyaromatic hydrocarbons (PAH). Since a greater diversity of aldehyde structures is available with the C1-C3 spacing as compared to the C3 spacing only, the extension of the side chain with the terminal aldehyde group is a useful path to introduce more combinatorial diversity. A preferred method of aldehyde chain extension is aldol condensation with acetaldehyde. Lithium diisopropylamide (commonly abbreviated LDA) is a chemical compound with the molecular formula $[(CH_3)_2CH]_2NLi$. LDA is used as a strong base and has been widely accepted due to its good solubility in non-polar organic solvents and non-nucleophilic nature, stemming from the steric blockade of the nitrogen electron pair by the isopropyl groups, allowing proton access but preventing the formation of covalent bonds by the blocked orbital. Equimolar LDA and acetaldehyde are reacted in tetrahydrofuran solvent at −78° C., forming enolate. The aldehyde(s) of interest are added dropwise to the enolate solution to reach the final 1:1 molar ratio between the enolate and the aldehyde carbonyls. After neutralization and reflux at the pH=3-4, the beta-hydroxyl positions (counted vs. the newly incorporated carbonyl, formerly originating from the acetaldehyde) eliminate a water molecule and produce an α,β-unsaturated carbonyl compound. For example, benzaldehyde is a precursor for cinnamic aldehyde when reacted with acetaldehyde by the enolate-directed mechanism. The combinatorial plurality of the aromatic aldehydes may be termed an "aldehyde library".

The alkene moiety of the aldehyde C3 linker can be selectively reduced in the presence of carbonyl and aromatic rings. Such selective conditions are described in F.-X. Felpin, E. Fouquet, Chem. Eur. J., 2010, 12440-12445; A. Mori, Y. Miyakawa, E. Ohashi, T. Haga, T. Maegawa, H. Sajiki, Org. Lett., 2006, 8, 3279-3281; T. Ikawa, H. Sajiki, K. Hirota, Tetrahedron, 2005, 61, 2217-2231; J. M. Brunel, Synlett, 2007, 330-332; Y. Wang, A. Kostenko, S. Yao, M. Driess, J. Am. Chem. Soc., 2017, 139, 13499-13506, incorporated herein by reference in entirety;

The conversion of alkenes to epoxides in the presence of aromatic and aldehyde groups is preferably mediated by 2,2,2-trifluoroacetophenone as an efficient catalyst for a cheap, mild, fast, and environmentally friendly epoxidation of alkenes. Various olefins, mono-, di-, and trisubstituted, are epoxidized selectively in high to quantitative yields utilizing low catalyst loadings and $H_2O_2$ as a green oxidant (See: D. Limniois, C. G. Kokotos, J. Org. Chem., 2014, v. 79, 4270-4276, incorporated herein by reference in entirety.

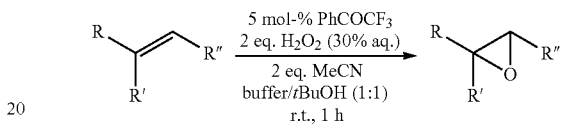

R: alkyl, Ar, H, COR″
R′: alkyl, H
R″: alkyl, H
buffer: 0.6M, $K_2CO_3$, $4\times10^{-5}$M EDTA tetrasodium salt In a preferred non-limiting embodiment, the reactions between the malonate and the list of ketone precursors are conducted individually. The conditions for Meldrum's condensation are mild, and the reaction proceeds by incubation at room temperature, with relatively non-toxic solvents ($Ac_2O$, $H_2SO_4$). After completion, the acidic content of the wells evaporates at room temperature in the slow stream of inert gas. Acetic anhydride boils at 139.8° C. with the vapor pressure of 4 mm Hg at 20° C. Meldrum's acid's melting point is 94° C., and it decomposes in the process. Partial loss of the final product is observed during the process of acetic anhydride distillation, however, the melting point of acetic anhydride is −73° C. indicating lower intermolecular bonding energy than in Meldrum's acid. The difference is increasing with the increasing molecular weight of the groups $R_1$ and $R_2$ of the compound of formula I. With greater melting temperatures, the boiling temperature difference also increases, and the separation between the unreacted acetic anhydride and reaction products is feasible.

After distillation of the first step solvent, the contents of the wells are re-dissolved in the second step solvent, disclosed above. In one embodiment, the second solvent is ethoxyethanol and triethanolamine. In an alternative embodiment, the second solvent is 90% water and 10% HTMAB (hexadecyltrimethylammonium bromide). In still another embodiment, the second solvent is acetonitrile (20 mL) and piperidine (0.1 mL). Yet another embodiment discloses organic reactions in ionic liquids, specifically ionic liquid ethylammonium nitrate (EAN). The water/HTMAB is the most preferred embodiment, allowing the reaction to proceed at room temperature, however not all aromatic aldehydes are water-dissolvable, and therefore all variations of the second step listed above are suitable and can be selected based on routine experimentation by those skilled in the art.

The residual acidity that is still present in the reaction wells diminishes the yield of the second step reaction, depending on the presence of nitrogenous bases as catalysts. An excess of the nitrogen bases is added to neutralize the residual acidity, and the progress of the neutralization is spectroscopically monitored in each well by adding a non-interfering quantity of an acid-base indicator with the second solvent. The outlier wells are corrected manually by adding the pre-computed quantity of the nitrogen base catalyst. After establishing the optimal reaction conditions, the concentrated stock solution of the target aromatic aldehydes is delivered to each well, and wells are incubated with periodic spectroscopic monitoring until the spectral pattern stabilizes, indicating the end of the reaction. The incubation method comprises 4-6 electric hotplates at minimal power production, initially wiped by alcohol and covered by a thick metal sheet or a sand-bath with the metal trays with the 96-well plates stationed above. The metal sheet or sand-bath radiates the heat received from the hotplates, delivering only a fraction to the plates. The temperature profile is controlled in several places, and an even distribution of the temperature in the working range is controlled along the heating surface. The heating takes place under an inert gas flow in a sterile hood and the hotplates are treated by a disinfectant (alcohol) before turning the heat while already under the inert gas.

Several positions on a well plate should remain blank, producing a solvent control. The need in such a control arises from possible toxicity of the reaction solvent components to the downstream assay cell culture. The control allows adjusting the injected volumes of the reaction mixes in the assay wells such that no statistically significant inhibitory effect is detected. While the reactions take place under the flow of sterile inert gas and can be considered aseptic, the assay cultures would still require the presence of a dual antibiotic and antimycotic agent, to prevent the artifacts related to accidental contamination. A shortened time of incubation (6-8 h) is recommended for the assay stage to minimize the possibility of contamination. The increased turbidity of the contaminated wells is easily detectable by the plate scanner, and the promising experiments indicating anti-cancer activity are repeated with more stringent contamination and solvent controls. The same lead is tested in several replicates, to ensure that the testing information is not lost due to the loss of a specific data point due to any of the factors.

In another preferred embodiment, the synthesis of a liquid-phase library is performed in a single reactor by a two-step protocol with changing solvent. In this scheme, the ketone library and the malonate of the Meldrum's reaction step are first mixed in acetic anhydride with the addition of the catalytic quantity of $H_2SO_4$, the reaction is incubated for 24 hours, and the solvents are distilled in a rotary vacuum evaporator. The non-volatile residue comprises a plurality of Meldrum's products carrying the structural variations traced to the parent ketones. The inevitable side-products, residual solvent, and sulfuric acid also remain in the reactor. The contents are dissolved in the second solvent intended for the reaction between the Meldrum's products and aromatic aldehydes. The second solvent comprises an excess of amine catalyst sufficing to neutralize the excessive residual acidity. The aldehydes are dissolved as stock solutions and are added together to the second solvent, reacting with the Meldrum's products by one of the above-described schemes described in the multi-well plate library embodiment.

After completion of the reaction, the second solvent is evaporated under vacuum, and the products are dissolved in the carrier solvent system intended for a preparative High-Performance Liquid Chromatography (HPLC). The providers of suitable preparative systems are AZURA Prep LC, Termo-Fisher Scientific, JASCO, KNAUER, Labcompare, Preparative Chroma Columns, YMC Co., PHENOMENEX. The separated fractions are collected in the containers identified by coupling with the detection process, and the purest and concentrated fractions are the most suitable for the downstream assay testing. The purity can be assessed from the shape of the neighboring peaks allowing to extrapolate the composition overlap. The number of the compounds synthesized in a single batch is determined by the downstream processing efficiency and in the most preferred version of the embodiment, the synthesis and testing are provided concurrently, immediately directing the fractions to the tests and freezing the rest for the post-testing spectroscopic, structural identification by the methods known to those skilled in the art (infrared spectroscopy, ultraviolet spectroscopy, mass-spectroscopy, nuclear magnetic resonance without limiting)

Figure 2:
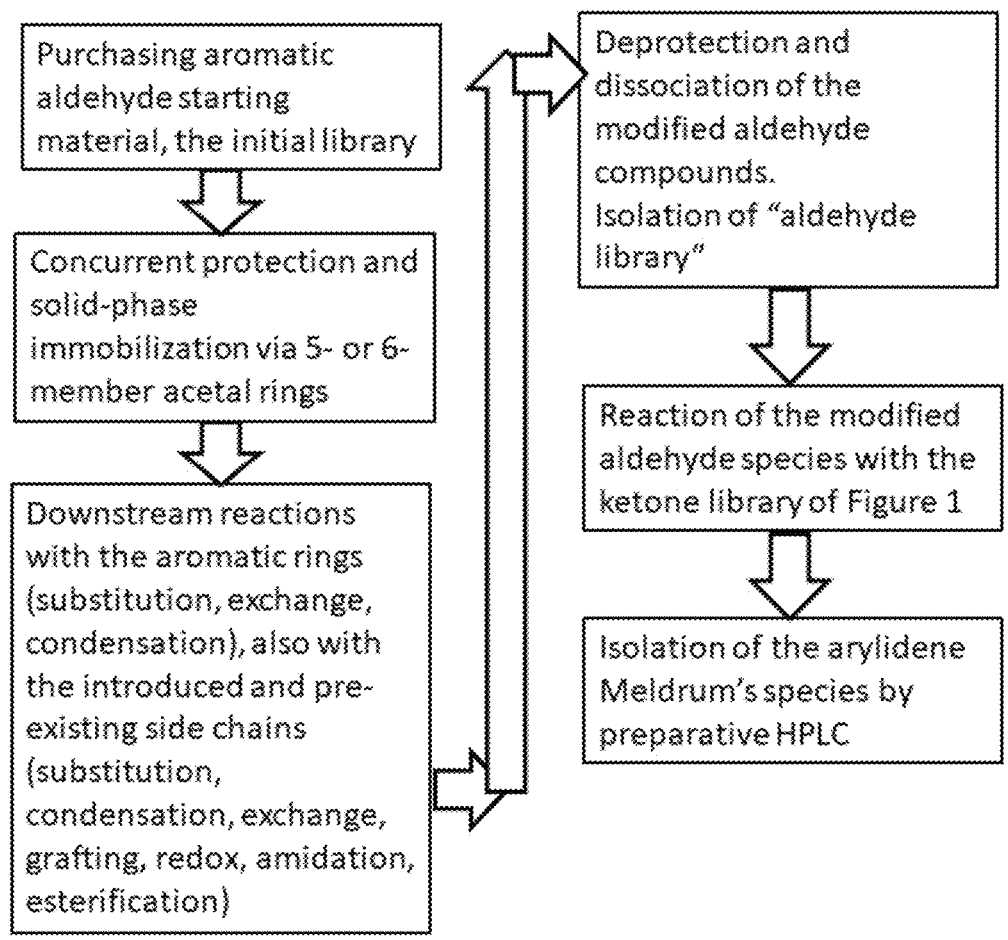
FIG. 2 shows a flow chart for a process of reacting ketone and aldehyde components to form a combinatorial library.

In a more preferred embodiment, the aldehyde library is not reacted with the Meldrum's ketone library products immediately (FIGS. 1 and 2). Instead, the library is reversibly bound to a solid support through the protection of the aldehyde groups. The aromatic moieties are substituted and expanded by combinatorial chemistry, the resulting expanded aldehyde library is detached from the solid support with the deprotection of aldehyde reactivity and the restored expanded aldehyde library is reacted with the Meldrum's ketone library products in a single reactor (See FIGS. 1 and 2). The products are separated by the preparative HPLC with the subsequent spectroscopic identification of the frozen fractions. The challenge of this approach is to produce reliable and reversible immobilization compatible with multiple reaction steps expanding the combinational complexity, with none of them leading to premature dissociation of the expanding lead from the solid phase support. Such schemes of aldehyde protection and immobilization are combined in Table 3 (See T. W. Green, P. G. M. Wuts, *Protective Groups in Organic Synthesis*, Wiley-Interscience, New York, 1999, 297-304, 724-727; T. W. Green, P. G. M. Wuts, *Protective Groups in Organic Synthesis*, Wiley-Interscience, New York, 1999, 329-344, 724-727; T. W. Green, P. G. M. Wuts, *Protective Groups in Organic Synthesis*, Wiley-Interscience, New York, 1999, 350-352, 724-727, incorporate herein by reference in entirety)

TABLE 3

The conditions for stable protection and deprotection of aldehyde groups.
The conditions leading to loss of stability are indicated in bold, underlined, and italicized fonts.

Protection by 1.3-dioxanes or by 1.3-dioxolanes

| | | | | | | |
|---|---|---|---|---|---|---|
| H₂O: | *__pH < 1, 100° C.__* | *__pH = 1, RT__* | pH = 4, RT | pH = 9, RT | pH = 12, RT | pH > 12, 100° C. |
| Bases: | LDA | NEt₃, Py | t-BuOK | Others: | DCC | SOCl₂ |
| Nucleophiles: | RLi | RMgX | RCuLi | Enolates | NH₃, RNH₂ | NaOCH₃ |
| Electrophiles: | RCOCl | RCHO | CH₃I | Others: | :CCl₂ | Bu₃SnH |
| Reduction: | H₂/Ni | H₂/Rh | *__Zn/HCl__* | Na/NH₃ | LiAlH₄ | NaBH₄ |
| Oxidation: | KMnO₄ | OsO₄ | CrO₃/Py | RCOOOH | Cl₂, Br₂, I₂ | MnO₂/CH₂Cl₂ |

Protection by 1,3-Dithianes or by 1,3-Dithiolanes

| | | | | | | |
|---|---|---|---|---|---|---|
| H₂O: | *__pH < 1, 100° C.__* | pH = 1, RT | pH = 4, RT | pH = 9, RT | pH = 12, RT | pH > 12, 100° C. |
| Bases: | LDA | NEt₃, Py | t-BuOK | Others: | DCC | SOCl₂ |
| Nucleophiles: | RLi | RMgX | RCuLi | Enolates | NH₃, RNH₂ | NaOCH₃ |
| Electrophiles: | RCOCl | RCHO | *__CH₃I__* | Others: | :CCl₂ | Bu₃SnH |
| Reduction: | *__H₂/Ni__* | *__H₂/Rh__* | Zn/HCl | *__Na/NH₃__* | LiAlH₄ | NaBH₄ |
| Oxidation: | *__KMnO₄__* | OsO₄ | CrO₃/Py | *__RCOOOH__* | *__Cl₂, Br₂, I₂__* | MnO₂/CH₂Cl₂ |

Protection by N,N-Dimethylhydrazone

| | | | | | | |
|---|---|---|---|---|---|---|
| H₂O: | *__pH < 1, 100° C.__* | pH = 1, RT | pH = 4, RT | pH = 9, RT | pH = 12, RT | *__pH > 12, 100° C.__* |
| Bases: | *__LDA__* | NEt₃, Py | t-BuOK | Others: | DCC | SOCl₂ |
| Nucleophiles: | RLi | RMgX | RCuLi | Enolates | *__NH₃, RNH₂__* | NaOCH₃ |
| Electrophiles: | RCOCl | RCHO | *__CH₃I__* | Others: | *__:CCl₂__* | Bu₃SnH |
| Reduction: | *__H₂/Ni__* | *__H₂/Rh__* | *__Zn/HCl__* | Na/NH₃ | *__LiAlH₄__* | NaBH₄ |
| Oxidation: | *__KMnO₄__* | OsO₄ | *__CrO₃/Py__* | *__RCOOOH__* | *__Cl₂, Br₂, I₂__* | MnO₂/CH₂Cl₂ |

The analysis of Table 3 points to cyclic 1,3-diols as the most versatile protectants, compatible with the greatest variety of the downstream reactions. Resin beads or gels modified by 1,3-propylenglycol or 1,2-ethylenglycol produce the starting material for reacting with the protected aldehyde group. One non-limiting example of such material are HypoGel® Diol Resins and TentaGel® Diol Resins by Rapp Polymere. A range of alkyl spacer-tethered 1,2- and 1,3-diols have been prepared from commercially available Merrifield resin and (4-chloromethyl)phenylpentyl-polystyrene-co-divinylbenzene, as described in "*The synthesis of catalytic application of spacer modified diol-functionalized Merrifield resins*" in *Cheminform* 2005, v. 46(28): 4753-4756 by P. Dyer et. al., incorporated herein by reference in entirety. The synthetic path is illustrated in Scheme IV:

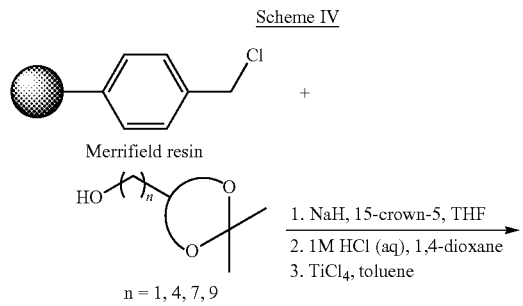

The modified Merrifield resin is applied as both the solid support and protection for the aromatic aldehyde library of the invention by forming 5-member or 6-member cyclic acetals. An exemplary and non-limiting synthetic protocol by J. Dong, L. Yu, and J. Xie titled "*A Simple and Versatile Method for the Formation of Acetals/Ketals Using Trace Conventional Acids*" is published in *ACS Omega*, 2018, v. 3, pp 4974-4985 and is incorporated herein by reference in entirety. Specifically, a mixture of aldehyde 1 (0.3 mmol) and 0.1 mol % hydrochloric acid in methanol (4 mL) is stirred at ambient temperature for 30 min. Then 0.15 mol % NaHCO₃ is added and stirred for a few minutes. After that, the organic layer is concentrated in vacuo, and column purification on silica gel is performed using hexane-ethyl acetate in 1% triethylamine to obtain the product. The reported yields are in the range between about 90% and 99% for acetal conversion of diverse aldehydes, including bridged, aromatic, and heteroaromatic species. The liquid phase procedure can be easily adapted to a solid phase modification by the methods known to those skilled in the art, such as centrifugation and washing of the solid phase. The end-product of this step is the surface-modified Merrifield resin, with the immobilized aromatic residue library of compound of formula (I) linked to the support by the stable 5- or 6-member cyclic acetal connectors.

In another preferred embodiment, 1,3-Dioxanes and 1,3-dioxolanes can easily be prepared from carbonyl compounds with the Merrifield resin-immobilized 1,3-propanediol or 1,2-ethanediol in the presence of a Brönsted or a Lewis acid catalyst. 1,3-Diols give more stable compounds than 1,2-diols. A standard procedure for protection employs toluene-sulfonic acid as a catalyst in refluxing toluene, which allows the continuous removal of water from the reaction mixture using a Dean-Stark apparatus. A mixture of orthoesters or molecular sieves can also provide effective water removal through chemical reaction or physical sequestration.

Scheme V

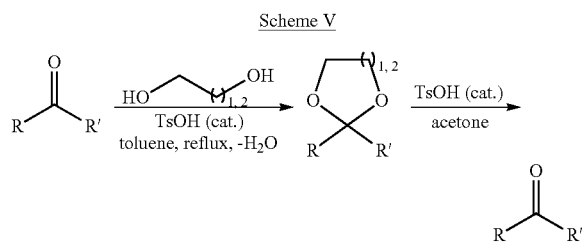

Cyclic acetals offer stability against all types of nucleophiles and bases. Cyclic ketals and acetals, as a rule, are stable to mild high-valent chromium reagents (PCC, PDC, Jones), but strongly acidic reagents oxidize them to the lactone, or related cleavage products. The addition of strong Lewis acids enhances the sensitivity towards oxidants such as KMnO4, and MCPBA. These conditions should be avoided for downstream reactions.

In another preferred embodiment, acyclic and cyclic acetals of various carbonyl compounds are obtained in excellent yields in the presence of trialkyl orthoformate and a catalytic amount of tetrabutylammonium tribromide in absolute alcohol.

Scheme VI

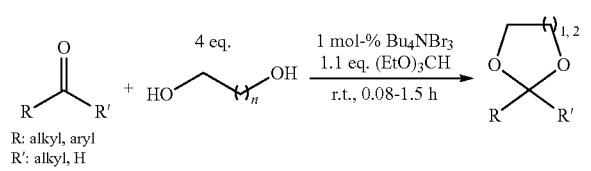

R: alkyl, aryl
R': alkyl, H

This convenient, mild, selective method allows acetalization of an aldehyde in the presence of ketone, unsymmetrical acetal formation, and tolerates acid-sensitive protecting groups (See: R. Gopinath, Sk. J. Hague, B. K. Patel, *J. Org. Chem.*, 2002, v. 67, 5842-5845, incorporated herein by reference in entirety). Like in Scheme V, the diol component is immobilized on the Merrifield matrix.

In another preferred embodiment, zirconium tetrachloride (ZrCl4) is a highly efficient and chemoselective catalyst for the acetalization, and in situ transacetalization of carbonyl compounds under mild reaction conditions.

Scheme VII

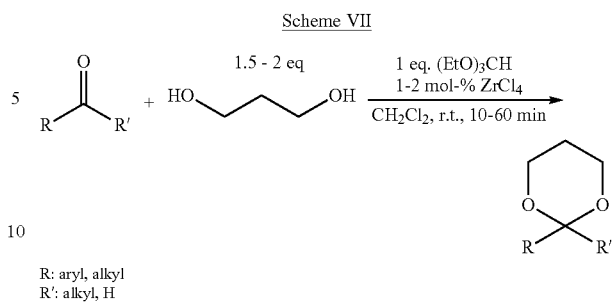

R: aryl, alkyl
R': alkyl, H

See: H. Firouzabadi, N. Iranpoor, B. Karimi, *Synlett*, 1999, 321-323, incorporated herein by reference in entirety.

Yet other preferred embodiments include:

the use of 1,3-bis(trimethylsiloxy)propane (BTSP) and a catalytic amount of iodine under essentially neutral aprotic condition. (See: B. Karimi, B. Golshani, Synthesis, 2002, 784-788);

a photochemical method for acetalization of aldehydes under low-energy visible light irradiation, whereby a broad range of aromatic, heteroaromatic, and aliphatic aldehydes are protected under neutral conditions in good to excellent yields using a catalytic amount of Eosin Y as the photocatalyst. The challenging acid-sensitive aldehydes and sterically hindered aldehydes are converted, while ketones remain intact (See: H. Yi, L. Niu, S. Wang, T. Liu, A. K. Singh, A. Lei, *Org. Lett.*, 2017, 19, 122-125);

a hydroxy acetophenone conversion into the corresponding cyclic acetals in the presence of a diol, triisopropyl orthoformate, and a catalytic amount of cerium(III) trifluoromethanesulfonate under mild reaction conditions. (See F. Ono, H. Takenaka, T. Fujikawa, M. Mori, T. Sato, *Synthesis*, 2009, 1318-1322);

aliphatic and aromatic ketones converting into their corresponding α-chloroketone acetals in very good yields using iodobenzene dichloride in ethylene glycol in the presence of 4 Å molecular sieves at room temperature (See: J. Yu, C. Zhang, *Synthesis*, 2009, 2324-232).

Schemes VIII-XI illustrate examples of steps of the method:

Scheme VIII

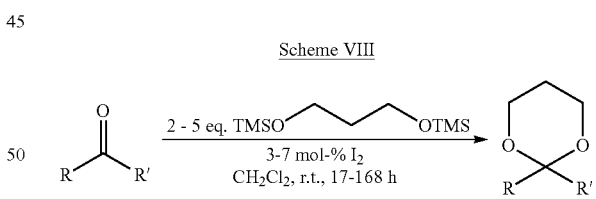

Scheme IX

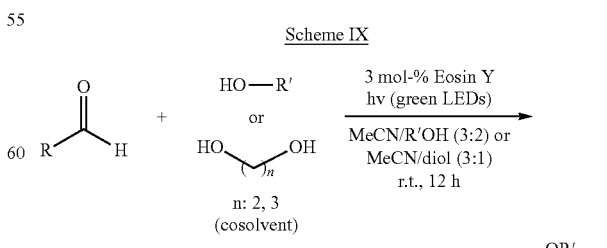

n: 2, 3
(cosolvent)

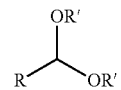

Scheme X

R: Ar, alkyl
R': alkyl

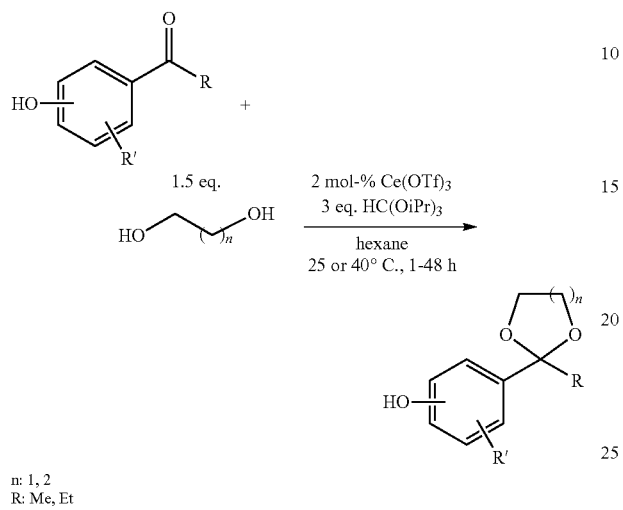

n: 1, 2
R: Me, Et

Scheme XI

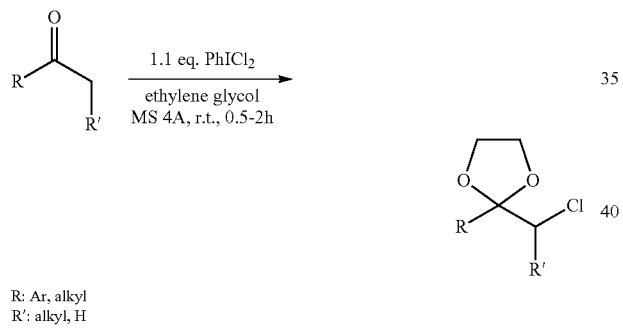

R: Ar, alkyl
R': alkyl, H

The modified resin next is placed in the downstream reaction conditions. The downstream reactions comprise without limitation electrophilic substitution, nucleophilic substitution, oxidations, reductions, additions, cycloadditions, epoxidation, acylation, amide formation, thiol formation, alkyne bond incorporation, diazonium salt formation, Wittig reactions, aldol-condensation, dismutations, click chemistry, diene-dienophile conjugations, 1,4-carbonyl system additions. The range of downstream reactivity is limited only by the stability of the acetal protection in the reactive conditions. The downstream reactions are applied to both aromatic systems and the substituents of this system. Portions of the immobilized aldehyde library are directed to one or many reaction routes without limiting, producing practically unrestricted variety of products or modifications of a selected prototype. Specifically, the portions can be directed to several reactors or to multi-well plates with different reactions. One restriction that does exist is the lability of the obtained products under the conditions of deprotection. These conditions may involve incubation with concentrated HCl at the pH<1.0 (a less preferred embodiment). The reactions of elimination, hydrolysis, condensation, disproportionation reactivity between the newly formed aldehydes take place at varied yields at this stage. A strongly preferred embodiment is the use of an established gentle de-protection protocol specifically intended to minimize side-product formation. In a non-limiting example, deprotection is performed by acid-catalyzed transacetalization in acetone (in excess or as solvent), or hydrolysis in wet solvents or in aqueous acid. The reactive Schemes XII-XVIII illustrate the conditions:

Scheme XII

R'': Me, Et, CH$_2$CH$_2$

Acetals and ketals are readily deprotected under neutral conditions in the presence of acetone and indium(III) trifluoromethanesulfonate as catalyst at room temperature or mild microwave heating conditions to give the corresponding aldehydes and ketones in good to excellent yields (See B. T. Gregg, K. C. Golden, J. F. Quinn, *J. Org. Chem.*, 2007, v. 72, 5890-5893, incorporated herein by reference in entirety).

Scheme XIII

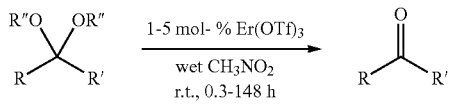

Deprotection of acetals and ketals can be achieved by using a catalytic amount of sodium tetrakis(3,5-trifluoromethylphenyl)borate (NaBArF$_4$) in water at 30° C. For example, a quantitative conversion of 2-phenyl-1,3-dioxolane into benzaldehyde was accomplished within five minutes (See C.-C. Chang, B.-S. Liao, S.-T. Liu, Synlett, 2007, 283-287, incorporated herein by reference in entirety).

Scheme XIV

Er (OTf)$_3$ is a very gentle Lewis acid catalyst in the chemoselective cleavage of alkyl and cyclic acetals and ketals at room temperature in wet nitromethane (See R. Dalpozzo, A. De Nino, L. Maiuolo, M. Nardi, A. Procopio, A. Tagarelli, *Synthesis*, 2004, 496-498, incorporated herein by reference in entirety).

Scheme XV

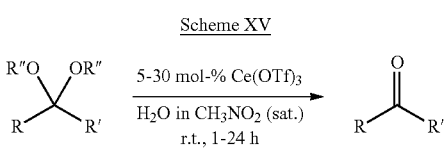

A chemoselective method for the cleavage of acetals and ketals at room temperature in wet nitromethane by using catalytic cerium(III) triflate at almost neutral pH is presented. High yields and selectivity make this procedure particularly attractive for multistep synthesis. (See: R. Dalpozzo, A. De Nino, L. Maiuolo, A. Procopio, A. Tagarelli, G. Sindona, G. Bartoli, *J. Org. Chem.*, 2002, v. 67, 9093-9095, incorporated herein by reference in entirety).

Scheme XVI

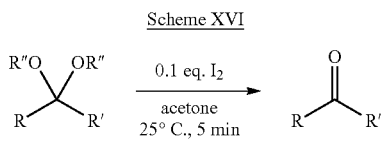

A convenient deprotection of acyclic and cyclic O,O-acetals and O,O-ketals is achieved in excellent yields within minutes under neutral conditions in the presence of a catalytic amount of iodine. Double bonds, hydroxyl groups, acetate groups, and highly acid-sensitive groups such as furyl, tert-butyl ethers, and ketoximes are tolerated. (See: J. Sun, Y. Dong, L. Cao, X. Wang, S. Wang, Y. Hu, *J. Org. Chem.*, 2004, v. 69, 8932-8934, incorporated herein by reference in entirety).

Scheme XVII

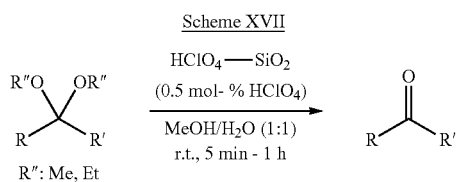

Perchloric acid adsorbed on silica gel is an extremely efficient, inexpensive, and reusable catalyst for the protection of aldehydes and ketones and the subsequent deprotection. Acetalization was mostly carried out under solvent-free conditions with trialkyl orthoformates, but weakly electrophilic carbonyl compounds and substrates that can coordinate with the catalyst, required the corresponding alcohol as solvent (See: R. Kumar, D. Kumar, A. K. Chakraborti, *Synthesis*, 2007, 299-303, incorporated herein by reference in entirety);

Scheme XVIII

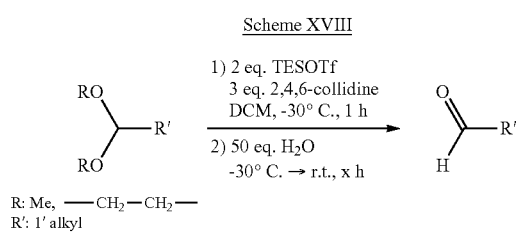

The combination of $R_3SiOTf/2,4,6$-collidine promotes a highly discriminative and chemoselective transformation of acetals bearing different substitution patterns, different types of acetals, as well as mixed acetals (See: R. Ohta, N. Matsumoto, Y. Ueyama, Y. Kuboki, H. Aoyama, K. Murai, M. Arisawa, T. Maegawa, H. Fujioka, *J. Org. Chem.*, 2018, v. 83, 6432-6443, incorporated herein by reference in entirety).

Among the Schemes XII-XVIII, the deprotection schemes XII and XVI are the most suitable, especially XVI proceeding at room temperature for 5 min. In the absence of protonation and in mild conditions, the dismutation, condensation, and elimination reactions (expected at a higher temperature and acidic conditions) are ruled out, and all solvent components are volatile. The volatiles are removed by freeze-drying the reactor under vacuum. The losses of the main products are limited by the preferred evaporation of acetone in comparison with the free modified aromatic aldehydes (acetone boiling temperature is 56° C., benzaldehyde boiling temperature is 178.1° C., benzaldehyde has the lowest molecular mass among the inventive aldehyde library). The residue in the reactor comprises the stripped solid phase and the detached aldehyde pool. After evaporating the deprotection reaction solvent, the content of the reactor thaws and the resin particles are washed with the solvent of the next reaction between the Meldrum's ketone library products and the aldehyde library.

In yet another preferred embodiment, the ketone library of Meldrum's products is combination-expanded. Such expansion takes place by protecting and immobilizing substituted ketones on the Merryfield resin support, modifying the secondary substituents of the groups R1 and R2 of the compound of formula (I), deprotecting the modified ketones and reacting them with malonate by the Meldrum's method. The combination-expanded ketone library of Meldrum's products is reacted with the combination-expanded aldehyde library to produce the final library complexity as the product of the component complexities.

In a preferred embodiment, the total diversity of ligands generated in the inventive process is partitioned into sub-libraries of manageable size, from the screening, separation, analyzing, and flexibility perspectives. The number of clearly separable peaks in HPLC is not infinite and is lower for the preparative version of HPLC vs. the analytical counterpart. Multi-step synthetic processes generate minor products that can partake in the combinatorial complexity, while being pharmacologically inactive. The advantageous number of compounds is in the range from about 100 to about 500 per single batch for the feedback-guided process of this invention (see below). Such combinatorial diversity can be synthesized and characterized by the above-described two-step protocol, producing a pool of 5000-25000 assay data points per year by a team of 10-15 drug development professionals. Considering side-products, the pool of useful ligands per laboratory is estimated to be about 1000-5000 per year. This number constitutes a substantial contribution to the overall pre-clinical drug development effort. Candidates for a new drug to treat a disease might include from 5,000 to 10,000 chemical compounds. On average, about 250 of these initial leads demonstrate sufficient promise for further evaluation using laboratory tests, mice, and other test animals (below). Typically, about ten of these qualify for tests on humans (see H. G. Stratmann, "Bad Medicine: When Medical Research Goes Wrong". Analog Science Fiction and Fact" CXXX, 2010, v. 9: 20, incorporated herein by reference in entirety). Thus, the complexity expansion is applied judiciously not to overwhelm the isolation, testing, and analysis components of the overall process by starting with a single promising lead and introducing <100 incremental modifications at a time by the methods described above.

In preferred embodiments, Quinoline and Isoquinoline positions in the aromatic domain are synthesized by the scheme XIX:

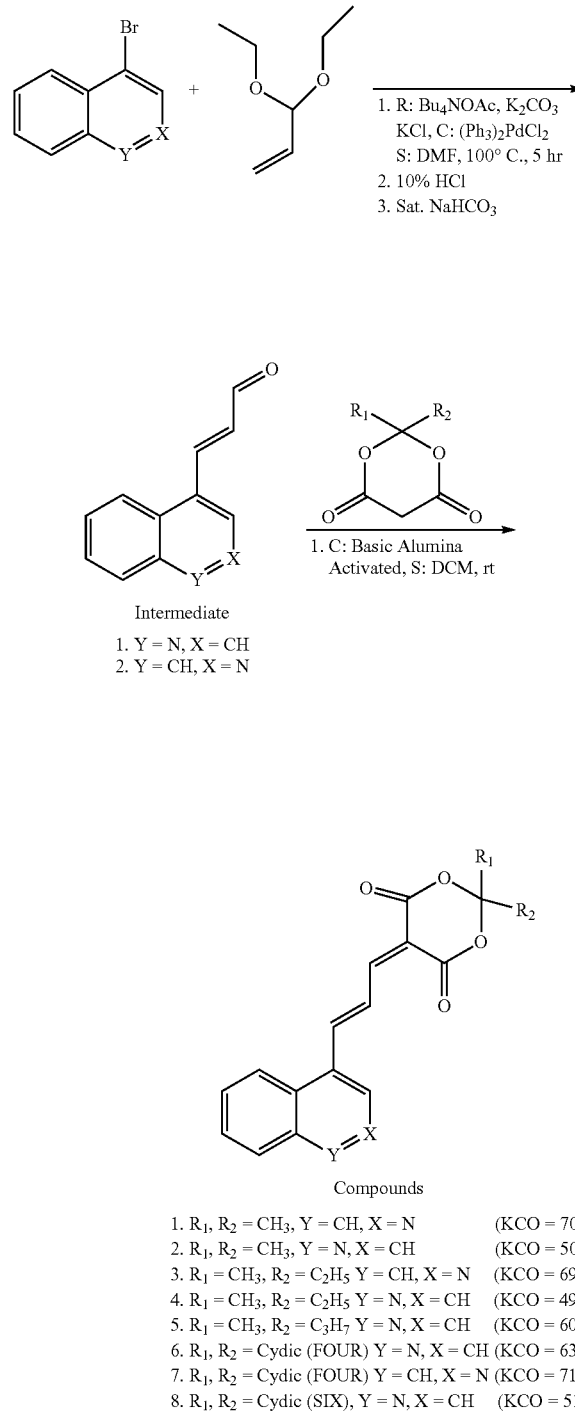

See Wittig reaction ref Zhang, Xiaojie et. al., Bioorganic & Medicinal Chemistry, 2016, 24, 4692, see Heck reaction ref Noel, Sebastien et. al. 2007, 349, 1128, incorporated herein by reference in entirety.

In an alternative embodiment, the extension of C1 side chain in aromatic aldehydes is performed by Wittig reaction (Scheme XX):

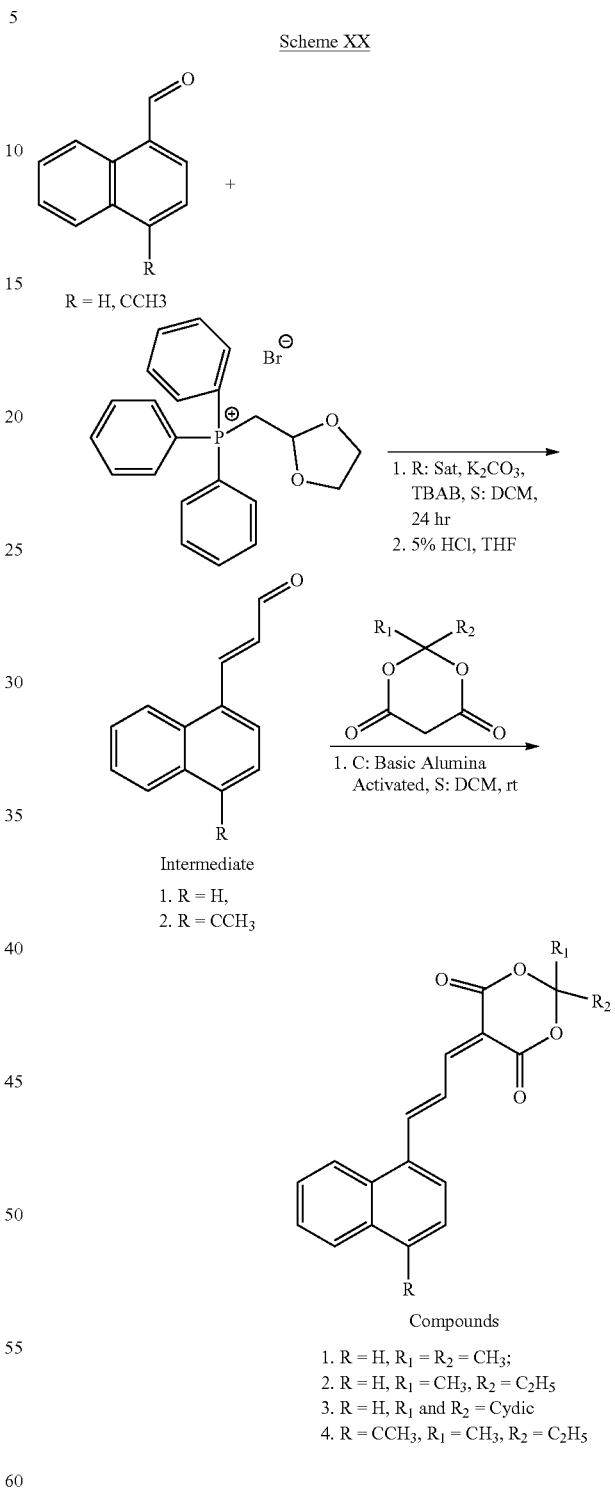

Preparation of Intermediate 3-Naphthalen-1-yl-propenal, with slight modification of the procedure in WO2016179597 incorporated herein by reference. A mixture of Naphthalene-1-carbaldehyde (511 mg, 3.5 mmol), (1,2-dioxalan-2-ylm-ethyl)triphenylphosphonium bromide (1.8 g, 4.2 mmol), tetrabytyl ammonium bromide (100 mg), in dichloromethane and saturated aqueous $K_2CO_3$ (15 ml) in DCM (30 mL) was heated to refluxed for 15 h. The layers were separated, and aqueous layer was extracted DCM (2×15 mL). The combined organic layer was washed with water (30 mL), and brine (50 mL), dried (NaSO4) and concentrated. THF (10 ml), 10% HCl (5 mL) were added and mixture was stirred for 1 h at rt. The mixture was extracted with ethyl acetate (3×20 mL). The combined organic layers were washed with water (50 mL), and brine (30 mL) and dried over sodium sulfate and concentrated. The residue was purified by flash chromatography using ISCO Teledyne and 24 g pre packed silica column and ethyl acetate/hexane solvent gradient to afford yellow solid (350 mg, 55%).

For the activity screening assays, one embodiment is the MTT colorimetric assay for assessing cell metabolic activity. NAD(P)H-dependent cellular oxidoreductase enzyme activity is proportional to the number of viable cells present. These enzymes reduce 3-(4,5-dimethylthiazol-2-yl)-2,5-diphenyltetrazolium bromide to its insoluble reduced form, which has a purple color. The assay requires limited exposure to light at the detection stage since the dye is sensitive to photobleaching. Conducting the MTT assay of the reactions of interest, the aliquots of the reactions are micropipetted into the wells of MTT assay, filled with fresh and buffered media also comprising the MTT dye. In a preferred embodiment, the MTT assay is conducted in 96-well plates holding 100 µl of a buffered serum-free media in each well, the cells are grown to 90% of confluence, and 2-5 µl of the reactions are directly added to the wells with the solvent controls. The serum-free content of the medium is required to avoid the distortions associated with the presence of serum albumin protein, differentially binding the synthesized molecules based on hydrophobicity. The incubation with MTT in the presence of the potential active leads continues for 6-12 hours and can be optionally overnight. The cell culture is maintained in the incubators at 37° C. and 5% $CO_2$ when the actual measurements are not conducted. The presence of antibiotics and antimycotics in the media is necessary, considering the intensity of the described screening. After measuring the MTT signals, the media is changed, and the cells are inspected microscopically for the morphological changes or for the presence of the mycoplasma, bacterial, or fungal colonies that escaped the turbidity measurement. Visible loss of the ameboid shape inherent to the healthy immortalized cell lines typically used in MTT assays confirms the efficiency of the treatment if in the solvent control, the viable native morphology is retained. The assay is repeated then to ensure that the effect is not an artifact but is causatively traced to the drug lead (dose dependence).

In a preferred embodiment, the MTT assay is conducted in multiple cell lines. The standard cell lines are derived from tumors and are immortalized, meaning that the Hayflick limit for the maximal number of cell divisions (inherent to the physiologically normal cells) is absent in the immortalized transformants. The process of immortalization is caused by the expression of oncogenes, altering the epigenetic state, and allowing the expression of at least telomerase pathway components. The latter restore the integrity of chromosomal telomeres, preventing the critical extent of telomere shortening, triggering the cellular senescence pathway (the Hayflick limit). The cell cultures are certified morphologically and by the presence of the line-specific surface markers at the ATCC (American Type Culture Collection).

A potential lead is more potent when it inhibits multiple cell lines. While the immortalized lines are very different physiologically from the primary tumor cells and each other, the signature of inhibition across multiple cell lines correlates with the signature for the primary tumor cells. Furthermore, the disproportional inhibition in some cell lines while relative inactivity in the remaining profile indicates a tissue-specific lead, most promising for the treatment of cancers of a certain tissue origin.

Another preferred embodiment includes the primary cells adapted to growth in serum-free media. Such primary (non-transformed) lines include endothelial (HUVEC), hepatocyte, cardiomyocyte, neuroblast, and stem cells. The incorporation of the primary cells in the testing panel allows empirically estimating the therapeutic window. The leads not inhibiting a single primary cell type in the panel, but deeply inhibiting at least one transformed cell line are more promising than those that impact the primary cell types (at least one), even if they also impact the transformed lines. Non-interaction with the primary normal cells raises the probability of advancement of the ligand in the overall drug-development process. A more preferred embodiment is when the equivalents of the primary cells are produced by trans-differentiation of the pluripotent cells, allowing the production of different primary tissue lineages in-house from the immortalized but non-cancerous source (stem cells).

The immortalized cell lines included in the testing panel of this disclosure are MCF7 (a breast cancer cell line), MCF10 (immortalized human breast epithelial cells), MDA-MB231 (an epithelial, human breast cancer cell line that was established from a pleural effusion of a patient with a metastatic mammary adenocarcinoma), KAIMRC1 (a naturally immortalized human breast carcinoma cell line), KAIMRC2 (a naturally immortalized breast cancer cell line). The primary cells available for lead toxicity assays are, without limitation: hepatocytes (supplied by Xenotech, Bioscience Lonza, Accegen, Biocompare, Gibco, Zen-Bio, Takarabio, AxolBio, Creative Bioarray), cardiomyocytes (supplied by Cellartis, Axolbio, Cedarlanelabs, EMD Millipore, Takara Bio, Neuromics, AcceGene), primary neurons (AcceGen, Cellapplications, Neuromics, Biocompare, AxolBio, BrainXcell), endothelial lining (Thermofisher, Accegen, Biocompare, Promocell, ATCC). Multicellular 3D organoids raised by differentiating iPSC (induced pluripotent stem cells) are provided by Sigma Aldrich (the iPSC cell lines, organoids), Tocris Bioscience, Thermofisher, Stemcell Technologies, Takara Bio, Emulatebio (Human organ chips), Prodolabs.

The use of organoid-on-chip technology is especially advantageous since these models emulate the natural connectivity and signaling between the normal cells and provide a more precise assessment of toxicity. Inclusion of the primary cell panels in the combinatorial lead improvement is advantageous, allowing to exclude toxic leads from further modification and concentrate the financial and time resources on the leads with a wide therapeutic window.

Another embodiment discloses Titer Glo Assay for the characterization of the synthesized compounds. The CellTiter-Glo® Luminescent Cell Viability Assay is a homogeneous method of determining the number of viable cells in culture based on quantitation of the ATP present, an indicator of metabolically active cells. The CellTiter-Glo® Assay is designed for use with multiwell formats, making it ideal for automated high-throughput screening (HTS), cell proliferation, and cytotoxicity assays. The homogeneous assay procedure involves adding the single reagent (CellTiter-Glo® Reagent) directly to cells cultured in serum-supplemented medium. Cell washing, removal of medium, and multiple pipetting steps are not required. The system detects as few as 15 cells/well in a 384-well format in 10 minutes after adding reagent and mixing.

In still another embodiment, the cell viability assay measures the rate of apoptosis (programmed cell death) induced by the lead of interest. The vendors of the assays selectively detecting drug-induced apoptosis without limitation are Promega, Miltenyibiotec, Biovision, Biotium, Abcam, Sigma-Aldrich. Apoptosis includes Early-Stage Events: Translocation of phosphatidylserine to the outer leaf of the plasma membrane, loss of mitochondrial membrane potential, cytochrome C & ATP release, and activation of caspase-8 and 9. Mid-Stage Events: Activation of caspase-3, 6 and 7, Poly-ADP-Ribose polymerase (PARP) cleavage, cell shrinkage, and activation of nucleases. Late-Stage Events: DNA fragmentation, nuclear collapse, formation of apoptotic bodies, and phagocytosis by macrophages. Annexin V Assays (for early apoptosis stage): Phosphatidylserine is normally confined in the inner membrane leaflet of viable cells. The translocation of phosphatidylserine to the exposed membrane surface is an early event in apoptosis, where it serves as a signal for the attack of phagocytic cells. Annexins are a family of structurally related proteins that can bind specifically to cellular membranes. Annexin V has a very high affinity for membranes containing the negatively charged phospholipid phosphatidylserine and can be used as a marker of early apoptosis events.

Caspase Detection Assays (for mid-stage of apoptosis): A central component of the apoptotic process is a cascade of proteolytic enzymes called caspases. Caspases participate in a series of reactions that are triggered in response to pro-apoptotic signals and result in the cleavage of protein substrates, causing the disassembly of the cell. Caspase enzymes specifically recognize a 4 or 5 amino acid sequence on the target substrate, which necessarily includes an aspartic acid residue. This residue is the target for cleavage, which occurs at the carbonyl end of the aspartic acid residue.

TUNEL Assays (for late-stage apoptosis): DNA fragmentation in apoptosis is usually associated with structural changes in cellular morphology and is a hallmark of late-stage apoptosis. DNA fragmentation in apoptosis can be examined using the TUNEL assay. The in situ staining of DNA strand breaks detected by the TUNEL assay, and subsequent visualization by light microscopy gives biologically significant data about DNA damage and late-stage apoptosis.

In yet another embodiment, assays are conducted in the presence of serum to ensure that after binding to serum albumin, the lead is still active and is capable of inhibition. Additionally, in the presence of growth factors in the serum component of the assay media, the tested cell lines may be rescued from the drug-induced apoptosis, while the serum-free environment often produces irrelevant results since in a living organism the same set of rescue factors is available. Consistency between serum-free and in-serum data is an important component of ligand evaluation.

In yet another preferred embodiment, the synthesis of the library and the testing proceed synchronously, the synthesized diversities are low (<100 molecular species per batch), the assay includes both the immortalized and primary normal cell components and is conducted in the serum-supplemented media. In this scheme, the results of a sophisticated assay provide the empirical feedback to the synthetic component of lead development and allow focusing of the effort on the most promising ligands, showing wide therapeutic window estimates. The feedback-directed synthetic effort produces a much faster improvement in the lead pool average quality than mere scanning of all possibilities.

The ligands showing the wide therapeutic window estimates are then tested in the organoid-on-the-chip assays, which are more expensive but also more proximal to the response of real biological tissue where the individual cells are interconnected producing a pro-survival environment. This pro-survival environment fosters the resilience of both normal tissues to the toxic effects of the drug candidates and of the malignant foci to the intended therapeutic effects. The net result of the cell connectivity effect is a shift in the required doses and a change in the width of the therapeutic window.

In the more preferred embodiment, the ligands that passed with high scores the combined cell assay stage (including the primary cell lines, serum presence, and the organoid level cell connectivity) are upgraded for xenograft testing. Xenograft testing involves the production of immunocompromised murine hosts not capable of rejecting the implanted immortalized or patient-derived cell lines simulating cancer development. The patient-derived xenograft version (PDX) is more preferred since the implanted cells use the mouse host stimuli to develop the connectivity and histology resembling that in human metastasis. The first generation of mice receiving the patient's tumor fragments are commonly denoted F0. When the tumor-burden becomes too large for the F0 mouse, the tumor is passed to the next generation of mice. Each generation thereafter is denoted F1, F2, F3 . . . Fn. For drug development studies, the expansion of mice after the F3 generation is often utilized after ensuring that the PDX has not genetically or histologically diverged from the patient's tumor in the transition to the rodent environment. The PDX allows testing of the known and investigational drugs in a personalized manner and would allow use of investigational drugs for treatment of late-stage cancers by the ligands that demonstrated clinical trial efficiency but are not yet approved by the government regulators.

In one preferred embodiment, the PDX model is humanized. The immunodeficient mice must be used to prevent immune attacks against the xenotransplanted tumor. With the immune system incapacitated, a critical component of the known tumor microenvironment interaction is lost, preventing immunotherapies, anti-cancer agents that target the immune system components, and the inventive ligands from being studied in PDX models as interactors and synergists. To bypass these possibilities, the humanized-xenograft models are created by co-engrafting the patient tumor fragment and peripheral blood or bone marrow cells into a NOD/SCID (Non-obese diabetic/severe combined immunodeficiency) mouse. The co-engraftment allows for reconstitution of the murine immune system, giving insight into the interactions between xenogenic human stroma and tumor environments in cancer progression and metastasis.

The non-limiting list of xenograft mouse providers includes Rincon Bio (outsourced cancer model testing), The Jackson Laboratory, Noble Life Sciences, IITRI. The murine strains suitable for xenograft testing are of BALB/c or B6 background, being severe combined immunodeficiency (SCID), athymic, or other immune compromised mutants used for cancer biology at this level, due to the depth of immunosuppression. Table 2 presents the non-limiting list of typical immunocompromised mouse strains with further clarification available at the level of the providers (specialized biotechnology firms).

TABLE 4

List and properties of the immunocompromised mouse strains, suitable for xenografting.

| Strain | Hair Coat | Mature T Cells | Mature B Cells | NK Cells | Genetics |
|---|---|---|---|---|---|
| Athymic Nude Mouse | No | Absent | Present | Present | Outbred |
| BALB/c Nude Mouse | No | Absent | Present | Present | Inbred |
| CD-1 Nude Mouse | No | Absent | Present | Present | Outbred |
| Fox Chase SCID ® Mouse | Yes | Absent | Absent | Present | Congenic |
| Fox Chase SCID ® Beige Mouse | Yes | Absent | Absent | Defective | Congenic |
| NCG Mouse | Yes | Absent | Absent | Absent | Coisogenic |
| NOD SCID Mouse | Yes | Absent | Absent | Defective | Congenic |
| NIH-III Nude Mouse | No | Absent | Absent | Defective | Outbred |
| NU/NU Nude Mouse | No | Absent | Present | Present | Outbred |
| SCID Hairless Congenic (SHC ™) Mouse | No | Absent | Absent | Present | Congenic |
| SCID Hairless Outbred (SHO ®) Mouse | No | Absent | Absent | Present | Outbred |
| NCI SCID/NCr Mouse | Yes | Absent | Absent | Present | Congenic |

In another preferred embodiment, the ligands that are not selected in the next tier based on the individual performance, but performing in the percentile >95% are re-tested as synergists and potentiators with the panel of known anti-cancer therapeutics such as taxols, taxanes, etoposides, platinum compounds, anti-cancer antibiotics, antimetabolites, targeted therapeutics, radiation, retinoids, immunotherapies without limitation. Preferably, such interactions are measured on cheap cell assays, allowing rapid testing of multiple combinations of the known agents with the best investigational agents. The embodiment is advantageous since it allows to develop not only the individual therapeutics but also combinational therapies and provides a more economical scheme of ligand screening utilizing more leads and producing lower attrition. The ligands that may be less effective individually, but potentiating the pool of known treatments have a niche and can be continued in development process as combinations.

The prediction rules differentiating the passing and failing ligands are applied to the current population of best leads, isolating the top 10% (5 out of the top 50), which are likely to be tested in Phase I Clinical trial in healthy volunteers.

In a more preferred embodiment, the distance between the positive, negative and developing ligands is measured quantitatively. Such a metric of a distance can be the width of the therapeutic window in the positive, and negative classes. The width of the therapeutic window is defined by the ratio of IC50 measured in the primary human cell culture and organoids (geometric mean between the two) and IC50 for the most vulnerable cancer cell line of the testing panel. High ratio means that the primary human cells are not sensitive to the levels of the agent that inhibit cancer cells. Another IC50 ratio is measured between the level of the drug that inhibits or kills the mouse xenograft host and the level that inhibits the grafted cancer development in the said host. The first ratio and the second ratio are combined with the weights that correspond to the best separation between the positive and negative controls. The distribution of the weighted ratios is compared for the negative, positive, and the developing ligands. The difference between the averages for the positive and negative groups is "distance", and the difference between the average for the positive and the developing ligand is termed "closeness". The developing ligands are ranked by the closeness, with the lower values producing higher ranks.

The approved compounds are applied as monotherapies, combination therapies and potentiators of radiation therapy such as those of the present disclosure. Both solid tumors and leukemias are treated by the structures of the invention. The non-limiting examples of anti-cancer treatment by newly developed pre-approved and approved ligands (of any chemistry) incorporated herein by reference in entirety and without limiting:

a) Pre-approved ligands: U.S. Pat. No. 9,757,364, US2018237451, U.S. Pat. No. 9,481,669, US2018298008, US2019350932, US2018194724, US2018194724, US2012277230, US2017253629, US2016237075, US2010331307, US2008275057, WO18195123, US2009326020, US2016022721.

b) Pre-approved ligands combined with the approved: US2010285008, US2004147541, KR102025323, US2016287539, US2011142815, US2015315131, US2006074126, U.S. Pat. No. 8,980,932, US2011172226, U.S. Pat. Nos. 7,666,897, 9,180,214, US2007071672, U.S. Pat. No. 7,427,689.

The publications above illustrate the typical applications and tests of the novel antineoplastic candidates at the pre-approval stage.

In one embodiment, the pharmaceutical composition further comprises one or more other active pharmaceutical agents. Exemplary pharmaceutical agents include, but are not limited to chemotherapeutic agents aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab and the like.

In one embodiment, the pharmaceutical composition is in solid, semi-solid or liquid dosage forms.

In one embodiment, the pharmaceutical composition is formulated for at least one mode of administration selected from the group consisting of oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration and sublingual administration.

In one embodiment, the present disclosure provides a pharmaceutical composition, comprising a pharmaceutically acceptable carrier and a therapeutically effective amount of at least one of the complexes of the present disclosure or a pharmaceutically acceptable salt, solvate, or prodrug thereof.

In one embodiment, the pharmaceutical composition comprises 1-99.9%, preferably 10-99.9%, more preferably 20-99.9%, more preferably 30-99.9%, more preferably 40-99.9%, more preferably 50-99.9%, more preferably 60-99.9%, more preferably 70-99.9%, more preferably 80-99.9%, even more preferably 90-99.9% of the compound of formula (I), and 0.1% or more of the pharmaceutically acceptable carrier or excipient, based on the total weight of the composition.

Methods of preparing these formulations or compositions include the step of bringing into association a ligand of the present disclosure with the carrier and, optionally, one or more accessory ingredients. In general, the formulations are prepared by uniformly and intimately bringing into association a ligand of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a complex of the present disclosure as an active ingredient. A ligand of the present disclosure may also be administered as a bolus, electuary or paste.

Pharmaceutical compositions of this disclosure suitable for parenteral administration comprise one or more ligands of the disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful, Suppositories for rectal administration of the compound or an analog or derivative thereof can be prepared by mixing the steroid or an analog or derivative thereof with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

If administered per os, a compound of formula (I) can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

When the compounds of the present disclosure are administered as pharmaceuticals, to humans and animals, they can be given per se or as a pharmaceutical composition containing, for example, 1-99.9%, preferably 10-99.9%, more preferably 20-99.9%, more preferably 30-99.9%, more preferably 40-99.9%, more preferably 50-99.9%, more preferably 60-99.9%, more preferably 70-99.9%, more preferably 80-99.9%, even more preferably 90-99.9% of active ingredient in combination with a pharmaceutically acceptable carrier.

Regardless of the route of administration selected, the compounds of the present disclosure, which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient. A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

The present disclosure relates to a method for the treatment of a proliferative disorder in a patient, involving administering to the patient a therapeutically effective amount of the compound of formula (I) or a pharmaceutically acceptable salt, solvate, or prodrug thereof.

In one embodiment, the proliferative disorder is cancer.

The neoplastic activity of the tumor or cancer cells may be localized or initiated in one or more of the following: blood, brain, bladder, lung, cervix, ovary, colon, rectum, pancreas, skin, prostate gland, stomach, breast, liver, spleen, kidney, head, neck, testicle, bone (including bone marrow), thyroid gland, central nervous system. The compound of formula (I) of the present disclosure or the pharmaceutical composition thereof can be applied in the treatment or prevention of breast cancer, colorectal cancer (including colon cancer, rectum cancer and bowel cancer); lung cancer (including non-small cell lung carcinoma or NSCLC and small cell lung carcinoma); cervical cancer (including the histologic subtypes of squamous cell carcinoma, adenocarcinoma, adenosquamous carcinoma, small cell carcinoma, neuroendocrine tumor, glass cell carcinoma, villoglandular adenocarcinoma, melanoma and lymphoma).

Cancers such as, but not limited to sarcomas, carcinomas, melanomas, myelomas, gliomas and lymphomas can be treated or prevented with the compound of formula (I) provided herein. In some embodiments, methods incorporating the use of at least one of the compounds of the present disclosure are effective in the treatment or prevention of cancer of the blood, brain, bladder, lung, cervix, ovary, colon, rectum, pancreas, skin, prostate gland, stomach, breast, liver, spleen, kidney, head, neck, testicle, bone (including bone marrow), thyroid gland or central nervous system. In some embodiments, these methods are especially effective in the treatment or prevention of cervical, colon and lung cancers.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, after treatment, the size of a tumor, whether by volume, weight or diameter, is reduced by at least 5%, 10%, 15%, 20%, 25%, 30%, 40%, 50%, 60%, 70%, 75%, 80%, 85%, 90%, 95%, 99% or 100%, relative to the tumor size before treatment. In other embodiments, after treatment with the one or more compounds of formula (I) of a pharmaceutical composition thereof, the size of a tumor does not reduce but is maintained the same as the tumor size before treatment. Methods of assessing tumor size include but are not limited to CT Scan, MRI, DCE-MRI and PET Scan.

In some embodiments, the method for treating cancer and other proliferative disorders involves the administration of a unit dosage or a therapeutically effective amount of one or more compounds of formula (I) derivatives or a pharmaceutical composition thereof to a mammalian subject (preferably a human subject) in need thereof. As used herein, "a subject in need thereof" refers to a mammalian subject, preferably a human subject, who has been diagnosed with, is suspected of having, is susceptible to, is genetically predisposed to or is at risk of having at least one form of cancer. Routes or modes of administration are as set forth herein. The dosage and treatment duration are dependent on factors such as bioavailability of a drug, administration mode, toxicity of a drug, gender, age, lifestyle, body weight, the use of other drugs and dietary supplements, cancer stage, tolerance and resistance of the body to the administered drug, etc., then determined and adjusted accordingly. The one or more compounds of formula (I) or pharmaceutical composition thereof may be administered in a single dose or multiple individual divided doses. In some embodiments, the interval of time between the administration of the compound of formula (I) or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, the compound of formula (I) compounds provided herein and one or more additional therapies are administered less than 1 day, 1 week, 2 weeks, 3 weeks, 4 weeks, one month, 2 months, 3 months, 6 months, 1 year, 2 years, or 5 years apart.

Having generally described this disclosure, a further understanding can be obtained by reference to certain specific examples which are provided herein for purposes of illustration only and are not intended to be limiting unless otherwise specified.

EXAMPLE 1: 5-(3-ANTHRACEN-9-YL-ALLYLIDENE)-PYRIMIDINE-2,4,6-TRIONE

Synthesis of Compound 1

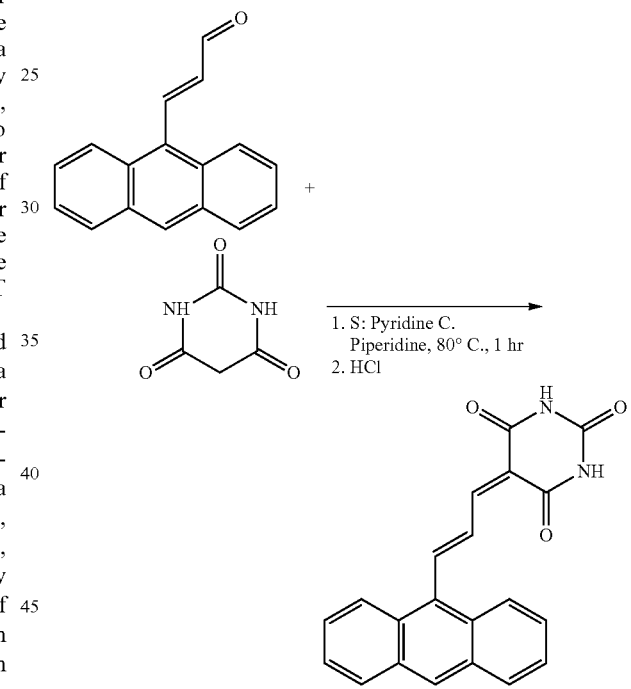

The compound 1 was synthesized by the reaction of (E)-3-(anthracen-9-yl)acrylaldehyde (0.4 g, 1.7 mmoles) with barbituric acid (0.44 g, 3.4 mmoles,) in pyridine (7 mL) and catalytic amounts of piperidine (0.05 mL). The reaction mixture was stirred at 80° C., under Argon gas, for 10 minutes or till the aldehyde was consumed. Reaction progress was monitored using silica gel TLC and 25% Ethyl acetate in hexanes as the mobile phase. Compound 9 was crashed out of the reaction mixture by adding enough aqueous HCl (10%) to neutralize the pyridine. The crude product was suction filtered through a glass frit and washed with D.I. water before recrystallizing it from THF and water. Obtained brick-red powder crystals (0.5 g, yield=80%).

1H-NMR (400 MHz, DMSO-D6) δ 11.10 (s, 1H), 11.01 (s, 1H), 8.32-8.55 (m, 6H), 7.98 (d, J=8.2 Hz, 2H), 7.48 (td, J=14.8, 6.4 Hz, 4H); MS-ESI m/z=343 (M+1)

EXAMPLE 2: 5-(3-ANTHRACEN-9-YL-ALLYLIDENE)-2-ETHYL-2-METHYL-[1,3]DIOXANE-4,6-DIONE

Synthesis of Compound 2:

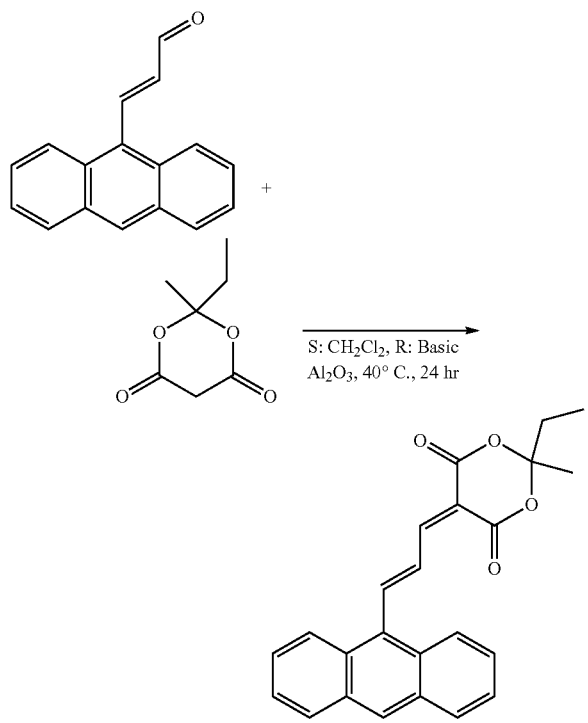

Compound 2 was synthesized by the condensation of (E)-3-(anthracen-9-yl)acrylaldehyde (0.3 g, 1.3 mmoles) with 2-ethyl-2-methyl-1,3-dioxane-4,6-dione (0.4 g, 2.6 mmoles, 2 equivalent) in dry dichloromethane (10 mL) and activated basic Alumina (1 g) as the heterogeneous catalyst. The reaction was stirred at 40° C. under Argon gas atmosphere for 24 hours or till the aldehyde was consumed. Reaction progress was monitored using silica gel TLC and 25% Ethyl acetate in hexanes as the mobile phase. The organic solvent was removed under reduced pressure and the crude product was recrystallized from boiling Ethanol/water to afford red crystals (0.3 g, yield=60%).

1H-NMR (400 MHz, DMSO-D6) δ 8.84-8.75 (1H), 8.58-8.49 (2H), 8.42-8.35 (2H), 8.26-8.15 (1H), 8.06-7.99 (2H), 7.58-7.44 (4H), 2.04-1.93 (2H), 1.76-1.67 (3H), 1.12-1.01 (3H).

EXAMPLE 3: 5-ANTHRACEN-9-YLMETHYLENE-PYRIMIDINE-2,4,6-TRIONE

Synthesis of Compound 3:

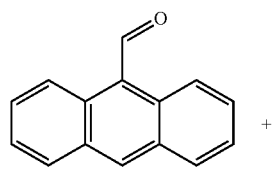

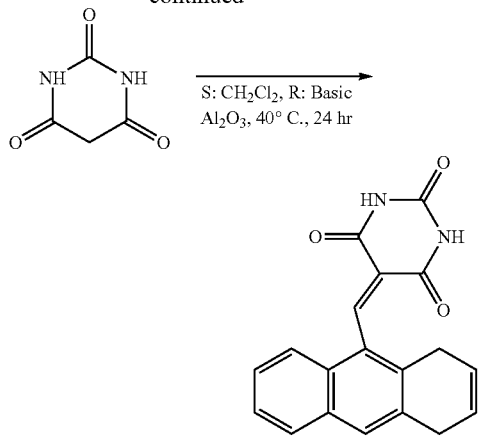

Compound 3 was synthesized by condensing 9-anthraldehyde with barbituric acid following a procedure similar to that used to synthesize example 2. The product was purified by recrystallization from boiling ethanol/water to furnish orange crystals with 70% yield.

1H-NMR (400 MHz, DMSO-D6) δ 10.97 (s, 1H), 9.04 (t, J=15.2 Hz, 1H), 8.47 (s, 1H), 7.82-8.01 (m, 4H), 7.38-7.48 (m, 4H)

MS-ESI m/z=373 (M+1)

EXAMPLE 4: 5-(3-ANTHRACEN-9-YL-ALLYLIDENE)-THIAZOLIDINE-2,4-DIONE

Synthesis of Compound 4:

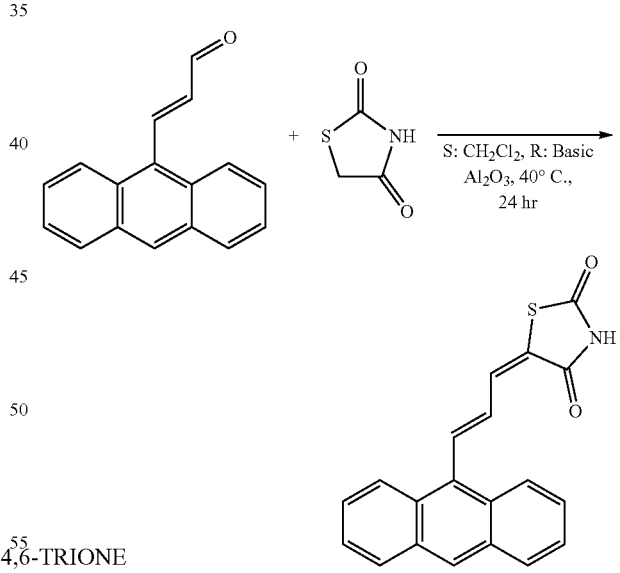

Compound 4 was synthesized by condensing (E)-3-(anthracen-9-yl)acrylaldehyde with thiazolidine-2, 4-dione following a procedure similar to that used to synthesize compound 2. The product was purified by recrystallization from acetonitrile to obtain red crystals (Yield=45%)

1H-NMR (400 MHz, ACETONE-D6) δ 8.58 (s, 1H), 8.33-8.37 (m, 2H), 8.26 (d, J=15.6 Hz, 1H), 8.04-8.13 (m, 2H), 7.81-7.87 (m, 1H), 7.51-7.58 (m, 4H), 6.77 (dd, J=15.5, 11.3 Hz, 1H)

MS-ESI m/z=332 (M+1)

EXAMPLE 5: 5-(3-PHENYL-ALLYLIDENE)-THIAZOLIDINE-2,4-DIONE

Synthesis of Compound 5:

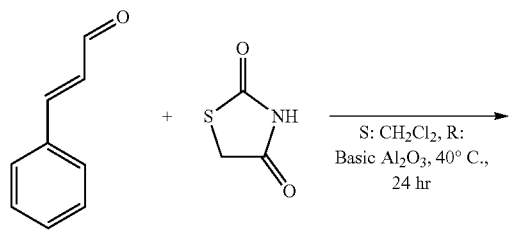

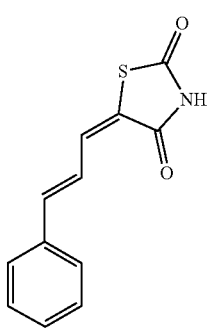

Compound 5 was synthesized by condensing cinnamaldehyde with thiazolidine-2,4-dione following a procedure similar to that used to synthesize compound 2. The product was purified by recrystallization from boiling ethanol/water to furnish light orange crystals (Yield=54%)

1H-NMR (400 MHz, DMSO-D6) δ 7.47-7.49 (m, 2H), 7.38 (dd, J=11.4, 0.7 Hz, 1H), 7.24-7.33 (m, 3H), 7.05 (d, J=15.3 Hz, 1H), 6.68 (dd, J=15.3, 11.4 Hz, 1H)

MS-ESI m/z=232 (M+1)

EXAMPLE 6: 5-(3-QUINOLIN-4-YL-ALLYLIDENE)-PYRIMIDINE-2,4,6-TRIONE

Synthesis of Compound 6:

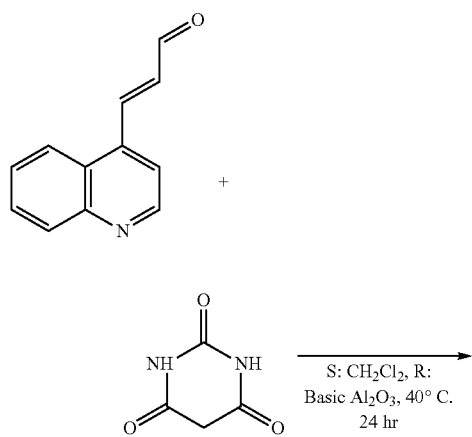

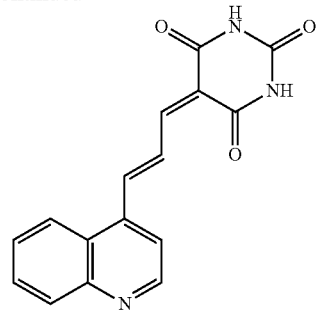

Compound 6 was synthesized by condensing (E)-3-(quinolin-4-yl)acrylaldehyde with barbituric acid following a procedure similar to that used to synthesize compound 2. The product was purified by recrystalization from boiling ethanol and triturated with hot water. Obtained orange crystals (Yield=83%)

1H-NMR (400 MHz, DMSO-D6) δ 11.32 (dd, J=31.1, 13.7 Hz, 2H), 8.94-8.99 (m, 1H), 8.58-8.68 (m, 2H), 8.42-8.46 (m, 1H), 8.17-8.27 (m, 1H), 8.02-8.10 (m, 1H), 7.67-7.84 (m, 3H)

MS-ESI m/z=294 (M+1)

EXAMPLE 7: 5-(3-QUINOLIN-4-YL-ALLYLIDENE)-THIAZOLIDINE-2,4-DIONE

Synthesis of Compound 7:

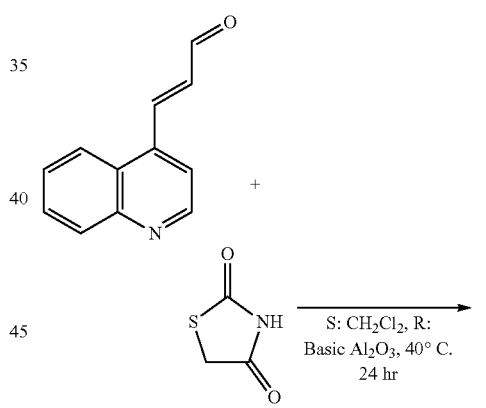

Compound 7 was synthesized by condensing (E)-3-(quinolin-4-yl)acrylaldehyde with thiazolidine-2,4-dione following a procedure similar to that used to synthesize compound 2. The product was purified by recrystallization from boiling ethanol/water to furnish light orange crystals (Yield=59%)

1H-NMR (400 MHz, DMSO-D6) δ 9.86 (d, J=7.3 Hz, 1H), 9.70 (s, OH), 8.88 (d, J=4.6 Hz, 1H), 8.81 (t, J=4.8 Hz, 1H), 8.44 (d, J=15.8 Hz, 1H), 8.15-8.28 (m, 2H), 8.04-8.07 (m, 1H), 6.89-7.03 (m, 2H)

MS-ESI m/z=283 (M+1)

EXAMPLE 8: 5-QUINOLIN-4-YLMETHYLENE-PYRIMIDINE-2,4,6-TRIONE

Synthesis of Compound 8:

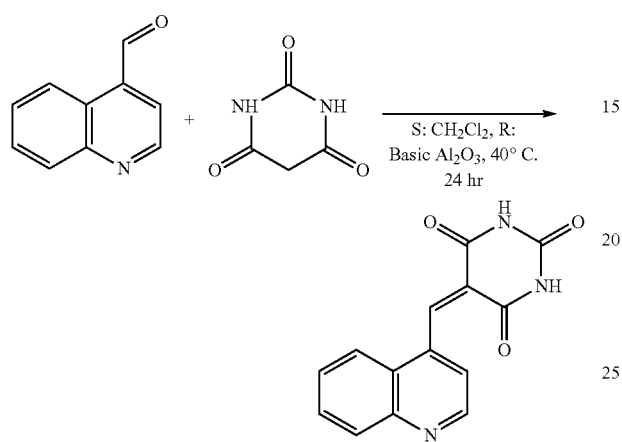

Compound 8 was synthesized by condensing quinoline-4-carbaldehyde with barbituric acid following a procedure similar to that used to synthesize compound 2. Yield=88%

1H-NMR (400 MHz, DMSO-D6) δ 10.15 (t, J=14.8 Hz, 3H), 8.82 (d, J=5.3 Hz, 1H), 8.27 (d, J=8.5 Hz, 1H), 7.98-8.03 (m, 1H), 7.75-7.81 (m, 1H), 7.58 (t, J=7.4 Hz, 1H), 7.46 (dd, J=15.1, 4.8 Hz, 1H)

MS-ESI m/z=268 (M+1)

EXAMPLE 9: 2-ETHYL-2-METHYL-5-(3-PYRIDIN-4-YL-ALLYLIDENE)-[1,3]DIOXANE-4,6-DIONE

Synthesis of Compound 9:

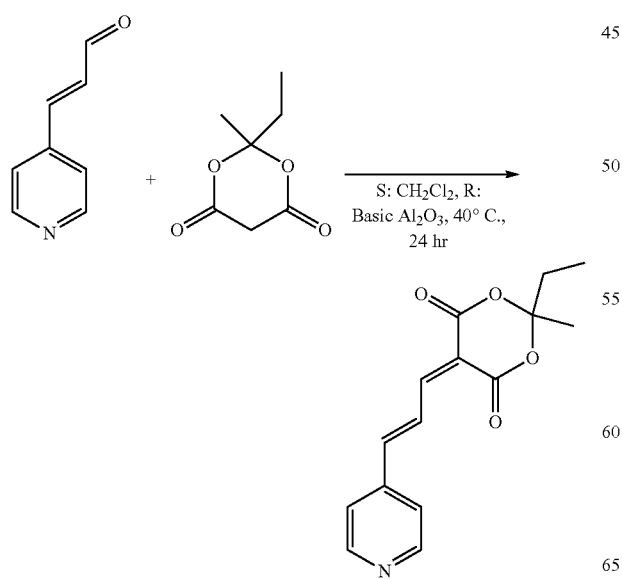

Compound 9 was synthesized by condensing (E)-3-(pyridin-4-yl) acrylaldehyde with 2-ethyl-2-methyl-1,3-dioxane-4,6-dione following a procedure similar to that used to synthesize compound 2. The product was purified by recrystallization from boiling ethanol/water to furnish light orange crystals (Yield=60%)

1H-NMR (400 MHz, CHLOROFORM-D) δ 8.79-8.61 (2H), 8.55-8.33 (1H), 8.22-8.01 (1H), 7.55-7.39 (2H), 7.36-7.16 (1H), 2.09-1.89 (2H), 1.82-1.64 (3H), 1.17-0.97 (3H)

MS-ESI m/z=274 (M+1)

EXAMPLE 10: 5-(3-ISOQUINOLIN-4-YL-ALLYLIDENE)-2,2-DIMETHYL-[1,3]DIOXANE-4,6-DIONE

Quinoline and Isoquinoline Analogs:

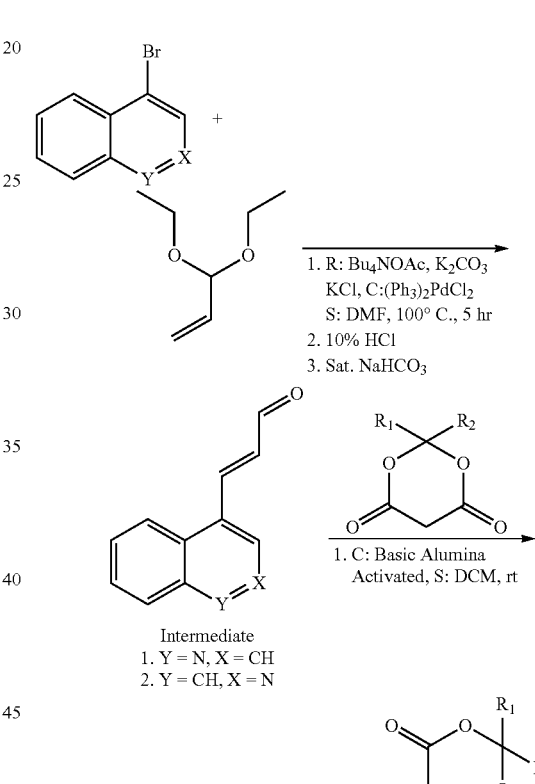

Compounds
1. $R_1, R_2$ = $CH_3$, Y = CH, X = N (KCO = 70)
2. $R_1, R_2$ = $CH_3$, Y = N, X = CH (KCO = 50)
3. $R_1$ = $CH_3$, $R_2$ = $C_2H_5$ Y = CH, X = N (KCO = 69)
4. $R_1$ = $CH_3$, $R_2$ = $C_2H_5$ Y = N, X = CH (KCO = 49)
5. $R_1$ = $CH_3$, $R_2$ = $C_3H_7$ Y = N, X = CH (KCO = 60)
6. $R_1, R_2$ = Cyclic (FOUR) Y = N, X = CH (KCO = 63)
7. $R_1, R_2$ = Cyclic (FOUR), Y = CH, X = N (KCO = 71)
8. $R_1, R_2$ = Cyclic (SIX), Y = N, X = CH (KCO = 51)

Intermediate 1 3-Quinolin-4-yl-propenal was synthesized as known in art by Wittig reaction ref Zhang, Xiaojie et. al., Bioorganic & Medicinal Chemistry, 2016, 24, 4692.

Intermediate 2 3-Isoquinolin-4-yl-propenal was synthesized as known in art by Heck reaction ref Noel, Sebastien et. al. 2007, 349, 1128.

The compound 10 was synthesized from intermediate 2 3-Isoquinolin-4-yl-propenal, and 2,2-dimethyl-[1,3]dioxane-4,6-dione following the experimental procedure of compound 2. It was purified by flash column on $SiO_2$ (10%) EtOAc/Hexane to furnish orange solid (Yield 65%); 1H-NMR (400 MHz, DMSO-D6) δ 9.20 (s, 1H), 8.92 (s, 1H), 8.48-8.54 (m, 1H), 8.35-8.40 (m, 3H), 8.04 (d, J=8.0 Hz, 1H), 7.79-7.83 (m, 1H), 7.64-7.68 (m, 1H), 1.75 (s, 6H); MS-ESI m/z=310 (M+1)

EXAMPLE 11: 2,2-DIMETHYL-5-(3-QUINOLIN-4-YL-ALLYLIDENE)-[1,3]DIOXANE-4,6-DIONE

The compound 11 was synthesized from intermediate 1 3-quinolin-4-yl-propenal, and 2,2-dimethyl-[1,3]dioxane-4,6-dione following the experimental procedure of compound 2. It was purified by flash column on $SiO_2$ (10%) EtOAc/Hexane to furnish orange solid (Yield 55%); 1H-NMR (400 MHz, DMSO-D6) δ 8.87-8.92 (m, 1H), 8.59 (td, J=11.7, 8.8 Hz, 1H), 8.32-8.45 (m, 3H), 8.01-8.05 (m, 1H), 7.58-7.77 (m, 3H), 1.72-1.83 (m, 6H); MS m/z=310 (M+1)

EXAMPLE 12: 2-ETHYL-5-(3-ISOQUINOLIN-4-YL-ALLYLIDENE)-2-METHYL-[1,3]DIOXANE-4,6-DIONE

The compound 12 was synthesized from intermediate 2 3-Isoquinolin-4-yl-propenal, and 2-Ethyl-2-methyl-[1,3]dioxane-4,6-dione following the experimental procedure of compound 2. It was purified by flash column on $SiO_2$ (10%) EtOAc/Hexane to furnish orange solid (Yield 70%)

1H-NMR (400 MHz, DMSO-D6) δ 9.20 (s, 1H), 8.93 (s, 1H), 8.35-8.52 (m, 4H), 8.04 (d, J=8.0 Hz, 1H), 7.79-7.83 (m, 1H), 7.66 (t, J=7.1 Hz, 1H), 1.98 (q, J=7.4 Hz, 2H), 1.70 s, 3H), 1.09 (t, J=7.4 Hz, 3H); MS m/z=324 (M+1)

EXAMPLE 13: 2-ETHYL-2-METHYL-5-(3-QUINOLIN-4-YL-ALLYLIDENE)-[1,3]DIOXANE-4,6-DIONE

The compound 13 was synthesized from intermediate 1 3-Quinolin-4-yl-propenal, and 2-Ethyl-2-methyl-[1,3]dioxane-4,6-dione following the experimental procedure of compound 2. It was purified by flash column on $SiO_2$ (10%) EtOAc/Hexane to furnish orange solid (Yield 57%)

1H-NMR (400 MHz, CHLOROFORM-D) δ 9.06-8.98 (1H), 8.58-8.46 (1H), 8.34-8.26 (1H), 7.84-7.74 (2H), 7.71-7.63 (1H), 2.06-1.98 (2H), 1.76-1.72 (3H), 1.13-1.07 (3H) MS-ESI m/z=324 (M+1)

EXAMPLE 14: 2-METHYL-2-PROPYL-5-(3-QUINOLIN-4-YL-ALLYLIDENE)-[1,3]DIOXANE-4,6-DIONE

The compound 14 was synthesized from intermediate 1 3-Quinolin-4-yl-propenal, and 2-Methyl-2-propyl-[1,3]dioxane-4,6-dione following the experimental procedure of compound 2. It was purified by flash column on SiO2 (10%) EtOAc/Hexane to furnish orange solid (Yield 35%); 1H-NMR (400 MHz, DMSO-D6) δ 8.90 (d, J=4.6 Hz, 1H), 8.60 (dd, J=8.8, 5.8 Hz, 1H), 8.33-8.43 (m, 3H), 8.04 (d, J=8.5 Hz, 1H), 7.77 (d, J=4.6 Hz, 1H), 7.71 (t, J=7.1 Hz, 1H), 7.60 (t, J=7.1 Hz, 1H), 1.89-1.95 (m, 2H), 1.67-1.74 (m, 3H), 1.55 (dd, J=16.0, 7.6 Hz, 2H), 0.97-1.00 (m, 3H); MS-ESI m/z=338 (M+1)

EXAMPLE 15: 7-(3-QUINOLIN-4-YL-ALLYLIDENE)-5,9-DIOXA-SPIRO[3.5]NONANE-6,8-DIONE

The compound 15 was synthesized from intermediate 1 3-Quinolin-4-yl-propenal, and 5,9-Dioxa-spiro[3.5]nonane-6,8-dione following the experimental procedure of compound 2. It was purified by flash column on $SiO_2$ (10%) EtOAc/Hexane to furnish orange solid (Yield 58%)

1H-NMR (400 MHz, DMSO-D6) δ 8.90 (d, J=4.6 Hz, 1H), 8.62 (d, J=14.7 Hz, 1H), 8.28-8.40 (m, 3H), 8.00-8.05 (m, 1H), 7.50-7.77 (m, 3H), 2.53-2.60 (m, 4H), 1.93-2.01 (m, 2H); MS-ESI m/z=322 (M+1)

EXAMPLE 16: 7-(3-ISOQUINOLIN-4-YL-ALLYLIDENE)-5,9-DIOXA-SPIRO[3.5]NONANE-6,8-DIONE

The compound 16 was synthesized from intermediate 2 3-Isoquinolin-4-yl-propenal, and 5,9-Dioxa-spiro[3.5]nonane-6,8-dione following the experimental procedure of compound 2. It was purified by flash column on $SiO_2$ (10%) EtOAc/Hexane to furnish orange solid (Yield 60%); 1H-NMR (400 MHz, DMSO-D6) δ 9.21 (s, 1H), 8.92 (s, 1H), 8.51 (t, J=14.1 Hz, 1H), 8.27-8.37 (m, 3H), 8.04 (d, J=8.2 Hz, 1H), 7.79-7.83 (m, 1H), 7.64-7.68 (m, 1H), 2.58 (t, J=7.9 Hz, 4H), 1.93-2.01 (m, 2H); MS-ESI m/z=322 (M+1)

EXAMPLE 17: 3-(3-QUINOLIN-4-YL-ALLYLIDENE)-1,5-DIOXA-SPIRO[5.5]UNDECANE-2,4-DIONE

The compound 17 was synthesized from intermediate 1 3-Quinolin-4-yl-propenal, and 1,5-Dioxa-spiro[5.5]undecane-2,4-dione following the experimental procedure of compound 2. It was purified by flash column on $SiO_2$ (10%) EtOAc/Hexane to furnish orange solid (Yield 58%); 1H-NMR (400 MHz, CHLOROFORM-D) δ 9.01 (dd, J=14.9, 4.6 Hz, 1H), 8.51 (dd, J=15.3, 11.7 Hz, 1H), 8.08-8.32 (m, 4H), 7.65-7.83 (m, 3H), 1.95-2.02 (m, 4H), 1.71-1.77 (m, 4H), 1.51 (q, J=6.0 Hz, 2H); MS-ESI m/z=350 (M+1)

EXAMPLE 18: 2,2-DIMETHYL-5-(3-NAPHTHALEN-1-YL-ALLYLIDENE)-[1,3]DIOXANE-4,6-DIONE

Preparation of Compounds Using Wittig Reactions:

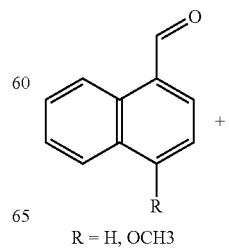

R = H, OCH3

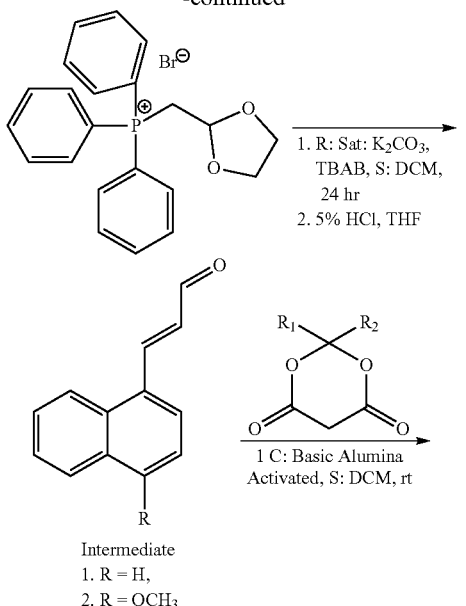

1. R: Sat: K₂CO₃, TBAB, S: DCM, 24 hr
2. 5% HCl, THF

1 C: Basic Alumina Activated, S: DCM, rt

Intermediate
1. R = H,
2. R = OCH₃

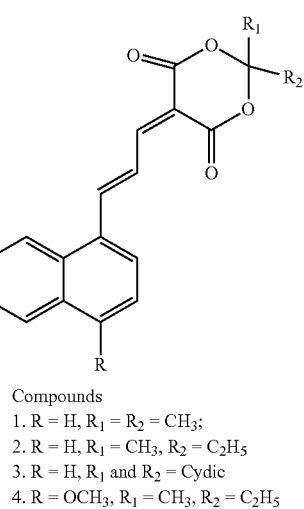

Compounds
1. R = H, R₁ = R₂ = CH₃;
2. R = H, R₁ = CH₃, R₂ = C₂H₅
3. R = H, R₁ and R₂ = Cydic
4. R = OCH₃, R₁ = CH₃, R₂ = C₂H₅

Preparation of Intermediate 1 3-Naphthalen-1-yl-propenal: (known in art but prepared with slight modification. Ref Xing, C. WO, 2016179597)

A mixture of Naphthalene-1-carbaldehyde (511 mg, 3.5 mmol), (1,2-dioxalan-2-ylmethy)triphenylphosphonium bromide (1.8 g, 4.2 mmol), tetrabutyl ammonium bromide (100 mg), in dichloromethane and sat. aq. K₂CO₃ (15 ml) in DCM (30 mL) was heated to refluxed for 15 h. The layers were separated and aqueous layer was extracted DCM (2×15 mL). The combined organic layer was washed with water (30 mL), and brine (50 mL), dried (Na₂SO₄) and concentrated. THF (10 ml), 10% HCl (5 mL) were added and mixture was stirred for 1 h at rt. The mixture was extracted with ethyl acetate (3×20 mL). The combined organic layers were washed with water (50 mL), and brine (30 mL) and dried over sodium sulfate and concentrated. The residue was purified by flash chromatography using ISCO Teledyne and 24 g pre packed silica column and ethyl acetate/hexane solvent gradient to afford yellow solid (350 mg, 55%).

Synthesis of Compound 18

The compound 18 was synthesized from 3-Naphthalen-1-yl-propenal and 2,2-Dimethyl-[1,3]dioxane-4,6-dione following the experimental procedure of compound 2. It was purified by flash column on SiO₂ (10%) EtOAc/Hexane to furnish orange solid (Yield 65%); 1H-NMR (400 MHz, DMSO-D6) δ 8.53-8.60 (m, 1H), 8.30-8.40 (m, 3H), 8.04 (d, J=7.1 Hz, 1H), 7.81-7.93 (m, 2H), 7.48-7.59 (m, 3H), 1.71-1.78 (m, 6H); MS-ESI m/z=331 (M+23)

EXAMPLE 19: 2 ETHYL,2-METHYL-5-(3-NAPHTHALEN-1-YL-ALLYLIDENE)-[1,3]DI-OXANE-4,6-DIONE

Synthesis of Compound 19

The compound 19 was synthesized from 3-Naphthalen-1-yl-propenal and 2-Ethyl-2-methyl-[1,3]dioxane-4,6-dione following the experimental procedure of compound 2. It was purified by flash column on SiO₂ (5 to 10%) EtOAc/Hexane to furnish orange solid (Yield 78%); 1H-NMR (400 MHz, DMSO-D6) δ 8.57 (td, J=11.7, 9.2 Hz, 1H), 8.31-8.40 (m, 3H), 8.04 (d, J=7.1 Hz, 1H), 7.81-7.93 (m, 2H), 7.48-7.59 (m, 3H), 1.98 (q, J=7.5 Hz, 2H), 1.67-1.73 (m, 3H), 1.04-1.10 (m, 3H); MS-ESI=345 (M+23)

EXAMPLE 20: 7-(3-NAPHTHALEN-1-YL-ALLY-LIDENE)-5,9-DIOXA-SPIRO[3.5]NONANE-6,8-DIONE

Synthesis of Compound 20

The compound 20 was synthesized from 3-Naphthalen-1-yl-propenal and 5,9-Dioxa-spiro[3.5]nonane-6,8-dione following the experimental procedure of compound 2. It was purified by flash column on SiO₂ (5 to 10%) EtOAc/Hexane to furnish orange solid (Yield 67%); 1H-NMR (400 MHz, DMSO-D6) δ 8.63 (d, J=14.6 Hz, 1H), 8.37 (m, 2H), 8.29 (m, 1H), 8.05 (d, J=7.1 Hz, 1H), 7.91 (d, J=7.0 Hz, 1H), 7.83 (d, J=6.9 Hz, 1H), 7.55-7.51 (m, 3H), 2.58-2.54 (m, 4H), 1.97-1.93 (m. 2H); MS-ESI m/z=321 (M+1)

Preparation of Intermediate 2 3-(4-Methoxy-naphthalen-1-yl)-propenal: (The intermediate is known in art but prepared using different procedure. (Ref from art: Israelashvili, S. J. Org. Chem. 1951, 16, 1519)

A mixture of 4-Methoxy-naphthalene-1-carbaldehyde (186 mg, 1 mmol), (1,2-dioxalan-2-ylmethy)triphenylphosphonium bromide (530 mg, 1.23 mmol), tetrabytyl ammonium bromide (20 mg), in dichloromethane and sat. aq. K₂CO₃ (5 ml) in DCM (10 mL) was heated to refluxed for 3 days. The layers were separated and aqueous layer was extracted DCM (2×15 mL). The combined organic layer was washed with water (10 mL), and brine (20 mL), dried (Na₂SO₄) and concentrated. THF (5 ml), 10% HCl (3 mL) were added and mixture was stirred for 1 h at rt. The mixture was extracted with ethyl acetate (3×20 mL). The combined organic layers were washed with water (20 mL), and brine (15 mL) and dried over sodium sulfate and concentrated. The product was carried to next step without further purification.

EXAMPLE 21, 2-ETHYL-5-[3-(4-METHOXY-NAPHTHALEN-1-YL)-ALLYLIDENE]-2-METHYL-[1,3]DIOXANE-4,6-DIONE

Synthesis of Compound 21

The compound 21 was synthesized from 3-(4-Methoxy-naphthalen-1-yl)-propenal and 2-Ethyl-2-methyl-[1,3]dioxane-4,6-dione following the experimental procedure of compound 2. It was purified by flash column on SiO₂ (5 to 10%) EtOAc/Hexane to furnish orange solid (Yield 45%); 1H-NMR (400 MHz, CHLOROFORM-D) δ 8.13-8.44 (m, 6H), 7.53-7.68 (m, 2H), 6.92 (dd, J=8.5, 1.4 Hz, 1H), 4.09 (s, 3H), 1.98-2.04 (m, 2H), 1.72 (d, J=1.4 Hz, 3H), 1.09 (td, J=7.4, 1.6 Hz, 3H); MS-ESI m/z=353 (M+1)

EXAMPLE 22: SYNTHESIS OF REDUCED COMPOUND 22 (2,2-DIMETHYL-5-(3-(NAPHTHALEN-1-YL)PROPYLIDENE)-1,3-DIOXANE-4,6-DIONE)

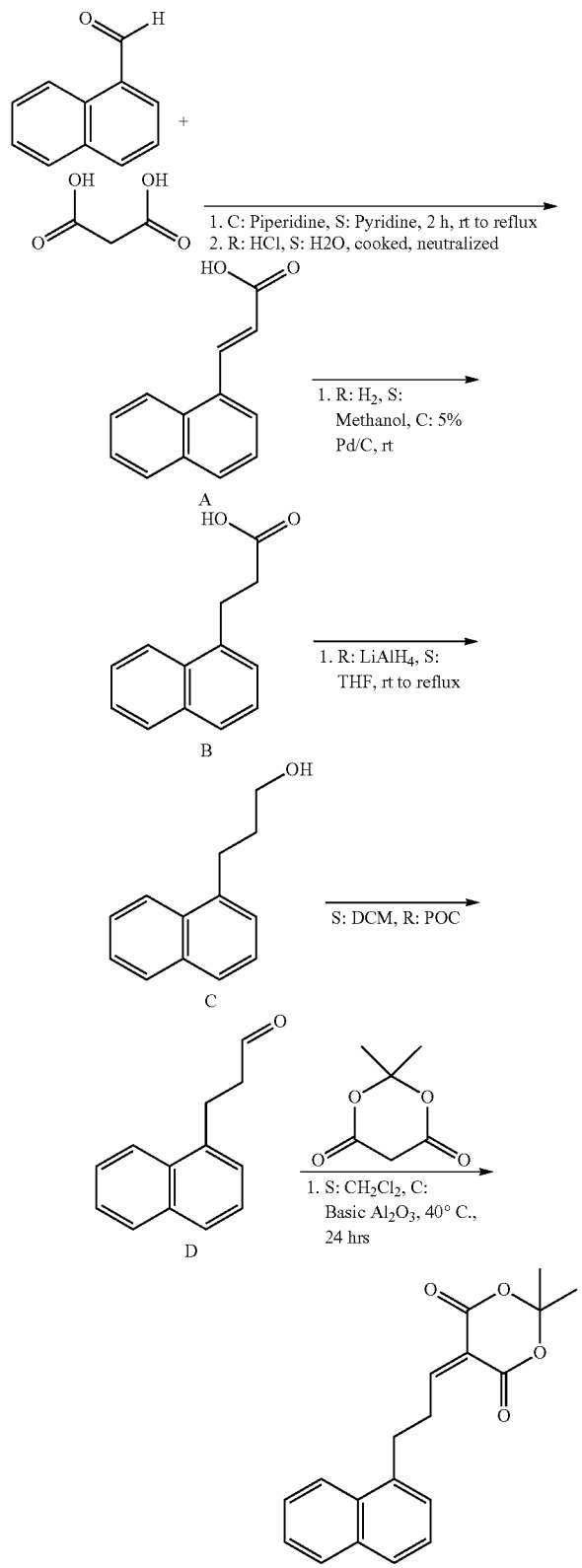

Synthesis of compound 22, Intermediate A, (E)-3-(naphthalen-1-yl)acrylic acid, was synthesized by condensing 1-naphthaldehyde with malonic acid as in art Ref: Lu X Y, Li J S, Wang S Q, Zhu Y J, Li Y M, Yan L Y, Li J M, Wang J Y, Zhou H P, Ge X T. Pd-Catalyzed decarboxylative cross-coupling reactions of epoxides with a, ß-unsaturated carboxylic acids. Chemical Communications. 2019; 55(74): 11123-6. Intermediate B, 3-(naphthalen-1-yl)propanoic acid, was synthesized by catalytic reduction of A using Pd and Hydrogen as in art Ref: Giardinetti M, Jessen N I, Christensen M L, Jorgensen K A. Organocatalytic [10+4] cycloadditions for the synthesis of functionalised benzo [a] azulenes. Chemical communications. 2019; 55(2):202-5. Intermediate C 3-Naphthalen-1-yl-propan-1-ol, was synthesized by reducing B using LiAlH4 in dry THF as in art Ref: Yan S Y, Han Y Q, Yao Q J, Nie X L, Liu L, Shi B F. Palladium (II)—Catalyzed Enantioselective Arylation of Unbiased Methylene C (sp3)-H Bonds Enabled by a 2-Pyridinylisopropyl Auxiliary and Chiral Phosphoric Acids. Angewandte Chemie International Edition. 2018 Jul. 16; 57(29):9093-7. Intermediate D, 3-Naphthalen-1-yl-propionaldehyde, was synthesized by oxidizing C, using PCC in DCM as in art Ref: Wang M M, Ning X S, Qu J P, Kang Y B. Dehydrogenative Synthesis of Linear α, β-Unsaturated Aldehydes with Oxygen at Room Temperature Enabled by t BuONO. ACS Catalysis. 2017 May 10; 7(6):4000-3. Compound 20 was synthesized following a method similar to the one used for the synthesis of compound 28. The residue was purified by flash chromatography using ISCO Teledyne and 12 g pre packed silica column and ethyl acetate/hexane solvent gradient to afford a pale yellow solid. (overall Yield, 30%)

1H-NMR (400 MHz, DMSO-D6) δ 8.07-8.11 (m, 1H), 7.88-7.93 (m, 1H), 7.77-7.80 (m, 1H), 7.37-7.50 (m, 3H), 7.33 (dd, J=7.0, 2.2 Hz, 1H), 3.21-3.51 (m, 4H), 1.50-1.63 (m, 6H); MS-ESI m/z=311 (M+1)

EXAMPLE 23, (E)-2,2-DIMETHYL-5-(3-(NAPHTHALEN-1-YL)ALLYL)-1,3-DIOXANE-4,6-DIONE

Synthesis of Compound 23:

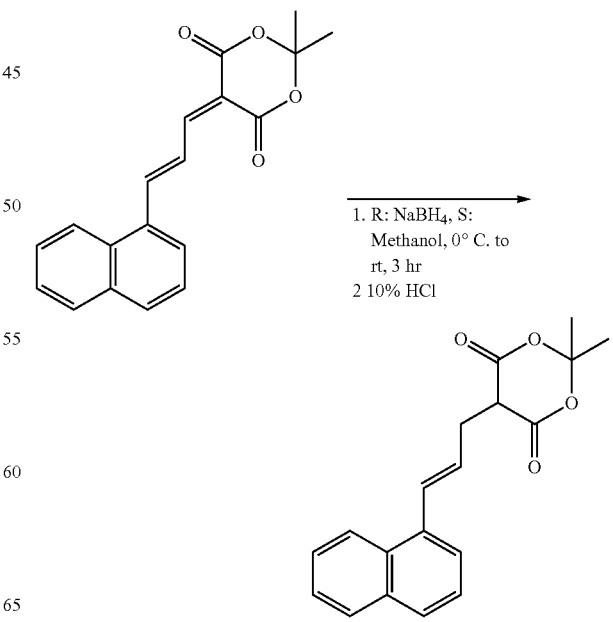

Into a 50 mL round bottom flask add 1 (0.2 g, 0.6 mmoles) and suspend in dry methanol (10 mL). Cool the mixture over ice/water to 0° C. then add NaBH$_4$ (0.12 g, excess) slowly over a period of 10 minutes. Allow the reaction mixture to stir for 3 hours at room temperature till the reactant is reduced to 23 and the mixture becomes clear. Remove the solvent under reduced pressure. Dissolve the white powder in water (5 mL) then precipitate the product as a white solid by adding 10% HCl. The white suspension was suction filtered and washed with copious amounts of water. (0.21 g, yield=100%); 1H-NMR (400 MHz, DMSO-D6) δ 8.06 (d, J=8.2 Hz, 1H), 7.64-7.83 (m, 2H), 7.23-7.50 (m, 5H), 6.12-6.27 (m, 2H), 4.46-4.53 (m, 1H), 2.95-3.09 (m, 2H), 2.81 (s, 3H), 1.76-1.98 (m, 3H), 1.59-1.73 (m, 3H); MS-ESI m/z=311 (M+1)

EXAMPLE 24: 2,2-DIMETHYL-5-(3-(NAPHTHA-LEN-1-YL)PROPYL)-1,3-DIOXANE-4,6-DIONE

Synthesis of Compound 24:

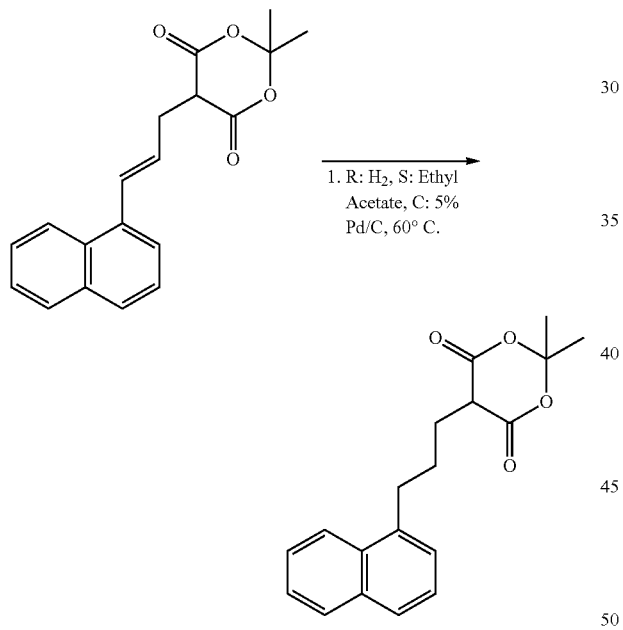

Into a round bottom flask (25 mL) was added compound 24 (60 mg, 0.2 mmoles) and dissolved in ethyl acetate (7 mL). The reactant was reduced over Pd/C (5%, 10 mg) and H$_2$ gas (1 atm) at 60° C. for 5 hours or till the reactant was consumed. The reaction mixture was filtered through celite to remove the catalyst and solvent removed under reduced pressure to obtain pure white solid (61 mg, yield=100%)

1H-NMR (400 MHz, DMSO-D6) δ 8.00 (d, J=8.5 Hz, 1H), 7.75 (d, J=8.0 Hz, 1H), 7.60-7.65 (m, 1H), 7.44-7.50 (m, 1H), 7.38 (t, J=7.3 Hz, 1H), 7.32 (dd, J=12.1, 7.3 Hz, 2H), 4.13-4.20 (m, 1H), 3.07-3.17 (m, 2H), 2.06-2.14 (m, 2H), 1.82-1.88 (m, 2H), 1.75 (d, J=13.5 Hz, 3H), 1.62-1.69 (m, 3H); MS-ESI m/z=313 (M+1)

EXAMPLE 25: 2,2-DIMETHYL-5-(3-NAPHTHA-LEN-2-YL-ALLYLIDENE)-[1,3]DIOXANE-4,6-DIONE

2-Naphthyl Analog:

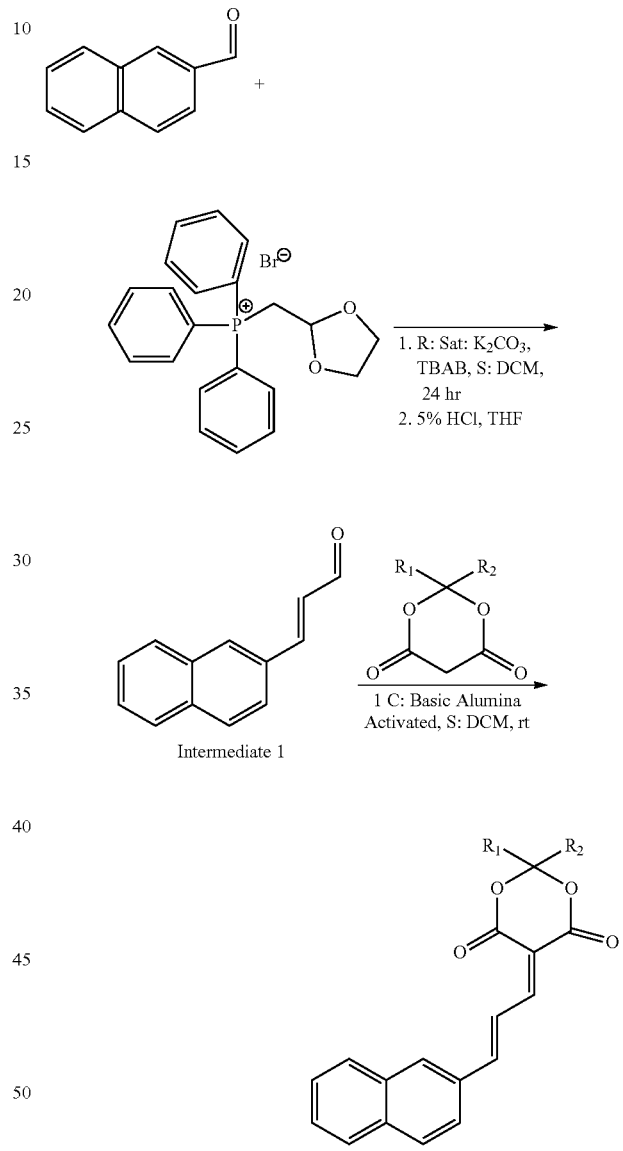

Compounds
1. $R_1 = R_2 = CH_3$;
2. $R_1 = CH_3, R_2 = C_2H_5$

Synthesis of Compound 25

The compound 25 was synthesized from 3-Naphthalen-2-yl-propenal and 2,2-Dimethyl-[1,3]dioxane-4,6-dione following the experimental procedure of Compound 2. It was purified by flash column on SiO$_2$ (5 to 10%) EtOAc/Hexane to furnish solid (Yield, 60%); 1H-NMR (400 MHz, DMSO-D6) δ 8.06-8.34 (m, 3H), 7.74-7.91 (m, 5H), 7.47-7.50 (m, 2H), 1.73 (s, 6H); MS-ESI m/z=309 (M+1)

EXAMPLE 26: 2-ETHYL-2-METHYL-5-(3-NAPHTHALEN-2-YL-ALLYLIDENE)-[1,3]DIOXANE-4,6-DIONE

Acetylene Analogs:

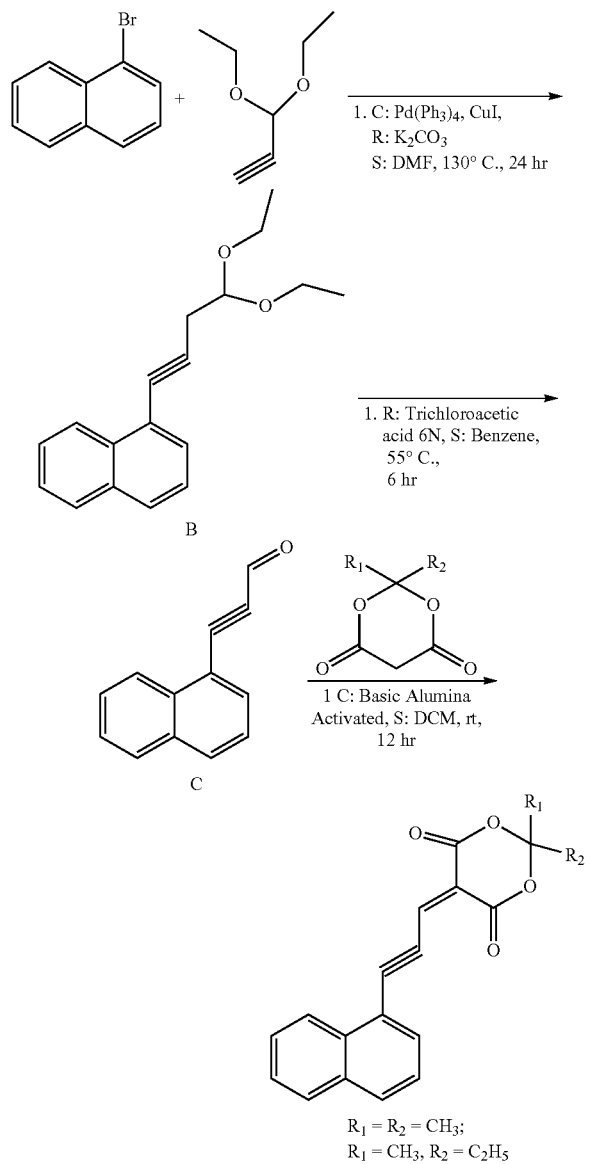

Synthesis of Compound 26:

The compound 26 was synthesized from 3-Naphthalen-2-yl-propenal and 2-Ethyl-2-methyl-[1,3]dioxane-4,6-dione following the experimental procedure of compound 28. It was purified by flash column on SiO₂ (5 to 10%) EtOAc/Hexane to furnish orange solid (Yield, 67%); 1H-NMR (400 MHz, DMSO-D6) δ ppm 8.52 (d, J=11.5 Hz, 1H), 8.38-8.32 (m, 3H), 8.03 (d, J=8.52, 1H), 7.99 (d, J=8.4 Hz, 2H), 7.82 (d, J=8.40, Hz, 1H), 7.55-7.51 (m, 3H), 1.97 (q, 2H), 1.68 (s, 3H), 1.09-1.06 (t, 3H); MS-ESI m/z=323 (M+1)

EXAMPLE 27: FURTHER SYNTHESIS OF ACETYLENE ANALOGS

Intermediate B in the scheme above, 1-(3-3-Diethoxy prop-1-ynyl)-naphthalene, was synthesized from 1-bromo naphthalene via Sonogashira coupling as in art Lemhadri, Mhamed et al, Tetrahedron, 61(41), 9839-9847; 2005 and Zhou, Bingnan et al, Organic Letters, 21(10), 3594-3599; 2019. Intermediate C, 3-(naphthalen-1-yl)prop-2-ynal, was synthesized by hydrolyzing intermediate B in trichloro acetic acid as in art Zhou, Bingnan et al, Organic Letters, 21(10), 3594-3599.

EXAMPLE 28: 2,2-DIMETHYL-5-(3-NAPHTHALEN-1-YL-PROP-2-YNYLIDENE)-[1,3]DIOXANE-4,6-DIONE

Synthesis of Compound 28

A Mixture of 3-(naphthalen-1-yl)prop-2-ynal), Intermediare C (120 mg, 0.66 mmol), 2,2-Dimethyl-[1,3]dioxane-4,6-dione (120 mg, 0.77 mmol), Aluminum Oxide, activated, basic, Brockman I (500 mg) in DCM 10 ml was stirred at room temp overnight. The reaction mixture was filtered and organic solvent removed under reduced pressure. The residue was purified by flash chromatography using ISCO Teledyne and 12 g pre packed silica column and ethyl acetate/hexane solvent gradient to afford yellowish solid (88 mg, 43%)

1H-NMR (400 MHz, DMSO-D6) δ ppm, 8.64 (d, J=8.5 Hz, 1H), 7.81-8.00 (m, 4H), 7.49-7.67 (m, 3H), 1.78 (s, 6H), MS-ESI m/z=307 (M+1)

EXAMPLE 29: 2-ETHYL-2-METHYL-5-(3-NAPHTHALEN-1-YL-PROP-2-YNYLIDENE)-[1,3]DIOXANE-4,6-DIONE

Synthesis of Compound 29

Compound 29 was synthesized as compound from 3-(naphthalen-1-yl)prop-2-ynal and 2-Ethyl-2-methyl-[1,3]dioxane-4,6-dione following the experimental procedure detailed the synthesis of compound 27. Yield (80 mg, 37%)

1H-NMR (400 MHz, DMSO-D6) δ ppm 8.65 (d, J=8.2 Hz, 1H), 7.81-8.00 (m, 4H), 7.49-7.67 (m, 3H), 2.00 (q, J=7.4 Hz, 2H), 1.73 (s, 3H), 1.10 (t, J=7.4 Hz, 3H); MS-ESI m/z=321 (M+1)

EXAMPLE 30: 7-(3-NAPHTHALEN-1-YL-PROP-2-YNYLIDENE)-5,9-DIOXA-SPIRO[3.5]NONANE-6,8-DIONE

Synthesis of Compound 30

Compound 30 was synthesized as compound from 3-(naphthalen-1-yl)prop-2-ynal and 5,9-Dioxa-spiro[3.5]nonane-6,8-dione following the experimental procedure detailed the synthesis of compound 27 Yield. (110 mg, 60%)

1H-NMR (400 MHz, DMSO-D6) δ ppm 8.62 (d, J=8.5 Hz, 1H), 8.00 (d, J=8.2 Hz, 1H), 7.86-7.90 (m, 2H), 7.77 (d, J=1.6 Hz, 1H), 7.64-7.68 (m, 1H), 7.49-7.57 (m, 2H), 2.61 (td, J=8.0, 1.5 Hz, 4H), 1.96-2.00 (m, 2H); MS-ESI m/z=307 (M+1)

EXAMPLE 31: SYNTHESIS OF BENZOFURAN ANALOGS

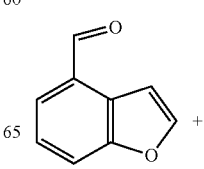

-continued

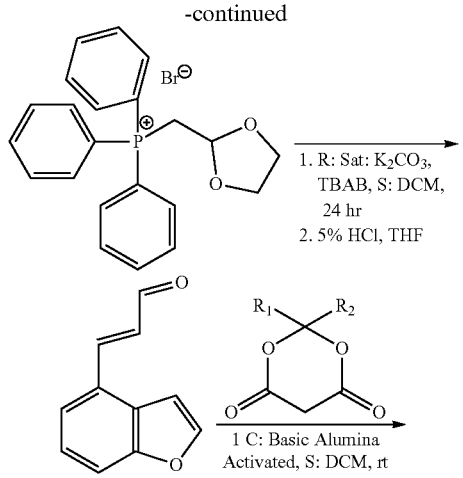

New intermediate
Not known in Lit.

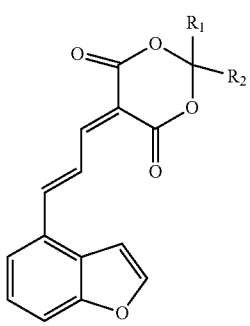

Compounds
1. $R_1 = R_2 = CH_3$;
2. $R_1 = CH_3, R_2 = C_2H_5$

Synthesis of Intermediate 1 3-Benzofuran-4-yl-propenal:

A mixture of Benzofuran-4-carbaldehyde (219 mg, 1.5 mmol), (1,2-dioxalan-2-ylmethy)triphenylphosphonium 7 bromide (858 mg, 2 mmol), tetrabytyl ammonium bromide (30 mg), in dichloromethane and sat. aq. $K_2CO_3$ (8 ml) in DCM (10 mL) was heated to refluxed for 20 h. The layers were separated and aqueous layer was extracted DCM (2×10 mL). The combined organic layer was washed with water (10 mL), and brine (20 mL), dried (NaSO4) and concentrated. THF (10 ml), 5% HCl (3 mL) were added and mixture was stirred for 1 h at rt. The mixture was extracted with ethyl acetate (3×20 mL). The combined organic layers were washed with water (20 mL), and brine (15 mL) and dried over sodium sulfate to afford yellow semi solid. It was purified by flash column on SiO2 (5 to 10%) EtOAc/Hexane to furnish yellow solid (130 mg, Yield 50%)

1H-NMR (400 MHz, DMSO-D6) δ 9.69 (d, J=9.2, 1H), 7.81 (m, 2H), 7.51 (m, 2h), 7.32 (m, 1H), 7.18 (m, 1H), 6.79 (q, J=7.5 Hz, 1H)

EXAMPLE 32: 5-(3-BENZOFURAN-4-YL-ALLYLIDENE)-2,2-DIMETHYL-[1,3]DIOXANE-4,6-DIONE

Synthesis of Compound 32

The compound 30 was synthesized from 3-Benzofuran-4-yl-propenal and 2,2-dimethyl-[1,3]dioxane-4,6-dione following the experimental procedure of compound 2. It was purified by flash column on $SiO_2$ (5 to 10%) EtOAc/Hexane to furnish solid (Yield 69%); 1H-NMR (400 MHz, CHLO-ROFORM-D) δ 8.47 (dd, J=15.3, 12.1 Hz, 1H), 8.24 (d, J=11.9 Hz, 1H), 7.59-7.79 (m, 4H), 7.15-7.37 (m, 2H), 1.77 (s, 6H); MS-ESI m/z=299 (M+1)

EXAMPLE 33: 5-(3-BENZOFURAN-4-YL-ALLYLIDENE)-2-ETHYL-2-METHYL-[1,3]DIOXANE-4,6-DIONE

Synthesis of Compound 33

The compound 33 was synthesized from 3-Benzofuran-4-yl-propenal and 2-Ethyl-2-methyl-[1,3]dioxane-4,6-dione following the experimental procedure of Compound 2. It was purified by flash column on $SiO_2$ (5 to 10%) EtOAc/Hexane to furnish orange solid (Yield 71%); 1H-NMR (400 MHz, DMSO-D6) δ 8.21-8.39 (m, 2H), 7.83-7.97 (m, 2H), 7.52-7.61 (m, 2H), 7.26-7.33 (m, 2H), 1.96 (q, J=7.5 Hz, 2H), 1.67 (s, 3H), 1.04-1.09 (m, 3H); MS-ESI m/z=336 (M+23)

EXAMPLE 34: BENZOTHIOPHENE ANALOGS

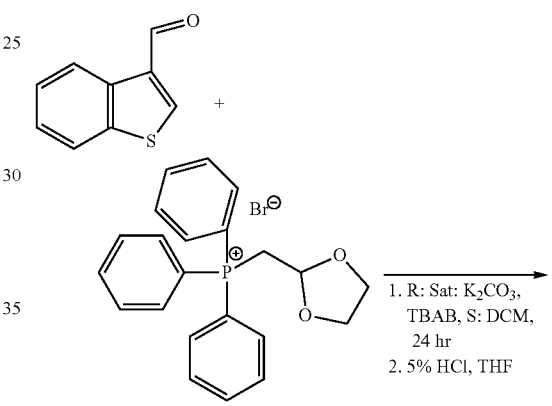

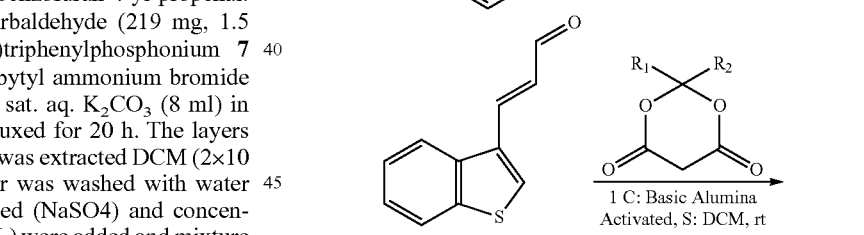

Intermediate 1

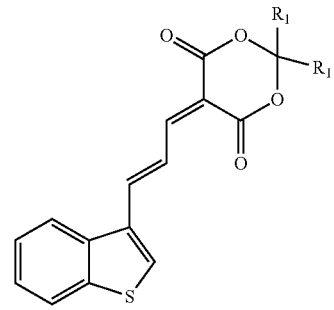

Compounds
1. $R_1 = R_2 = CH_3$;
2. $R_1 = CH_3, R_2 = C_2H_5$

Synthesis of Intermediate 1 3-Benzo[b]thiophen-3-yl-propenal: synthesis of intermediate 1 is known in literature but it was synthesized by a new procedure as follows: A mixture of Benzo[b]thiophene-3-carbaldehyde (243 mg, 1.5 mmol), (1,2-dioxalan-2-ylmethy)triphenylphosphonium bromide (858 mg, 2 mmol), tetrabytyl ammonium bromide (30 mg), in dichloromethane and sat. aq. $K_2CO_3$ (8 ml) in DCM (10 mL) was heated to refluxed for 20 h. The layers were separated and aqueous layer was extracted DCM (2×10 mL). The combined organic layer was washed with water (10 mL), and brine (20 mL), dried ($Na_2SO_4$) and concentrated. THF (10 ml), 5% HCl (3 mL) were added and mixture was stirred for 1 h at rt. The mixture was extracted with ethyl acetate (2×20 mL). The combined organic layers were washed with water (20 mL), and brine (15 mL) and dried over sodium sulfate to afford yellow semi solid. It was purified by flash column on SiO2 (10%) EtOAc/Hexane to furnish yellow solid (170 mg, Yield 60%); 1H-NMR (400 MHz, DMSO-D6) δ 9.67 (d, J=7.8, 1H), 8.15 s, 1H) 8.04 (d, J=7.88 1H), 7.86 (m, 2h), 7.40 (m, 2H), 6.83 (q, J=7.56 Hz, 1H)

EXAMPLE 35: 5-(3-BENZO[B]THIOPHEN-3-YL-ALLYLIDENE)-2,2-DIMETHYL-[1,3]DIOXANE-4,6-DIONE

Synthesis of Compound 35
The compound 34 was synthesized from 3-Benzo[b]thiophen-3-yl-propenal and 2,2-Dimethyl-[1,3]dioxane-4,6-dione following the experimental procedure of compound 2. It was purified by flash column on SiO2 (10%) EtOAc/Hexane to furnish orange solid (Yield 66%); 1H-NMR (400 MHz, CHLOROFORM-D) δ 8.42 (dd, J=15.3, 12.1 Hz, 1H), 8.04-8.24 (m, 3H), 7.90 (dd, J=8.0, 0.7 Hz, 1H), 7.43-7.71 (m, 3H), 7.25 (d, J=0.7 Hz, 1H), 1.77 (s, 6H); MS-ESI m/z=315 (M+1)

EXAMPLE 36: 5-(3-BENZO[B]THIOPHEN-3-YL-ALLYLIDENE)-2-ETHYL-2-METHYL-[1,3]DIOXANE-4,6-DIONE

Synthesis of Compound 36
The compound 33 was synthesized from 3-Benzo[b]thiophen-3-yl-propenal and 2-Ethyl-2-methyl-[1,3]dioxane-4,6-dione following the experimental procedure of compound 2. It was purified by flash column on SiO2 (10%) EtOAc/Hexane to furnish orange solid (Yield 57%); 1H-NMR (400 MHz, CHLOROFORM-D) δ 8.43 (dd, J=15.3, 12.1 Hz, 1H), 8.05-8.24 (m, 3H), 7.90 (dd, J=8.0, 0.7 Hz, 1H), 7.45-7.70 (m, 3H), 2.00 (q, J=7.4 Hz, 2H), 1.72 (s, 3H), 1.09 (t, J=7.4 Hz, 3H); MS-ESI m/z=352 (M+23)

EXAMPLE 37: SYNTHESIS OF HEAD GROUPS

Head groups were prepared according to procedure in art. Representative scheme and references are given below.
Synthesis of 5,9-Dioxa-spiro[3.5]nonane-6,8-dione: Synthesized as below.

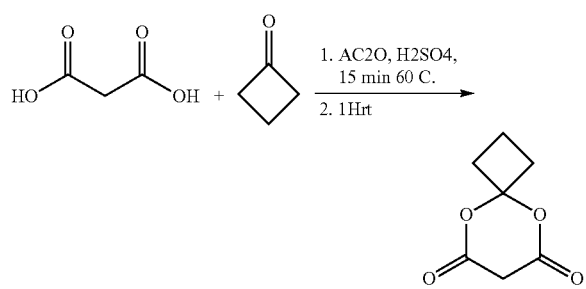

Ref: Rostein, B. H. et. al. Nature communication, 2014, 9, 4365

2-Ethyl-2-methyl-[1,3]dioxane-4,6-dione

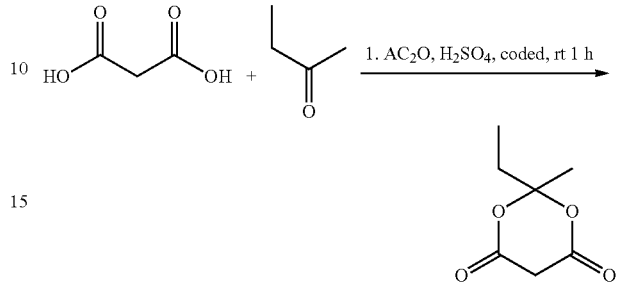

Ref: Carneiro, V. M., European Journal of Chemistry, 2015, 97, 42-54

1,5-Dioxa-spiro[5.5]undecane-2,4-dione

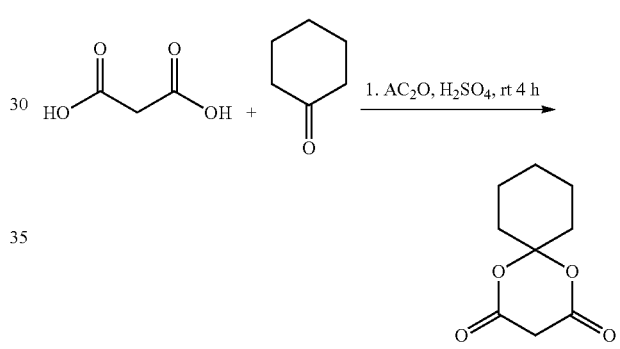

Ref: Zeng, W, Crystal, 2016, 6, 69

EXAMPLE 38: TESTING AND CHARACTERIZATION OF

Antiproliferative Activity
Cell Culture: The human breast cancer epithelial cell lines MDA-MB-231 (HTB-26™), MCF-7 (HTB-22™), colon cancer cell lines HCT 116 (CCL-247™) and HCT6 (CCL-244™) were obtained from American Type Culture Collection (ATCC). Additionally, KAIMRC1 cell line was isolated and developed at KAIMRC from a Saudi breast cancer patient. All the cells were grown in advanced DMEM containing 10% fetal bovine serum (FBS), 50 units/mL penicillin, 50 ug/mL streptomycin (GIBCO), and 2 mM glutamine (GIBCO). The cells were cultured at 37° C. in a humidified 5% CO2 atmosphere for 24 hours before experimental procedure.
Cell Proliferation Assay (MTT): Cells were plated on flat-bottom 96-well plates at a density of 5×103 cells/well in 100 μL growth medium. Serial dilutions of the compounds, ranging from 100 nM-100 μM were tested on the cells in triplicates. Additional rows with only the compounds and only cells were added in order to account for the compounds and cells effect. Cells were incubated with compounds for 48 h at 37° C. with 5% CO2.

After 48 h treatment, the cell viability was determined using the MTT viability assay. Briefly, 5 µL of MTT reagent (5 mg/mL stock) per 95 µl cell culture medium was added to each well and incubated for 3 h at 37° C. with 5% CO2. After 3 h the supernatant was removed, and the MTT formazan crystals were dissolved in dimethyl sulfoxide (DMSO) by shaking the plate for 30 mins at RT. The absorbance was measured on Molecular Devices microplate absorbance reader at 560 nm. The percentage of viable cells was calculated as the ratio of the absorbance of the treated group divided by the absorbance of the control group multiplied by 100. The absorbance from the untreated control cells was set as 100% viable. IC50 values were calculated from dose-response curves generated using a polynomial dose-response approximation using Prism 8 software. The IC50 values (□M) obtained for the compounds of present invention on MDA-MD 231 (breast), MCF-7 (breast), KAIMRC1 (breast), HCT116 (colon) and HCT8 (colon) are summarized in Table 5 and 6.

TABLE 5

MTT assay results for the MDA MB-231 cell line

| Compound | $IC_{50}$ µM MDA MB-231 (Breast) |
|---|---|
| Example 1 | 52.03 |
| Example 2 | 25.17 |
| Example 6 | 21.17 |
| Example 13 | 10.98 |
| Example 11 | 14.07 |
| Example 17 | 12.99 |
| Example 9 | 5.03 |
| Example 14 | 15.46 |
| Example 15 | 7.84 |
| Example 19 | 5.92 |
| Example 12 | 6.05 |
| Example 32 | 7.50 |
| Example 21 | 17.01 |
| Example 31 | 17.01 |
| Example 31 | 54.61 |
| Mitoxanthrone | 0.51 |

TABLE 6

MTT assay for the MCF-7, HCT116, HCT68, KAIMRC1 cell lines.

| Compound | $IC_{50}$ µM MCF-7 (Breast) | $IC_{50}$ µM HCT116 (Colon) | $IC_{50}$ µM HCT68 (Colon) | $IC_{50}$ µM KAIMRC1 (Breast) |
|---|---|---|---|---|
| Example1 | 10.50 | 27.07 | | |
| Example 6 | 31.95 | | | 17.97 |
| Example13 | 9.15 | 6.38 | 19.82 | 14.37 |
| Example11 | 19.69 | 10.41 | 14.12 | 33.21 |
| Example17 | 17.31 | 13.69 | 12.91 | 19.61 |
| Example 9 | 24.23 | 3.54 | 2.17 | 21.64 |
| Example14 | 15.16 | 15.42 | 18.95 | 27.58 |
| Example19 | 5.82 | 2.44 | 2.95 | 5.82 |
| Example18 | | | 5.78 | 6.54 |
| Example 20 | 4.24 | 4.84 | 3.87 | 11.89 |
| Example12 | 9.29 | 2.47 | 1.87 | 4.25 |
| Example10 | | | 1.37 | 4.45 |
| Example16 | 5.44 | 8.04 | 6.01 | 8.09 |
| Example 28 | | | 8.82 | 7.36 |
| Example 27 | | | 7.17 | 7.36 |
| Example 32 | | 34.17 | | |
| Example 21 | | 50.03 | | |
| Example 31 | | 34.13 | | |
| Mitoxanthrone | 3.61 | 0.71 | 1.25 | 10.05 |

Blank spaces indicate "not tested".

A review of Tables 5 and 6 shows that compounds 9, 13, 12 and 10 demonstrate the range of activity that begins to overlap with that of Mitoxanthrone, selected as exemplary cytotoxic antineoplastic agent. The presence of nitrogen in certain positions of quinoline and/or iso-quinoline ring is the structure-activity determinant, and the subsequent variations in the nitrogen positions and substituents in this ring produce stronger leads by the methods of combinatorial expansion disclosed herein.

EXAMPLE 39: CELL PROLIFERATION ASSAY
(CELL TITRE-GLO LUMINESCENT CELL
VIABILITY ASSAY)

Cell Titre Glo assay was performed on two Leukemia cell lines, HL 60 and ThP1 as per manufacturer's (Promega) recommendations. Briefly, plates were prepared as mentioned in cell culture section. 100 □L of Cell Titre Glo was added directly to the wells. After incubation for 30 minutes at room temperature, luminescence was measured using the Envision plate reader (Perkin Elmer). Luminescence readings were normalized to averaged DMSO controls and expressed as relative percentage. IC50 values were calculated from dose-response curves generated using a polynomial dose-response approximation using Prism 8 software.

TABLE 7

Results of the Cell Titre Glo proliferation assay

| Compound | $IC_{50}$ µM HL 60 (leukemia) | $IC_{50}$ µM ThP1 (leukemia) |
|---|---|---|
| Example 13 | 1.04 | 0.88 |
| Example 11 | 1.86 | 1.68 |
| Example 9 | | 2.81 |
| Example 20 | 2.41 | 2.04 |
| Example12 | 2.05 | 1.82 |
| Example10 | | 1.51 |
| Mitoxanthrone | 0.70 | 0.22 |

Figure 3:
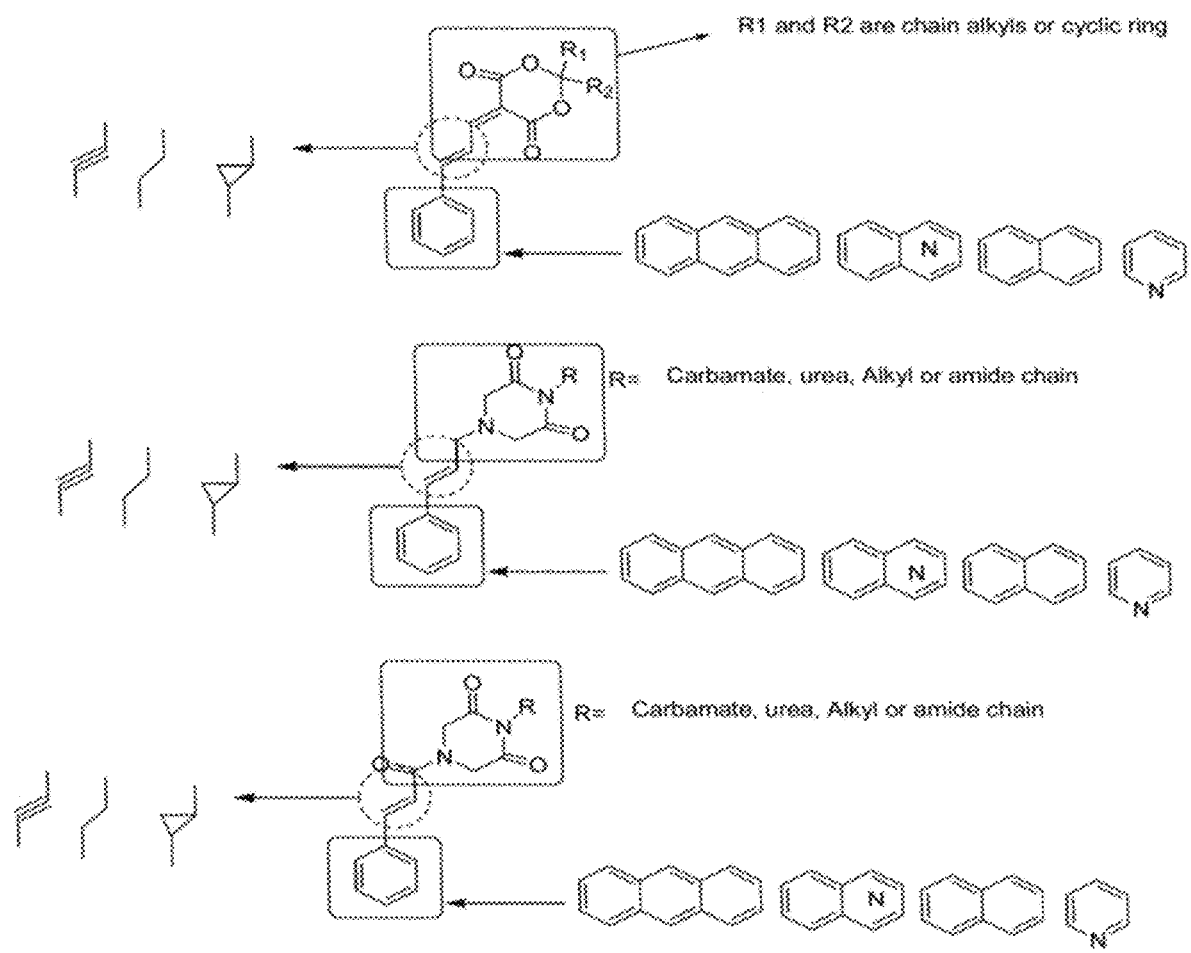
FIG. 3 shows the preferred structural embodiments of the present disclosure.

The results indicate the compound 49 approaches the level of activity of the positive control. The tested embodiments of the invention are summarized in FIG. 3.

The invention claimed is:

1. A compound having a 1,3-dioxane-4,6-dione structure of formula (I):

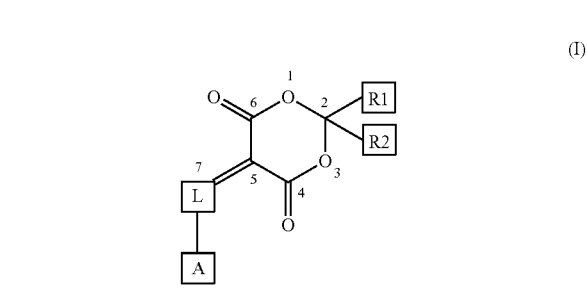

(I)

wherein L is a linker,
wherein the linker L is selected from the group consisting of the structures:

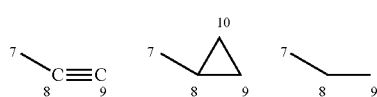

wherein, except when 8 and 9 are separated by a triple bond, each carbon 7, 8 or 9 can be substituted by, independently, one or more hydrogen atoms or by one or more side chains wherein the side chains can be linear or branched, substituted or unsubstituted aliphatic or aromatic, heteroaromatic, monocyclic or polycyclic, homocyclic or heterocyclic groups, wherein the substituents in the positions 7-9 of the linker are independently selected from the group consisting of hydrogen, alkyl, cycloalkyl, alkene, cycloalkene, aryl, alkyne, linear or cyclic diene, acyl, anhydride, haloanhydride, halide, carbene, amide, ether, ester, hydroxyl, aldehyde, ketone, acetal, ketal, hemiacetal, amine, nitrile, isonitrile, cyanide, nitrate, nitrite, enamine, oxime, thiol, sulfate, sulfoxide, sulfonamide, sulfone, siloxane, silane, silyl, aminoacid, wherein the carbon 9 of the linker is connected by a single bond to the aromatic system A through a C, N, O, or S atom, wherein A is a mononuclear or polynuclear aromatic system having the structure:

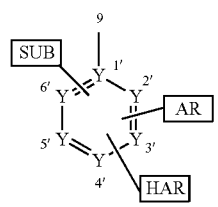

wherein the position 9 is the carbon on the linker L, wherein Y are any of C, N, O and S forming together a 6 or 5-member aromatic system, wherein the number of atoms of any elements among C, N, O, S can be 0 to 6 in the positions 1'-6' of the ring, wherein SUB are non-bridging substituents or non-aromatic bridging substituents, wherein the non-bridging substituents have only one connection to the ring 1'-6', wherein the non-aromatic bridging substituents connect any of the positions 1'-6' with any of the positions 1'-6' in any order, with the proviso that the aromatic rings that form as parts of the bridges are not directly fused with the ring 1'-6', wherein AR are all-carbon aromatic substituents, defined as fused rings formed by overlapping any of the bonds 1'-2', 2'-3', 3'-4', 4'-5', 5'-6' with one bond comprising the substituting all-carbon aromatic ring, wherein HAR are heteroaromatic substituents, wherein 0-10 aliphatic or aromatic, carbocylic or heterocyclic rings can form between the substituents SUB, between SUB and L and between SUB and R1 or R2, between SUB and AR or HAR, between AR and HAR, between AR and AR, between HAR and HAR, or between the substituents thereof in any combination, wherein R1 and R2 are linear or branched alkyls, cycloalkyls, substituted alkyls, independently substituted by hydrogen or by other groups, wherein one carbon or more connected to the carbon 2 of the 1,3-dioxane-4,6-dione ring of the compound of formula (I) is an alkyl, with the first bond from the carbon 2 being a carbon-carbon bond, wherein the groups R1, R2, SUB, AR and HAR can be further substituted independently by one or more selected from the group consisting of hydrogen, alkyl, cycloalkyl, alkene, cycloalkene, alkyne, diene, acyl, anhydride, haloanhydride, halide, carbene, amide, ether, ester, hydroxyl, aldehyde, ketone, acetal, ketal, hemiacetal, carboxylic, amine, nitrile, isonitrile, cyanide, nitrate, nitrite, azide, hydrazide, enamine, oxime, thiol, sulfate, sulfoxide, sulfonamide, siloxane, silane, silyl, and aminoacid, with the proviso that the following is not included in formula (I):

1,3-Dioxane-4,6-dione, 2-[hydroxy[(1R,2R)-2-phenylcyclopropyl]methylene]-5,5-dimethyl.

2. A compound having the following 1,3-dioxane-4,6-dione structure:

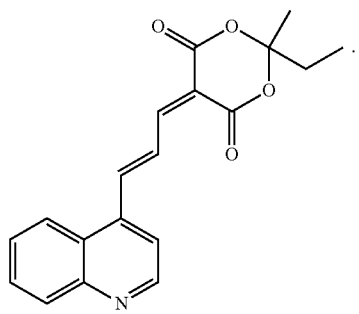 [SMILES: CCC1(C)OC(=O)C(=C/C=C/c2ccnc3ccccc23)C(=O)O1]

3. A compound having the following 1,3-dioxane-4,6-dione structure:

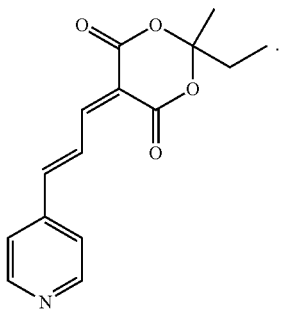 [SMILES: CCC1(C)OC(=O)C(=C/C=C/c2ccncc2)C(=O)O1]

4. A compound having the following 1,3-dioxane-4,6-dione structure:

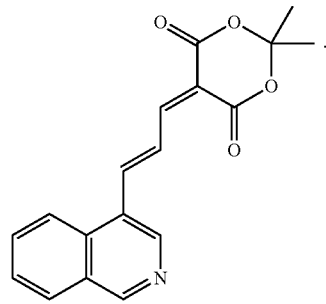 [SMILES: CC1(C)OC(=O)C(=C/C=C/c2cncc3ccccc23)C(=O)O1]

5. A compound having a 1,3-dioxane-4,6-dione structure selected from the group consisting of:

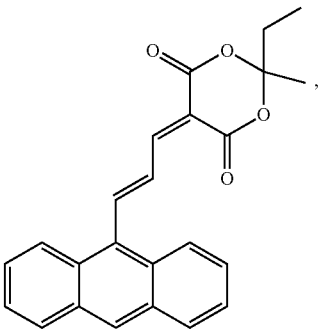

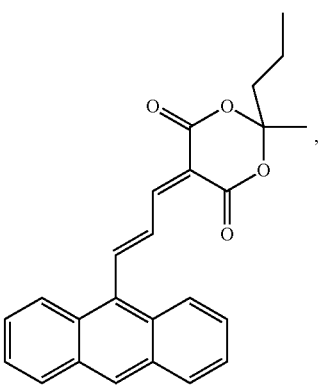

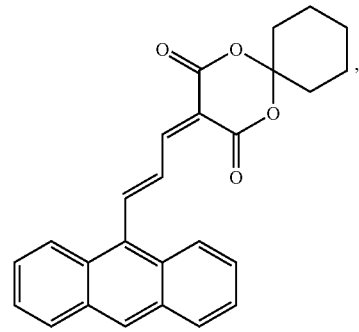

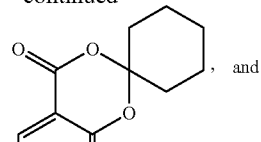, and

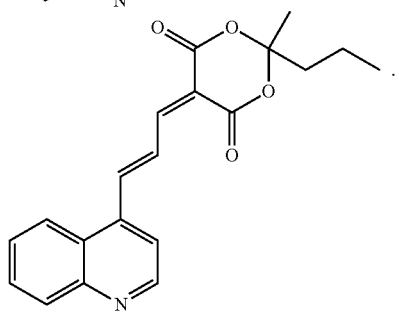

6. A method of treating a cancer selected from the group consisting of leukemia, breast cancer and colon cancer, comprising:
   administering an effective amount of the compound of formula (I) of claim 1 to a patient in need of treatment for the cancer.

7. The method of claim 6, wherein the patient is a human.

8. A method of treating a cancer selected from the group consisting of leukemia, breast cancer and colon cancer, comprising:
   administering an effective amount of the compound of claim 2 to a patient in need of treatment for the cancer.

9. A method of treating a cancer selected from the group consisting of leukemia, breast cancer and colon cancer, comprising:
   administering an effective amount of the compound of claim 3 to a patient in need of treatment for the cancer.

10. A method of treating a cancer selected from the group consisting of leukemia, breast cancer and colon cancer, comprising:
    administering an effective amount of the compound of claim 4 to a patient in need of treatment for the cancer.

11. A method of treating a cancer selected from the group consisting of breast cancer and colon cancer, comprising:
    administering an effective amount of the compound of claim 5 to a patient in need of treatment for the cancer.

* * * * *

UNITED STATES PATENT AND TRADEMARK OFFICE
CERTIFICATE OF CORRECTION

PATENT NO. : 11,161,823 B2  
APPLICATION NO. : 16/810051  
DATED : November 2, 2021  
INVENTOR(S) : Imadul Islam et al.

Page 1 of 1

It is certified that error appears in the above-identified patent and that said Letters Patent is hereby corrected as shown below:

On the Title Page

Item (73), the Assignee's information is incorrect. Item (73) should read:  
-- (73) Assignees: National Guard Health Affairs, Riyadh (SA); King Saud bin Abdulaziz University for Health Sciences, Riyadh (SA); King Abdullah International Medical Research Center, Riyadh (SA) --

Signed and Sealed this  
Twenty-ninth Day of March, 2022

Drew Hirshfeld  
*Performing the Functions and Duties of the  
Under Secretary of Commerce for Intellectual Property and  
Director of the United States Patent and Trademark Office*